(12) United States Patent
Tearney et al.

(10) Patent No.: US 7,843,572 B2
(45) Date of Patent: Nov. 30, 2010

(54) METHOD AND APPARATUS FOR OPTICAL IMAGING VIA SPECTRAL ENCODING

(75) Inventors: Guillermo J. Tearney, Cambridge, MA (US); Dvir Yelin, Brookline, MA (US); Brett Eugene Bourna, Quincy, MA (US)

(73) Assignee: The General Hospital Corporation, Boston, MA (US)

( * ) Notice: Subject to any disclaimer, the term of this patent is extended or adjusted under 35 U.S.C. 154(b) by 778 days.

(21) Appl. No.: 11/537,170

(22) Filed: Sep. 29, 2006

(65) Prior Publication Data

US 2007/0233396 A1 Oct. 4, 2007

Related U.S. Application Data

(60) Provisional application No. 60/721,802, filed on Sep. 29, 2005.

(51) Int. Cl.
G01B 9/02 (2006.01)
(52) U.S. Cl. ..................................... 356/479
(58) Field of Classification Search ............... 356/477, 356/479, 497; 250/227.19, 227.27; 385/12
See application file for complete search history.

(56) References Cited

U.S. PATENT DOCUMENTS

| 2,339,754 | A | 1/1944 | Brace |
| 3,090,753 | A | 5/1963 | Matuszak et al. |
| 3,601,480 | A | 8/1971 | Randall |
| 3,856,000 | A | 12/1974 | Chikama |
| 3,872,407 | A | 3/1975 | Hughes |
| 3,941,121 | A | 3/1976 | Olinger |
| 3,973,219 | A | 8/1976 | Tang et al. |
| 3,983,507 | A | 9/1976 | Tang et al. |
| 4,030,827 | A | 6/1977 | Delhaye et al. |
| 4,140,364 | A | 2/1979 | Yamashita et al. |
| 4,141,362 | A | 2/1979 | Wurster |
| 4,224,929 | A | 9/1980 | Furihata |

(Continued)

FOREIGN PATENT DOCUMENTS

DE 4105221 9/1991

(Continued)

OTHER PUBLICATIONS

Liptak David C. et al., (2007) "On the Development of a Confocal Rayleigh-Brillouin Microscope" *American Institute of Physics* vol. 78, 016106.

(Continued)

*Primary Examiner*—Michael A Lyons
(74) *Attorney, Agent, or Firm*—Dorsey & Whitney LLP

(57) ABSTRACT

Exemplary method, apparatus and arrangement can be provided for obtaining information associated with a sample such as a portion of an anatomical structure. The information can be generated using first data, which can be based on a signal obtained from a location on the sample, and second data, where the second data can be obtained by combining a second signal received from the sample with a third reference signal. An image of a portion of the sample can also be generated based on the information. For example, the first data can be associated with spectral encoding microscopy data, and the second data can be associated with optical coherence tomography data.

23 Claims, 36 Drawing Sheets

U.S. PATENT DOCUMENTS

| | | |
|---|---|---|
| 4,295,738 A | 10/1981 | Meltz et al. |
| 4,300,816 A | 11/1981 | Snitzer et al. |
| 4,303,300 A | 12/1981 | Pressiat et al. |
| 4,428,643 A | 1/1984 | Kay |
| 4,479,499 A | 10/1984 | Alfano |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,650,327 A | 3/1987 | Ogi |
| 4,744,656 A | 5/1988 | Moran et al. |
| 4,751,706 A | 6/1988 | Rohde et al. |
| 4,770,492 A | 9/1988 | Levin et al. |
| 4,827,907 A | 5/1989 | Tashiro et al. |
| 4,834,111 A | 5/1989 | Khanna et al. |
| 4,868,834 A | 9/1989 | Fox et al. |
| 4,890,901 A | 1/1990 | Cross, Jr. |
| 4,892,406 A | 1/1990 | Waters |
| 4,909,631 A | 3/1990 | Tan et al. |
| 4,925,302 A | 5/1990 | Cutler |
| 4,928,005 A | 5/1990 | Lefevre et al. |
| 4,965,441 A | 10/1990 | Picard |
| 4,965,599 A | 10/1990 | Roddy et al. |
| 4,993,834 A | 2/1991 | Carlhoff et al. |
| 4,998,972 A | 3/1991 | Chin et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,085,496 A | 2/1992 | Yoshida et al. |
| 5,120,953 A | 6/1992 | Harris |
| 5,121,983 A | 6/1992 | Lee |
| 5,127,730 A | 7/1992 | Brelje et al. |
| 5,197,470 A | 3/1993 | Helfer et al. |
| 5,202,745 A | 4/1993 | Sorin et al. |
| 5,212,667 A | 5/1993 | Tomlinson et al. |
| 5,214,538 A | 5/1993 | Lobb |
| 5,228,001 A | 7/1993 | Birge et al. |
| 5,241,364 A | 8/1993 | Kimura et al. |
| 5,248,876 A | 9/1993 | Kerstens et al. |
| 5,262,644 A | 11/1993 | Maguire |
| 5,291,885 A | 3/1994 | Taniji et al. |
| 5,293,872 A | 3/1994 | Alfano et al. |
| 5,293,873 A | 3/1994 | Fang |
| 5,304,810 A | 4/1994 | Amos |
| 5,305,759 A | 4/1994 | Kaneko et al. |
| 5,317,389 A | 5/1994 | Hochberg et al. |
| 5,318,024 A | 6/1994 | Kittrell et al. |
| 5,321,501 A | 6/1994 | Swanson et al. |
| 5,353,790 A | 10/1994 | Jacques et al. |
| 5,383,467 A | 1/1995 | Auer et al. |
| 5,411,016 A | 5/1995 | Kume et al. |
| 5,419,323 A | 5/1995 | Kittrell et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,486,701 A | 1/1996 | Norton et al. |
| 5,491,524 A | 2/1996 | Hellmuth et al. |
| 5,491,552 A | 2/1996 | Knuttel |
| 5,526,338 A | 6/1996 | Hasman et al. |
| 5,562,100 A | 10/1996 | Kittrell et al. |
| 5,565,986 A | 10/1996 | Knüttel |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Gunderson et al. |
| 5,621,830 A | 4/1997 | Lucey et al. |
| 5,623,336 A | 4/1997 | Raab et al. |
| 5,635,830 A | 6/1997 | Itoh |
| 5,649,924 A | 7/1997 | Everett et al. |
| 5,697,373 A | 12/1997 | Richards-Kortum et al. |
| 5,698,397 A | 12/1997 | Zarling et al. |
| 5,710,630 A | 1/1998 | Essenpreis et al. |
| 5,716,324 A | 2/1998 | Toida |
| 5,719,399 A | 2/1998 | Alfano et al. |
| 5,730,731 A | 3/1998 | Mollenauer et al. |
| 5,735,276 A | 4/1998 | Lemelson |
| 5,740,808 A | 4/1998 | Panescu et al. |
| 5,748,318 A | 5/1998 | Maris et al. |
| 5,748,598 A | 5/1998 | Swanson et al. |
| 5,784,352 A | 7/1998 | Swanson et al. |
| 5,785,651 A | 7/1998 | Kuhn et al. |
| 5,795,295 A | 8/1998 | Hellmuth et al. |
| 5,801,826 A | 9/1998 | Williams |
| 5,803,082 A | 9/1998 | Stapleton et al. |
| 5,807,261 A | 9/1998 | Benaron et al. |
| 5,817,144 A | 10/1998 | Gregory |
| 5,840,023 A | 11/1998 | Oraevsky et al. |
| 5,840,075 A | 11/1998 | Mueller et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |
| 5,847,827 A | 12/1998 | Fercher |
| 5,862,273 A | 1/1999 | Pelletier |
| 5,865,754 A | 2/1999 | Sevick-Muraca et al. |
| 5,867,268 A | 2/1999 | Gelikonov et al. |
| 5,871,449 A | 2/1999 | Brown |
| 5,872,879 A | 2/1999 | Hamm |
| 5,877,856 A | 3/1999 | Fercher |
| 5,887,009 A | 3/1999 | Mandella et al. |
| 5,892,583 A | 4/1999 | Li |
| 5,910,839 A | 6/1999 | Erskine et al. |
| 5,912,764 A | 6/1999 | Togino |
| 5,920,373 A | 7/1999 | Bille |
| 5,920,390 A | 7/1999 | Farahi et al. |
| 5,921,926 A | 7/1999 | Rolland et al. |
| 5,926,592 A | 7/1999 | Harris et al. |
| 5,949,929 A | 9/1999 | Hamm |
| 5,951,482 A | 9/1999 | Winston et al. |
| 5,955,737 A | 9/1999 | Hallidy et al. |
| 5,956,355 A | 9/1999 | Swanson et al. |
| 5,968,064 A | 10/1999 | Selmon et al. |
| 5,975,697 A | 11/1999 | Podoleanu et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 6,002,480 A | 12/1999 | Izatt et al. |
| 6,004,314 A | 12/1999 | Wei et al. |
| 6,006,128 A | 12/1999 | Izatt et al. |
| 6,010,449 A | 1/2000 | Selmon et al. |
| 6,014,214 A | 1/2000 | Li |
| 6,020,963 A | 2/2000 | DiMarzio |
| 6,033,721 A | 3/2000 | Nassuphis |
| 6,044,288 A | 3/2000 | Wake et al. |
| 6,045,511 A | 4/2000 | Ott et al. |
| 6,048,742 A | 4/2000 | Weyburne et al. |
| 6,053,613 A | 4/2000 | Wei et al. |
| 6,069,698 A | 5/2000 | Ozawa et al. |
| 6,091,496 A | 7/2000 | Hill |
| 6,091,984 A | 7/2000 | Perelman et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,134,033 A | 10/2000 | Bergano et al. |
| 6,141,577 A | 10/2000 | Rolland et al. |

| | | | | | | |
|---|---|---|---|---|---|---|
| 6,151,522 | A | 11/2000 | Alfano et al. | 7,190,464 B2 | 3/2007 | Alphonse |
| 6,159,445 | A | 12/2000 | Klaveness et al. | 7,231,243 B2 | 6/2007 | Tearney et al. |
| 6,160,826 | A | 12/2000 | Swanson et al. | 7,242,480 B2 | 7/2007 | Alphonse |
| 6,161,031 | A | 12/2000 | Hochman et al. | 7,267,494 B2 | 9/2007 | Deng et al. |
| 6,166,373 | A | 12/2000 | Mao | 7,355,716 B2 | 4/2008 | De Boer et al. |
| 6,174,291 | B1 | 1/2001 | McMahon et al. | 7,359,062 B2 | 4/2008 | Chen et al. |
| 6,175,669 | B1 | 1/2001 | Colston et al. | 7,366,376 B2 | 4/2008 | Shishkov et al. |
| 6,185,271 | B1 | 2/2001 | Kinsinger | 7,391,520 B2 | 6/2008 | Zhou et al. |
| 6,191,862 | B1 | 2/2001 | Swanson et al. | 2001/0047137 A1 | 11/2001 | Moreno et al. |
| 6,193,676 | B1 | 2/2001 | Winston et al. | 2002/0016533 A1 | 2/2002 | Marchitto et al. |
| 6,198,956 | B1 | 3/2001 | Dunne | 2002/0048025 A1* | 4/2002 | Takaoka ..................... 356/497 |
| 6,201,989 | B1 | 3/2001 | Whitehead et al. | 2002/0064341 A1 | 5/2002 | Fauver et al. |
| 6,208,415 | B1 | 3/2001 | De Boer et al. | 2002/0076152 A1 | 6/2002 | Hughes et al. |
| 6,208,887 | B1 | 3/2001 | Clarke | 2002/0085209 A1 | 7/2002 | Mittleman et al. |
| 6,245,026 | B1 | 6/2001 | Campbell et al. | 2002/0093662 A1 | 7/2002 | Chen et al. |
| 6,249,349 | B1 | 6/2001 | Lauer | 2002/0122246 A1* | 9/2002 | Tearney et al. .............. 359/368 |
| 6,263,234 | B1 | 7/2001 | Engelhardt et al. | 2002/0140942 A1 | 10/2002 | Fee et al. |
| 6,264,610 | B1 | 7/2001 | Zhu | 2002/0158211 A1 | 10/2002 | Gillispie |
| 6,272,376 | B1 | 8/2001 | Marcu et al. | 2002/0161357 A1 | 10/2002 | Anderson et al. |
| 6,274,871 | B1 | 8/2001 | Dukor et al. | 2002/0163622 A1 | 11/2002 | Magnin et al. |
| 6,282,011 | B1 | 8/2001 | Tearney et al. | 2002/0172485 A1 | 11/2002 | Keaton et al. |
| 6,297,018 | B1 | 10/2001 | French et al. | 2002/0183623 A1 | 12/2002 | Tang et al. |
| 6,308,092 | B1 | 10/2001 | Hoyns | 2002/0188204 A1 | 12/2002 | McNamara et al. |
| 6,324,419 | B1 | 11/2001 | Guzelsu et al. | 2002/0196446 A1 | 12/2002 | Roth et al. |
| 6,341,036 | B1 | 1/2002 | Tearney et al. | 2002/0198457 A1 | 12/2002 | Tearney et al. |
| 6,353,693 | B1 | 3/2002 | Kano et al. | 2003/0023153 A1 | 1/2003 | Izatt et al. |
| 6,359,692 | B1 | 3/2002 | Groot | 2003/0026735 A1 | 2/2003 | Nolte et al. |
| 6,377,349 | B1 | 4/2002 | Fercher | 2003/0028114 A1 | 2/2003 | Casscells, III |
| 6,384,915 | B1 | 5/2002 | Everett et al. | 2003/0097048 A1 | 5/2003 | Ryan |
| 6,393,312 | B1 | 5/2002 | Hoyns | 2003/0108911 A1 | 6/2003 | Klimant et al. |
| 6,394,964 | B1 | 5/2002 | Sievert, Jr. et al. | 2003/0135101 A1 | 7/2003 | Webler |
| 6,396,941 | B1 | 5/2002 | Bacus et al. | 2003/0164952 A1 | 9/2003 | Deichmann et al. |
| 6,421,164 | B2 | 7/2002 | Tearney et al. | 2003/0171691 A1 | 9/2003 | Casscells, III et al. |
| 6,445,485 | B1 | 9/2002 | Frigo et al. | 2003/0199769 A1 | 10/2003 | Podoleanu et al. |
| 6,445,944 | B1 | 9/2002 | Ostrovsky | 2003/0216719 A1 | 11/2003 | Debenedictis et al. |
| 6,459,487 | B1 | 10/2002 | Chen et al. | 2003/0220749 A1 | 11/2003 | Chen et al. |
| 6,463,313 | B1 | 10/2002 | Winston et al. | 2003/0236443 A1 | 12/2003 | Cespedes et al. |
| 6,469,846 | B2 | 10/2002 | Ebizuka et al. | 2004/0054268 A1 | 3/2004 | Esenaliev et al. |
| 6,475,159 | B1 | 11/2002 | Casscells et al. | 2004/0072200 A1 | 4/2004 | Rigler et al. |
| 6,475,210 | B1 | 11/2002 | Phelps et al. | 2004/0077949 A1 | 4/2004 | Blofgett et al. |
| 6,485,413 | B1 | 11/2002 | Boppart et al. | 2004/0086245 A1 | 5/2004 | Farroni et al. |
| 6,485,482 | B1 | 11/2002 | Belef | 2004/0100631 A1 | 5/2004 | Bashkansky et al. |
| 6,501,551 | B1 | 12/2002 | Tearney et al. | 2004/0100681 A1 | 5/2004 | Bjarklev et al. |
| 6,501,878 | B2 | 12/2002 | Hughes et al. | 2004/0126048 A1 | 7/2004 | Dave et al. |
| 6,538,817 | B1 | 3/2003 | Farmer et al. | 2004/0133191 A1 | 7/2004 | Momiuchi et al. |
| 6,549,801 | B1 | 4/2003 | Chen et al. | 2004/0150829 A1 | 8/2004 | Koch et al. |
| 6,552,796 | B2 | 4/2003 | Magnin et al. | 2004/0152989 A1 | 8/2004 | Puttappa et al. |
| 6,556,305 | B1 | 4/2003 | Aziz et al. | 2004/0166593 A1 | 8/2004 | Nolte et al. |
| 6,556,853 | B1 | 4/2003 | Cabib et al. | 2004/0212808 A1 | 10/2004 | Okawa et al. |
| 6,558,324 | B1 | 5/2003 | Von Behren et al. | 2004/0239938 A1 | 12/2004 | Izatt |
| 6,564,087 | B1 | 5/2003 | Pitris et al. | 2004/0263843 A1 | 12/2004 | Knopp et al. |
| 6,564,089 | B2 | 5/2003 | Izatt et al. | 2005/0018201 A1 | 1/2005 | De Boer |
| 6,567,585 | B2 | 5/2003 | Harris | 2005/0035295 A1 | 2/2005 | Bouma et al. |
| 6,615,071 | B1 | 9/2003 | Casscells, III et al. | 2005/0046837 A1 | 3/2005 | Izumi et al. |
| 6,622,732 | B2 | 9/2003 | Constantz | 2005/0075547 A1 | 4/2005 | Wang |
| 6,680,780 | B1 | 1/2004 | Fee | 2005/0083534 A1 | 4/2005 | Riza et al. |
| 6,685,885 | B2 | 2/2004 | Nolte et al. | 2005/0171438 A1 | 8/2005 | Chen et al. |
| 6,687,007 | B1 | 2/2004 | Meigs | 2006/0103850 A1 | 5/2006 | Alphonse et al. |
| 6,687,010 | B1 | 2/2004 | Horii et al. | 2006/0146339 A1 | 7/2006 | Fujita et al. |
| 6,687,036 | B2 | 2/2004 | Riza | 2006/0155193 A1 | 7/2006 | Leonardi et al. |
| 6,701,181 | B2 | 3/2004 | Tang et al. | 2006/0244973 A1 | 11/2006 | Yun et al. |
| 6,738,144 | B1 | 5/2004 | Dogariu et al. | 2007/0019208 A1 | 1/2007 | Toida et al. |
| 6,741,355 | B2 | 5/2004 | Drabarek | 2007/0070496 A1 | 3/2007 | Gweon et al. |
| 6,790,175 | B1 | 9/2004 | Furusawa et al. | 2007/0291277 A1 | 12/2007 | Everett et al. |
| 6,806,963 | B1 | 10/2004 | Wälti et al. | | | |
| 6,816,743 | B2 | 11/2004 | Moreno et al. | | | |
| 6,839,496 | B1 | 1/2005 | Mills et al. | | FOREIGN PATENT DOCUMENTS | |
| 6,903,820 | B2 | 6/2005 | Wang | DE | 4309056 | 9/1994 |
| 6,949,072 | B2 | 9/2005 | Furnish et al. | DE | 19542955 | 5/1997 |
| 6,980,299 | B1 | 12/2005 | de Boer | DE | 10351319 | 6/2005 |
| 7,006,231 | B2 | 2/2006 | Ostrovsky et al. | EP | 0110201 | 6/1984 |
| 7,019,838 | B2* | 3/2006 | Izatt et al. ................... 356/479 | EP | 0251062 | 1/1988 |
| 7,061,622 | B2 | 6/2006 | Rollins et al. | EP | 0617286 | 2/1994 |

| | | |
|---|---|---|
| EP | 0590268 | 4/1994 |
| EP | 0728440 | 8/1996 |
| EP | 0933096 | 8/1999 |
| EP | 1324051 | 7/2003 |
| EP | 1426799 | 6/2004 |
| FR | 2738343 | 8/1995 |
| GB | 1257778 | 12/1971 |
| GB | 2030313 | 4/1980 |
| GB | 2209221 | 5/1989 |
| JP | 6073405 | 4/1985 |
| JP | 4135550 | 5/1992 |
| JP | 4135551 | 5/1992 |
| JP | 5509417 | 11/1993 |
| JP | 5509417 | 12/1993 |
| JP | 6073405 | 3/1994 |
| JP | 2738343 | 1/1996 |
| WO | 7900841 | 10/1979 |
| WO | 9201966 | 2/1992 |
| WO | 9216865 | 10/1992 |
| WO | 9219930 | 11/1992 |
| WO | 9303672 | 3/1993 |
| WO | 9216865 | 10/1993 |
| WO | 9533971 | 12/1995 |
| WO | 9628212 | 9/1996 |
| WO | 9732182 | 9/1997 |
| WO | 9800057 | 1/1998 |
| WO | 9801074 | 1/1998 |
| WO | 9814132 | 4/1998 |
| WO | 9835203 | 8/1998 |
| WO | 9838907 | 9/1998 |
| WO | 9846123 | 10/1998 |
| WO | 98/48846 | 11/1998 |
| WO | 9848838 | 11/1998 |
| WO | 9905487 | 2/1999 |
| WO | 9944089 | 9/1999 |
| WO | 9957507 | 11/1999 |
| WO | 0058766 | 10/2000 |
| WO | 0108579 | 2/2001 |
| WO | 01/27679 | 4/2001 |
| WO | 0138820 | 5/2001 |
| WO | 0142735 | 6/2001 |
| WO | 2004105598 | 12/2001 |
| WO | 0236015 | 5/2002 |
| WO | 0238040 | 5/2002 |
| WO | 02054027 | 7/2002 |
| WO | 02/084263 | 10/2002 |
| WO | 03020119 | 3/2003 |
| WO | 03/046636 | 6/2003 |
| WO | 03052478 | 6/2003 |
| WO | 03062802 | 7/2003 |
| WO | 03/105678 | 12/2003 |
| WO | 2004/057266 | 7/2004 |
| WO | 2004066824 | 8/2004 |
| WO | 2004/088361 | 10/2004 |
| WO | 2005000115 | 1/2005 |
| WO | 2005/054780 | 6/2005 |
| WO | 2006/004743 | 1/2006 |
| WO | 2006/014392 | 2/2006 |
| WO | 2006/039091 | 4/2006 |
| WO | 2006/059109 | 6/2006 |
| WO | 2006/130797 | 12/2006 |
| WO | 2007/028531 | 3/2007 |
| WO | 2007/038787 | 4/2007 |
| WO | 2007/083138 | 7/2007 |

OTHER PUBLICATIONS

Office Action mailed Oct. 1, 2008 for U.S. Appl. No. 11/955,986.
Invitation of Pay Additional Fees mailed Aug. 7, 2008 for International Application No. PCT/US2008/062354.
Invitation of Pay Additional Fees mailed Jul. 20, 2008 for International Application No. PCT/US2007/081982.
International Search Report and Written Opinion mailed Mar. 7, 2006 for PCT/US2005/035711.
International Search Report and Written Opinion mailed Jul. 18, 2008 for PCT/US2008/057533.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
International Search Report and Written Opinion mailed Jul. 4, 2008 for PCT/US2008/051432.
Jonathan, Enock (2005) "Dual Reference Arm Low-Coherence Interferometer-Based Reflectometer For Optical Coherence Tomography (OCT) Application" *Optics Communications* vol. 252.
Motaghian Nezam, S.M.R. (2007) "increased Ranging Depth in optical Frequency Domain Imaging by Frequency Encoding" *Optics Letters*, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Australian Examiner's Report mailed May 27, 2008 for Australian patent application No. 2003210669.
Notice of Allowance mailed Jun. 4, 2008 for U.S. Appl. No. 11/174,425.
European communication dated May 15, 2008 for European patent application No. 05819917.5.
International Search Report and Written Opinion mailed Jun. 10, 2008 for PCT/US2008/051335.
Oh. W.Y. et al (2006) "Ultrahigh-Speed Optical Frequency Domain Imaging and Application to laser Ablation Monitoring" *Applied Physics Letters*, vol. 88.
Office Action dated Aug. 21, 2008 for U.S. Appl. No. 11/505,700.
Sticker, Markus (2002) En Face Imaging of Single Cell layers by Differential Phase-Contrast Optical Coherence Microscopy) *Optics Letters*, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007, "Abstracts of the 19th Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion mailed Mar. 14, 2005 for PCT/US2004/018045.
Notification of the international Preliminary Report on Patentability mailed Oct. 21, 2005.
Shim M.G. et al., "Study of Fiber-Optic Probes for In vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.

Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Search Report and Written Opinion dated Mar. 23, 2006 for PCT/US2005/042408.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
International Search Report and Written Opinion dated Feb. 2, 2009 for International Application No. PCT/US2008/071786.
Bilenca A et al: "The Role of Amplitude and phase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection mailed Dec. 2, 2008 for Japanese patent application No. 2000-533782.
Office Action dated Dec. 6, 2006 for U.S. Appl. No. 10/997,789.
Elliott, K. H. "The use of commercial CCD cameras as linear detectors in the physics undergraduate teaching laboratory", European Journal of Physics 19, 1998, pp. 107-117.
Lauer, V. "New approach to optical diffraction tomography yielding a vector equation of diffraction tomography and a novel tomographic microscope", Journal of Microscopy vol. 205, Issue 2, 2002, pp. 165-176.
Yu, P. et al. "Imaging of tumor necroses using full-frame optical coherence imaging", Proceedings of SPIE vol. 4956, 2003, pp. 34-41.
Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.
Office Action dated Dec. 18, 2006 for U.S. Appl. No. 10/501,276.
Devesa, Susan S. et al. (1998) "Changing Patterns in the Incidence of Esophegeal and Gastric Carcinoma in the United States." *American Cancer Society* vol. 83, No. 10 pp. 2049-2053.
Barr, H et al. (2005) "Endoscopic Therapy for Barrett's Oesophaugs" *Gut* vol. 54:875-884.
Johnston, Mark H.(2005) "Technology Insight: Ablative Techniques for Barrett's Esophagus—Current and Emerging Trends" www.Nature.com/clinicalpractice/gasthep.
Falk, Gary W. et al. (1997) "Surveillance of Patients with Barrett's Esophagus for Dysplasia and Cancer with Ballon Cytology" *Gastrorenterology* vol. 112, pp. 1787-1797.
Sepchler, Stuart Jon. (1997) "Barrett's Esophagus: Should We Brush off this Balloning Problem?" *Gastroenterology* vol. 112, pp. 2138-2152.
Froehly, J. et al. (2003) "Multiplexed 3D Imaging Using Wavelength Encoded Spectral Interferometry: A Proof of Principle" *Optics Communications* vol. 222, pp. 127-136.
Kubba A.K. et al. (1999) "Role of p53 Assessment in Management of Barrett's Esophagus" *Digestive Disease and Sciences* vol. 44, No. 4. pp. 659-667.
Reid, Brian J. (2001) "p53 and Neoplastic Progression in Barrett's Esophagus" *The American Journal of Gastroenterology* vol. 96, No. 5, pp. 1321-1323.
Sharma, P. et al.(2003) "Magnification Chromoendoscopy for the Detection of Intestinal Metaplasia and Dysplasia in Barrett's Oesophagus" *Gut* vol. 52, pp. 24-27.

Kuipers E.J et al. (2005) "Diagnostic and Therapeutic Endoscopy" *Journal of Surgical Oncology* vol. 92, pp. 203-209.
Georgakoudi, Irene et al. (2001) "Fluorescence, Reflectance, and Light-Scattering Spectroscopy for Evaluating Dysplasia in Patients with Barrett's Esophagus" *Gastroenterology* vol. 120, pp. 1620-1629.
Adrain, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.
Canto, Marcia Irene et al (1999) "Vital Staining and Barrett's Esophagus" *Gastrointestinal Endoscopy* vol. 49, No. 3, part 2, pp. 12-16.
Evans, John A. et al. (2006) "Optical Coherence Tomography to Identify Intramucosal Carcinoma and High-Grade Dysplasia in Barrett's Esophagus" *Clinical Gastroenterology and Hepatology* vol. 4. pp. 38-3.
Poneros, John M. et al. (2001) "Diagnosis of Specialized Intestinal Metaplasia by Optical Coherence Tomography" *Gastroenterology* vol. 120, pp. 7-12.
Ho, W. Y. et al. (2005) "115 KHz Tuning Repetition Rate Ultrahigh-Speed Wavelength-Swept Semiconductor Laser" *Optics Letters* col. 30, No. 23, pp. 3159-3161.
Brown, Stanley B. et al. (2004) "The Present and Future Role of Photodynamic Therapy in Cancer Treatment" *The Lancet Oncology* vol. 5, pp. 497-508.
Boogert, Jolanda Van Den et al. (1999) "Endoscopic Ablation Therapy for Barrett's Esophagua with High-Grade Dysplasia: A Review" *The American Journal of Gastroenterology* vol. 94, No. 5, pp. 1153-1160.
Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.
Sampliner, Richard E. (2004) "Endoscopic Ablative Therapy for Barrett's Esophagus: Current Status" *Gastrointestinal Endoscopy* vol. 59, No. 1, pp. 66-69.
Soetikno, Roy M. et al. (2003) "Endoscopic Mucosal resection" *Gastrointestinal Endoscopy* vol. 57, No. 4, pp. 567-579.
Ganz, Robert A. et al. (2004) "Complete Ablation of Esophageal Epithelium with a Balloon-based Bipolar Electrode: A Phased Evaluation in the Porcine and in the Human Esophagus" *Gastrointestinal Endoscopy* vol. 60, No. 6, pp. 1002-1010.
Pfefer, Jorje at al. (2006) "Performance of the Aer-O-Scope, A Pneumatic, Self Propelling, Self Navigating Colonoscope in Animal Experiments" *Gastrointestinal Endoscopy* vol. 63, No. 5, pp. AB223.
Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.
Vogel, Alfred et al. (2003) "Mechanisms of Pulsed Laser Ablation of Biological Tissues" *American Chemical Society* vol. 103, pp. 577-644.
McKenzie, A. L. (1990) "Physics of Thermal Processes in Laser-Tissue Interaction" *Phys. Med. Biol* vol. 35, No. 9, pp. 1175-1209
Anderson, R. Rox et al. (1983) "Selective Photothermolysis" Precise Microsurgery Absorption of Pulsed Radiation *Science* vol. 220, No. 4596, pp. 524-527 by Selective.
Jacques, Steven L. (1993) "Role of Tissue Optics and Pulse Duration on Tissue Effects During High-Power Laser Irradiation" *Applied Optics* vol. 32, No. 13, pp. 2447-2454.
Nahen, Kester et al. (1999) "Investigations on Acoustic On-Line Monitoring of IR Laser Ablation of burned Skin" *Lasers in Surgery and Medicine* vol. 25, pp. 69-78.
Jerath, Maya R. et al. (1993) "Calibrated Real-Time Control of Lesion Size Based on Reflectance Images" *Applied Optics* vol. 32, No. 7, pp. 1200-1209.
Jerath, Maya R. et al (1992) "Dynamic Optical Property Changes: Implications for Reflectance Feedback Control of Photocoagulation" *Journal of Photochemical,.Photobiology. B: Biol* vol. 16, pp. 113-126.
Deckelbaum, Lawrence I. (1994) "Coronary Lasers Angioplasty" *Lasers in Surgery and Medicine* vol. 14, pp. 101-110.
Kim, B.M. et al. (1998) "Optical Feedback Signal for Ultrashort Laser Pulse Ablation of Tissue" *Applied Surface Science* vol. 127-129, pp. 857-862.

Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.

Whelan, W.M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.

Thomsen, Sharon et al. (1990) "Microscopic Correlates of Macroscopic Optical Property Changes During Thermal Coagulation of Myocardium" *SPIE* vol. 1202, pp. 2-11.

Khan, Misban Huzaira et al. (2005) "Intradermally Focused Infrared Laser Pulses: Thermal Effects at Defined Tissue Depths" *Lasers in Surgery and Medicine* vol. 36, pp. 270-280.

Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.

Nadkarni, Seemantini K. et al (2005) "Charaterization of Atherosclerotic Plaques by Laser Speckle Imaging" *Circulation* vol. 112, pp. 885-892.

Zimnyakov, Dmitry A. et al (2002) "Speckle-Contrast Monitoring of Tissue Thermal Modification" *Applied Optics* vol. 41, No. 28, pp. 5989-5996.

Morelli, J.G., et al (1986) "Tunable Dye Laser (577 nm) Treatment of Port Wine Stains" *Lasers in Surgery and Medicine* vol. 6, pp. 94-99.

French, P.M.W. et al. (1993) "Continuous-wave Mode-Locked $Cr^{4+}$: YAG Laser" *Optics Letters* vol. 18, No. 1, pp. 39-41.

Sennaroglu, Alphan at al. (1995) "Efficient Continuous-Wave Chromium-Doped YAG Laser" *Journal of Optical Society of America* vol. 12, No. 5, pp. 930-937.

Bouma, B et al. (1994) "Hybrid Mode Locking of a Flash-Lamp-Pumped Ti: $Al_2O_3$ Laser" *Optics Letters* vol. 19, No. 22, pp. 1858-1860.

Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.

Tang C. L. et al., "Wide-band electro-optical tuning of semiconductor lasers", Applied Physics Letters, vol. 30, No. 2, Jan. 15, 1977, pp. 113-116.

Tang C. L. et al., "Transient effects in wavelength-modulated dye lasers", Applied Physics Letters, vol. 26, No. 9, May 1, 1975, pp. 534-537.

Telle M. John, et al., "Very rapid tuning of cw dye laser", Applied Physics Letters, vol. 26, No. 10, May 15, 1975, pp. 572-574.

Telle M. John, et al., "New method for electro-optical tuning of tunable lasers", Applied Physics Letters, vol. 24, No. 2, Jan. 15, 1974, pp. 85-87.

Schmitt M. Joseph et al. "OCT elastography: imaging microscopic deformation and strain of tissue", Optics Express, vol. 3, No. 6, Sep. 14, 1998, pp. 199-211.

M. Gualini Muddassir et al., "Recent Advancements of Optical Interferometry Applied to Medicine", IEEE Transactions on Medical Imaging, vol. 23, No. 2, Feb. 2004, pp. 205-212.

Maurice L. Roch et al. "Noninvasive Vascular Elastography: Theoretical Framework", IEEE Transactions on Medical Imaging, vol. 23, No. 2, Feb. 2004, pp. 164-180.

Kirkpatrick J. Sean et al. "Optical Assessment of Tissue Mechanical Properties", Proceedings of the SPIE—The International Society for Optical Engineering SPIE—vol. 4001, 2000, pp. 92-101.

Lisauskas B. Jennifer et al., "Investigation of Plaque Biomechanics from Intravascular Ultrasound Images using Finite Element Modeling", Proceedings of the 19th International Conference—IEEE Oct. 30-Nov. 2, 1997, pp. 887-888.

Parker K. J. et al., "Techniques for Elastic Imaging: A Review", IEEE Engineering in Medicine and Biology, Nov./Dec. 1996, pp. 52-59.

Dubois Arnaud et al., "Ultrahigh-resolution OCT using white-light interference microscopy", Proceedings of SPIE, 2003, vol. 4956, pp. 14-21.

Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.

Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.
PCT International Search Report and Written Opinion for Application No. PCT/US2007/061463 dated Jan. 23, 2008.
PCT International Search Report and Written Opinion for Application No. PCT/US2007/061481 dated Mar. 17, 2008.
PCT International Search Report and Written Opinion for Application No. PCT/US2007/078254 dated Mar. 28, 2008.

Sadhwani, Ajay et al., "Determination of Teflon thickness with laser speckle I. Potential for burn depth diagnosis", Optical Society of America, 1996, vol. 35, No. 28, pp. 5727-5735.

C.J. Stewart et al., "A comparison of two laser-based methods for determination of burn scar perfusion: Laser Doppler versus laser speckle imaging", Elsevier Ltd., 2005, vol. 31, pp. 744-752.

G. J. Tearney et al., "Atherosclerotic plaque characterization by spatial and temporal speckle pattern analysis", CLEO 2001, vol. 56, pp. 307-307.

PCT International Search Report for Application No. PCT/US2007/068233 dated Feb. 21, 2008.
PCT International Search Report for Application No. PCT/US2007/060787 dated Mar. 18, 2008.
Statement under Article 19 and Reply to PCT Written Opinion for PCT International Application No. PCT/US2005/043951 dated Jun. 6, 2006.
PCT International Preliminary Report on Patentability for Application No. PCT/US2005/043951 dated Jun. 7, 2007.

Fujimoto et al., "High Resolution in Vivo Intra-Arterial Imaging with Optical Coherence Tomography," *Official Journal of the British Cardiac Society*, vol. 82, pp. 128-133 Heart, 1999.

D. Huang et al., "Optical Coherence Tomography," *Science*, vol. 254, pp. 1178-1181, Nov. 1991.

Tearney et al., "High-Speed Phase- and Group Delay Scanning with a Grating Based Phase Control Delay Line," *Optics Letters*, vol. 22, pp. 1811-1813, Dec. 1997.

Rollins, et al., "In Vivo Video Rate Optical Coherence Tomography," *Optics Express*, vol. 3, pp. 219-229, Sep. 1998.

Saxer, et al., High Speed Fiber-Based Polarization-Sensitive Optical Coherence Tomography of in Vivo Human Skin, *Optical Society of America*, vol. 25, pp. 1355-1357, Sep. 2000.

Oscar Eduardo Martinez, "3000 Times Grating Compress or with Positive Group Velocity Dispersion," *IEEE*, vol. QE-23, pp. 59-64, Jan. 1987.

Kulkarni, et al., "Image Enhancement in Optical Coherence Tomography Using Deconvolution," *Electronics Letters*, vol. 33, pp. 1365-1367, Jul. 1997.

Bashkansky, et al., "Signal Processing for Improving Field Cross-Correlation Function in Optical Coherence Tomography," *Optics & Photonics News*, vol. 9, pp. 8137-8138, May 1998.

Yung et al., "Phase-Domain Processing of Optical Coherence Tomography Images," *Journal of Biomedical Optics*, vol. 4, pp. 125-136, Jan. 1999.

Tearney, et al., "In Vivo Endoscopic Optical Biopsy with Optical Coherence Tomography," *Science*, vol. 276, Jun. 1997.

W. Drexler et al., "In Vivo Ultrahigh-Resolution Optical Coherence Tomography," *Optics Letters* vol. 24, pp. 1221-1223, Sep. 1999.

Nicusor V. Iftimia et al., "A Portable, Low Coherence Interferometry Based Instrument for Fine Needle Aspiration Biopsy Guidance," Accepted to Review of Scientific Instruments, 2005.

Abbas, G.L., V.W.S. Chan et al., "Local-Oscillator Excess-Noise Suppression for Homodyne and Heterodyne-Detection," *Optics Letters*, vol. 8, pp. 419-421, Aug. 1983 issue.

Agrawal, G.P., "Population Pulsations and Nondegenerate 4-Wave Mixing in Semiconductor-Lasers and Amplifiers," *Journal Of The Optical Society Of America B-Optical Physics*, vol. 5, pp. 147-159, Jan. 1998.

Andretzky, P. et al., "Optical Coherence Tomography by Spectral Radar: Improvement of Signal-to-Noise Ratio," *The International Society for Optical Engineering*, USA, vol. 3915, 2000.

Ballif, J. et al., "Rapid and Scalable Scans at 21 m/s in optical Low-Coherence Reflectometry," *Optics Letters*, vol. 22, pp. 757-759, Jun. 1997.

Barfuss H. et al., "Modified Optical Frequency-Domain Reflectometry with High Spatial-Resolution for Components of Integrated Optic Systems," *Journal Of Lightwave Technology*, vol. 7, pp. 3-10, Jan. 1989.

Beaud, P. et al., "Optical Reflectometry with Micrometer Resolution for the Investigation of Integrated Optical-Devices," *Leee Journal of Quantum Electronics*, vol. 25, pp. 755-759, Apr. 1989.

Bouma, Brett et al., "Power-Efficient Nonreciprocal Interferometer and Linear-Scanning Fiber-Optic Catheter for Optical Coherence Tomography," *Optics Letters*, vol. 24, pp. 531-533, Apr. 1999.

Brinkmeyer, E. et al., "Efficient Algorithm for Non-Equidistant Interpolation of Sampled Data," *Electronics Letters*, vol. 28, p. 693, Mar. 1992.

Brinkmeyer, E. et al., "High-Resolution OCDR in Dispersive Wave-Guides," *Electronics Letters*, vol. 26, pp. 413-414, Mar. 1990.

Chinn, S.R. et al., "Optical Coherence Tomography Using a Frequency-Tunable Optical Source," *Optics Letters*, vol. 22, pp. 340-342, Mar. 1997.

Danielson, B.L. et al., "Absolute Optical Ranging Using Low Coherence Interferometry," *Applied Optics*, vol. 30, p. 2975, Jul. 1991.

Dorrer, C. et al., "Spectral Resolution and Sampling Issues in Fourier-Transform Spectral Interferometry," *Journal of the Optical Society of America B-Optical Physics*, vol. 17, pp. 1795-1802, Oct. 2000.

Dudley, J.M. et al., "Cross-Correlation Frequency Resolved Optical Gating Analysis of Broadband Continuum Generation in Photonic Crystal Fiber: Simulations and Experiments," *Optics Express*, vol. 10, p. 1215, Oct. 2002.

Eickhoff, W. et al., "Optical Frequency-Domain Reflectometry in Single-Mode Fiber," *Applied Physics Letters*, vol. 39, pp. 693-695, 1981.

Fercher, Adolf "Optical Coherence Tomography," *Journal of Biomedical Optics*, vol. 1, pp. 157-173, Apr. 1996.

Ferreira, L.A. et al., "Polarization-Insensitive Fiberoptic White-Light Interferometry," *Optics Communications*, vol. 114, pp. 386-392, Feb. 1995.

Fujii, Yohji, "High-Isolation Polarization-Independent Optical Circulator", *Journal of Lightwave Technology*, vol. 9, pp. 1239-1243, Oct. 1991.

Glance, B., "Polarization Independent Coherent Optical Receiver," *Journal of Lightwave Technology*, vol. LT-5, p. 274, Feb. 1987.

Glombitza, U., "Coherent Frequency-Domain Reflectometry for Characterization of Single-Mode Integrated-Optical Wave-Guides," *Journal of Lightwave Technology*, vol. 11, pp. 1377-1384, Aug. 1993.

Golubovic, B. et al., "Optical Frequency-Domain Reflectometry Using Rapid Wavelength Tuning of a Cr4+:Forsterite Laser," *Optics Letters*, vol. 11, pp. 1704-1706, Nov. 1997.

Haberland, U. H. P. et al., "Chirp Optical Coherence Tomography of Layered Scattering Media," *Journal of Biomedical Optics*, vol. 3, pp. 259-266, Jul. 1998.

Hammer, Daniel X. et al., "Spectrally Resolved White-Light Interferometry for Measurement of Ocular Dispersion," *Journal of the Optical Society of America A-Optics Image Science and Vision*, vol. 16, pp. 2092-2102, Sep. 1999.

Harvey, K. C. et al., "External-Cavity Diode-Laser Using a Grazing-Incidence Diffraction Grating," *Optics Letters*, vol. 16, pp. 910-912, Jun. 1991.

Hausler, Gerd et al., "'Coherence Radar' and 'Spectral Radar' New Tools for Dermatological Diagnosis," *Journal of Biomedical Optics*, vol. 3, pp. 21-31, Jan. 1998.

Hee, Michael R. et al., "Polarization-Sensitive Low-Coherence Reflectometer for Birefringence Characterization and Ranging," *Journal of the Optical Society of America B (Optical Physics)*, vol. 9, p. 903-908, Jun. 1992.

Hotate Kazuo et al., "Optical Coherence Domain Reflectometry by Synthesis of Coherence Function," *Journal of Lightwave Technology*, vol. 11, pp. 1701-1710, Oct. 1993.

Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.

Ivanov, A. P. et al., "New Method for High-Range Resolution Measurements of Light Scattering in Optically Dense Inhomogeneous Media," *Optics Letters*, vol. 1, pp. 226-228, Dec. 1977.

Ivanov, A. P. et al., "Interferometric Study of the Spatial Structure of a Light-Scattering Medium," *Journal of Applied Spectroscopy*, vol. 28, pp. 518-525, 1978.

Kazovsky, L. G. et al., "Heterodyne Detection Through Rain, Snow, and Turbid Media: Effective Receiver Size at Optical Through Millimeter Wavelenghths," *Applied Optics*, vol. 22, pp. 706-710, Mar. 1983.

Kersey, A. D. et al., "Adaptive Polarization Diversity Receiver Configuration for Coherent Optical Fiber Communications," *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.

Larkin, Kieran G., "Efficient Nonlinear Algorithm for Envelope Detection in White Light Interferometry," *Journal of the Optical Society of America A-Optics Image Science and Vision*, vol. 13, pp. 832-843, Apr. 1996.

Leitgeb, R. et al., "Spectral measurement of Absorption by Spectroscopic Frequency-Domain Optical Coherence Tomography," *Optics Letters*, vol. 25, pp. 820-822, Jun. 2000.

Lexer, F. et al., "Wavelength-Tuning Interferometry of Intraocular Distances," *Applied Optics*, vol. 36, pp. 6548-6553, Sep. 1997.

Mitsui, Takahisa, "Dynamic Range of Optical Reflectometry with Spectral Interferometry," *Japanese Journal of Applied Physics Part 1-Regular Papers Short Notes & Review Papers*, vol. 38, pp. 6133-6137, 1999.

Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.

Okoshi, Takanori, "Polarization-State Control Schemes for Heterodyne or Homodyne Optical Fiber Communications," *Journal of Lightwave Technology*, vol. LT-3, pp. 1232-1237, Dec. 1995.

Passy, R. et al., "Experimental and Theoretical Investigations of Coherent OFDR with Semiconductor-Laser Sources," *Journal of Lightwave Technology*, vol. 12, pp. 1622-1630, Sep. 1994.

Podoleanu, Adrian G., "Unbalanced Versus Balanced Operation in an Optical Coherence Tomography System," *Applied Optics*, vol. 39, pp. 173-182, Jan. 2000.

Price, J. H. V. et al., "Tunable, Femtosecond Pulse Source Operating in the Range 1.06-1.33 mn m Based on an Yb3+-doped Holey Fiber Amplifier," *Journal of the Optical Society of America B-Optical Physics*, vol. 19, pp. 1286-1294, Jun. 2002.

Schmitt, J. M. et al, "Measurement of Optical-Properties of Biological Tissues By Low-Coherence Reflectometry," *Applied Optics*, vol. 32, pp. 6032-6042, Oct. 1993.

Silberberg, Y. et al., "Passive-Mode Locking of a Semiconductor Diode-Laser," *Optics Letters*, vol. 9, pp. 507-509, Nov. 1984.

Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.

Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.

Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.

Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.

Swanson, E. A. et al., "High-Speed Optical Coherence Domain Reflectometry," *Optics Letters*, vol. 17, pp. 151-153, Jan. 1992.

Takada, K. et al., "High-Resolution OFDR with Incorporated Fiberoptic Frequency Encoder," *IEEE Photonics Technology Letters*, vol. 4, pp. 1069-1072, Sep. 1992.

Takada, Kazumasa et al., "Narrow-Band light Source with Acoustooptic Tunable Filter for Optical Low-Coherence Reflectometry," *IEEE Photonics Technology Letters*, vol. 8, pp. 658-660, May 1996.

Takada, Kazumasa et al., "New Measurement System for Fault Location in Optical Wave-Guide Devices Based on an Interometric-Technique," *Applied Optics*, vol. 26, pp. 1603-1606, May 1987.

Tateda, Mitsuhiro et al., "Interferometric Method for Chromatic Dispersion Measurement in a Single-Mode Optical Fiber," *IEEE Journal Of Quantum Electronics*, vol. 17, pp. 404-407, Mar. 1981.

Toide, M. et al., "Two-Dimensional Coherent Detection Imaging in Multiple Scattering Media Based the Directional Resolution Capability of the Optical Heterodyne Method," *Applied Physics B (Photophysics and Laser Chemistry)*, vol. B52, pp. 391-394, 1991.

Trutna, W. R. et al., "Continuously Tuned External-Cavity Semiconductor-Laser," *Journal of Lightwave Technology*, vol. 11, pp. 1279-1286, Aug. 1993.

Uttam, Deepak et al., "Precision Time Domain Reflectometry in Optical Fiber Systems Using a Frequency Modulated Continuous Wave Ranging Technique," *Journal of Lightwave Technology*, vol. 3, pp. 971-977, Oct. 1985.

Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.

Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.

Youngquist, Robert C. et al., "Optical Coherence-Domain Reflectometry—A New Optical Evaluation Technique," *Optics Letters*, vol. 12, pp. 158-160, Mar. 1987.

Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 3, pp. 1087-1096, Aug. 1997.

Yun, S. H. et al., "Interrogation of Fiber Grating Sensor Arrays with a Wavelength-Swept Fiber Laser," *Optics Letters*, vol. 23, pp. 843-845, Jun. 1998.

Yung, K. M., "Phase-Domain Processing of Optical Coherence Tomography Images," *Journal of Biomedical Optics*, vol. 4, pp. 125-136, Jan. 1999.

Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.

Zorabedian, Paul et al., "Tuning Fidelity of Acoustooptically Controlled External Cavity Semiconductor-Lasers," *Journal of Lightwave Technology*, vol. 13, pp. 62-66, Jan. 1995.

Victor S. Y. Lin et al., "A Porous Silicon-Based Optical Interferometric Biosensor," *Science Magazine*, vol. 278, pp. 840-843, Oct. 31, 1997.

De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.

Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.

Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.

Roth, Jonathan E. et al., "Simplified Method for Polarization-Sensitive Optical Coherence Tomography," *Optics Letters*, vol. 26, No. 14, Jul. 15, 2001, pp. 1069-1071.

Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.

Wong, Brian J.F. et al., "Optical Coherence Tomography of the Rat Cochlea," Journal of *Biomedical Optics*, vol. 5, No. 4, Oct. 2000, pp. 367-370.

Yao, Gang et al., "Propagation of Polarized Light in Turbid Media: Simulated Animation Sequences," *Optics Express*, vol. 7, No. 5, Aug. 28, 2000, pp. 198-203.

Wang, Xiao-Jun et al., "Characterization of Dentin and Enamel by Use of Optical Coherence Tomography," *Applied Optics*, vol. 38, No. 10, Apr. 1, 1999, pp. 2092-2096.

De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.

Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.

Groner, Warren et al., "Orthogonal Polarization Spectral Imaging: A New Method for Study of the Microcirculation," *Nature Medicine Inc.*, vol. 5, No. 10, Oct. 1999, pp. 1209-1213.

De Boer, Johannes F. et al., "Polarization Effects in Optical Coherence Tomography of Various Viological Tissues," *IEEE Journal of Selected Topics in Ouantum Electronics*, vol. 5, No. 4, Jul./Aug. 1999, pp. 1200-1204.

Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.

Lu, Shih-Yau et al., "Homogeneous and Inhomogeneous Jones Matrices," *J. Opt. Soc. Am. A.*, vol. 11, No. 2, Feb. 1994, pp. 766-773.

Bickel, S. William et al., "Stokes Vectors, Mueller Matrices, and Polarized Scattered Light," *Am. J. Phys.*, vol. 53, No. 5, May 1985 pp. 468-478.

Bréhonnet, F. Le Roy et al., "Optical Media and Target Characterization by Mueller Matrix Decomposition," *J. Phys. D: Appl. Phys.* 29, 1996, pp. 34-38.

Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.

Everett, M.J. et al., "Birefringence Characterization of Biological Tissue by Use of Optical Coherence Tomography," *Optics Letters*, vol. 23, No. 3, Feb. 1, 1998, pp. 228-230.

Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.

Barakat, Richard, "Statistics of the Stokes Parameters," *J. Opt. Soc. Am. B.*, vol. 4, No. 7, Jul. 1987, pp. 1256-1263.

Schmitt, J.M. et al., "Cross-Polarized Backscatter in Optical Coherence Tomography of Biological Tissue," *Optics Letters*, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.

Pierce, Mark C. et al., "Simultaneous Intensity, Birefringence and Flow Measurements with High-Speed Fiber-Based Optical Coherence Tomography," *Optics Letters*, vol. 27, No. 17, Sep. 1, 2002, pp. 1534-1536.

De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.

Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.

Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.

Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.

Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.

Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.

Tripathi, Renu et al., "Spectral Shaping for Non-Gaussian Source Spectra in Optical Coherence Tomography," *Optics Letters*, vol. 27, No. 6, Mar. 15, 2002, pp. 406-408.

Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.

White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.

De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.

Jiao, Shuliang et al., "Optical-Fiber-Based Mueller Optical Coherence Tomography," *Optics Letters*, vol. 28, No. 14, Jul. 15, 2003, pp. 1206-1208.

Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.

Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.

Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.

Morgan, Stephen P. et al., "Surface-Reflection Elimination in Polarization Imaging of Superficial Tissue," *Optics Letters*, vol. 28, No. 2, Jan. 15, 2003, pp. 114-116.

Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.

Park, B. Hyle et al., "Real-Time Multi-Functional Optical Coherence Tomography," *Optics Express*, vol. 11, No. 7, Apr. 7, 2003, pp. 782-793.

Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.

Somervell, A.R.D. et al., "Direct Measurement of Fringe Amplitude and Phase Using a Heterodyne Interferometer Operating in Broadband Light," *Elsevier, Optics Communications*, Oct. 2003.

Stifter, D. et al., "Polarisation-Sensitive Optical Coherence Tomography for Material Characterisation and Strain-Field Mapping," Applied Physics A 76, Materials Science & Processing, Jan. 2003, pp. 947-951.

Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.

Yang, Ying et al., "Observations of Birefringence in Tissues from Optic-Fibre-Based Optical Coherence Tomography," *Measurement Science and Technology*, Nov. 2002, pp. 41-46.

Yun, S.H. et al., "High-Speed Optical Frequency-Domain Imaging," *Optics Express*, vol. 11, No. 22, Nov. 3, 2003, pp. 2953-2963.

Yun, S.H. et al., "High-Speed Spectral-Domain Optical Coherence Tomography at 1.3 μm Wavelength," *Optics Express*, vol. 11, No. 26, Dec. 29, 2003, pp. 3598-3604.

Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.

Pircher, Michael et al., "Three Dimensional Polarization Sensitive OCT of Human Skin In Vivo," 2004, *Optical Society of America*.

Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.

Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.

Huang, Xiang-Run et al.,"Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.

Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.

Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.

Nassif, N.A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.

Park, B. Hyle et al., "Comment on Optical-Fiber-Based Mueller Optical Coherence Tomography," *Optics Letters*, vol. 29, No. 24, Dec. 15, 2004, pp. 2873-2874.

Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.

Pierce, Mark C. et al., "Collagen Denaturation can be Quantified in Burned Human Skin Using Polarization-Sensitive Optical Coherence Tomography," *Elsevier, Burns*, 2004, pp. 511-517.

Pierce, Mark C. et al., "Advances in Optical Coference Tomography Imaging for Dermatology," *The Society for Investigative Dermatology, Inc.* 2004, pp. 458-463.

Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.

Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.

Pircher, Michael et al., "Imaging Of Polarization Properties of Human Retina in Vivo with Phase Resolved Transversal PS-OCT," *Optics Express*, vol. 12, No. 24, Nov. 29, 2004 pp. 5940-5951.

Pircher, Michael et al., "Transversal Phase Resolved Polarization Sensitive Optical Coherence Tomography," *Physics in Medicing & Biology*, 2004, pp. 1257-1263.

Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.

Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.

Todorović, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.

Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.

Acioli, L. H., M. Ulman, et al. (1991). "Femtosecond Temporal Encoding in Barium-Titanate." *Optics Letters* 16(24): 1984-1986.

Aigouy, L., A. Lahrech, et al. (1999). "Polarization effects in apertureless scanning near-field optical microscopy: an experimental study." *Optics Letters* 24(4): 187-189.

Akiba, M., K. P. Chan, et al. (2003). "Full-field optical coherence tomography by two-dimensional heterodyne detection with a pair of CCD cameras." *Optics Letters* 28(10): 816-818.

Akkin, T., D. P. Dave, et al. (2004). "Detection of neural activity using phase-sensitive optical low-coherence reflectometry." *Optics Express* 12(11): 2377-2386.

Akkin, T., D. P. Dave, et al. (2003). "Surface analysis using phase sensitive optical low coherence reflectometry." *Lasers in Surgery and Medicine*: 4-4.

Akkin, T., D. P. Dave, et al. (2003). "Imaging tissue response to electrical and photothermal stimulation with nanometer sensitivity." *Lasers in Surgery and Medicine* 33(4): 219-225.

Akkin, T., T. E. Milner, et al. (2002). "Phase-sensitive measurement of birefringence change as an indication of neural functionality and diseases." *Lasers in Surgery and Medicine*: 6-6.

Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.

Antcliff, R. J., T. J. ffytche, et al. (2000). "Optical coherence tomography of melanocytoma." *American Journal of Ophthalmology* 130(6): 845-7.

Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.

Anvari, B., T. E. Milner, et al. (1995). "Selective Cooling of Biological Tissues—Application for Thermally Mediated Therapeutic Procedures." *Physics in Medicine and Biology* 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.

Arend, O., M. Ruffer, et al. (2000). "Macular circulation in patients with diabetes mellitus with and without arterial hypertension." *British Journal of Ophthalmology* 84(12): 1392-1396.

Arimoto, H. and Y. Ohtsuka (1997). "Measurements of the complex degree of spectral coherence by use of a wave-front-folded interferometer." *Optics Letters* 22(13): 958-960.

Azzolini, C., F. Patelli, et al. (2001). "Correlation between optical coherence tomography data and biomicroscopic interpretation of idiopathic macular hole." *American Journal of Ophthalmology* 132(3): 348-55.

Baba, T., K. Ohno-Matsui, et al. (2002). "Optical coherence tomography of choroidal neovascularization in high myopia." *Acta Ophthalmoloqica Scandinavica* 80(1): 82-7.

Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.

Baney, D. M. and W. V. Sorin (1993). "Extended-Range Optical Low-Coherence Reflectometry Using a Recirculating Delay Technique." *Ieee Photonics Technology Letters* 5(9): 1109-1112.

Baney, D. M., B. Szafraniec, et al. (2002). "Coherent optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3): 159-161.

Barakat, R. (1993). "Analytic Proofs of the Arago-Fresnel Laws for the Interference of Polarized-Light." *Journal of the Optical Society of America a-Optics Image Science and Vision* 10(1): 180-185.

Barbastathis, G. and D. J. Brady (1999). "Multidimensional tomographic imaging using volume holography." *Proceedings of the Ieee* 87(12): 2098-2120.

Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.

Barsky, S. H., S. Rosen, et al. (1980). "Nature and Evolution of Port Wine Stains—Computer-Assisted Study." *Journal of Investigative Dermatology* 74(3): 154-157.

Barton, J. K., J. A. Izatt, et al. (1999). "Three-dimensional reconstruction of blood vessels from in vivo color Doppler optical coherence tomography images." *Dermatology* 198(4): 355-361.

Barton, J. K., A. Rollins, et al. (2001). "Photothermal coagulation of blood vessels: a comparison of high-speed optical coherence tomography and numerical modelling." *Physics in Medicine and Biology* 46.

Barton, J. K., A. J. Welch, et al. (1998). "Investigating pulsed dye laser-blood vessel interaction with color Doppler optical coherence tomography." *Optics Express* 3.

Bashkansky, M., M. D. Duncan, et al. (1997). "Subsurface defect detection in ceramics by high-speed high-resolution optical coherent tomography." *Optics Letters* 22 (1): 61-63.

Bashkansky, M. and J. Reintjes (2000). "Statistics and reduction of speckle in optical coherence tomography." *Optics Letters* 25(8): 545-547.

Baumgartner, A., S. Dichtl, et al. (2000). "Polarization-sensitive optical coherence tomography of dental structures." *Caries Research* 34(1): 59-69.

Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.

Baumgartner, A., C. K. Hitzenberger, et al. (1998). "Signal and resolution enhancements in dual beam optical coherence tomography of the human eye." *Journal of Biomedical Optics* 3(1): 45-54.

Beaurepaire, E., P. Gleyzes, et at. (1998). *Optical coherence microscopy for the in-depth study of biological structures: System based on a parallel detection scheme*, Proceedings of SPIE—The International Society for Optical Engineering.

Beaurepaire, E., L. Moreaux, et al. (1999). "Combined scanning optical coherence and two-photon-excited fluorescence microscopy." *Optics Letters* 24(14): 969-971.

Bechara, F. G., T. Gambichler, et al. (2004). "Histomorphologic correlation with routine histology and optical coherence tomography." *Skin Research and Technology* 10 (3): 169-173.

Bechmann, M., M. J. Thiel, et al. (2000). "Central corneal thickness determined with optical coherence tomography in various types of glaucoma. [see comments]." *British Journal of Ophthalmology* 84(11): 1233-7.

Bek, T. and M. Kandi (2000). "Quantitative anomaloscopy and optical coherence tomography scanning in central serous chorioretinopathy." *Acta Ophthalmologica Scandinavica* 78(6): 632-7.

Benoit, A. M., K. Naoun, et al. (2001). "Linear dichroism of the retinal nerve fiber layer expressed with Mueller matrices." *Applied Optics* 40(4): 565-569.

Bicout, D., C. Brosseau, et al. (1994). "Depolarization of Multiply Scattered Waves by Spherical Diffusers—Influence of the Size Parameter." *Physical Review* E 49(2): 1767-1770.

Blanchot, L., M. Lebec, et al. (1997). *Low-coherence in depth microscopy for biological tissues imaging: Design of a real time control system*. Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

Blumenthal, E. Z., J. M. Williams, et al. (2000). "Reproducibility of nerve fiber layer thickness measurements by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997). "Forward-imaging instruments for optical coherence tomography." *Optics Letters* 22.

Boppart, S. A., B. E. Bouma, et al. (1998). "Intraoperative assessment of microsurgery with three-dimensional optical coherence tomography." *Radiology* 208: 81-86.

Boppart, S. A., J. Herrmann, et al. (1999). "High-resolution optical coherence tomography-guided laser ablation of surgical tissue." *Journal of Surgical Research* 82(2): 275-84.

Bouma, B. E. and J. G. Fujimoto (1996). "Compact Kerr-lens mode-locked resonators." *Optics Letters* 21. 134-136.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3. 76-79.

Bouma, B. E., M. Ramaswamy-Paye, et al. (1997). "Compact resonator designs for mode-locked solid-state lasers." *Applied Physics B (Lasers and Optics)* B65. 213-220.

Bouma, B. E. and G. J. Tearney (2002). "Clinical imaging with optical coherence tomography." *Academic Radiology* 9(8): 942-953.

Bouma, B. E., G. J. Tearney, et al. (1996). "Self-phase-modulated Kerr-lens mode-locked Cr:forsterite laser source for optical coherence tomography." *Optics Letters* 21(22): 1839.

Bouma, B. E., G. J. Tearney, et al. (2000). "High-resolution imaging of the human esophagus and stomach in vivo using optical coherence tomography." *Gastrointestinal Endoscopy* 51(4): 467-474.

Bouma, B. E., G. J. Tearney, et al. (2003). "Evaluation of intracoronary stenting by intravascular optical coherence tomography." *Heart* 89(3): 317-320.

Bourquin, S., V. Monterosso, et al. (2000). "Video-rate optical low-coherence reflectometry based on a linear smart detector array." *Optics Letters* 25(2): 102-104.

Bourquin, S., P. Seitz, et al. (2001). "Optical coherence topography based on a two-dimensional smart detector array." *Optics Letters* 26(8): 512-514.

Bouzid, A., M. A. G. Abushagur, et al. (1995). "Fiber-optic four-detector polarimeter." *Optics Communications* 118(3-4): 329-334.

Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.

Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.

Bowd, C., L. M. Zangwill, et al. (2002). "Imaging of the optic disc and retinal nerve fiber layer: the effects of age, optic disc area, refractive error, and gender." *Journal of the Optical Society of America, A, Optics, Image Science & Vision* 19(1): 197-207.

Brand, S., J. M. Poneros, et al. (2000). "Optical coherence tomography in the gastrointestinal tract." *Endoscopy* 32(10): 796-803.

Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.

Brezinski, M. E., G. J. Tearney, et al. (1996). "Imaging of coronary artery microstructure (in vitro) with optical coherence tomography." *American Journal of Cardiology* 77 (1): 92-93.

Brezinski, M. E., G. J. Tearney, et al. (1996). "Optical coherence tomography for optical biopsy—Properties and demonstration of vascular pathology." *Circulation* 93(6): 1206-1213.

Brezinski, M. E., G. J. Tearney, et al. (1997). "Assessing atherosclerotic plaque morphology: Comparison of optical coherence tomography and high frequency intravascular ultrasound." *Heart* 77(5): 397-403.

Brink, H. B. K. and G. J. Vanblokland (1988). "Birefringence of the Human Foveal Area Assessed Invivo with Mueller-Matrix Ellipsometry." *Journal of the Optical Society of America a-Optics Image Science and Vision* 5(1): 49-57.

Brosseau, C. and D. Bicout (1994). "Entropy Production in Multiple-Scattering of Light by a Spatially Random Medium." *Physical Review* E 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-Speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

Chauhan, B. C., J. W. Blanchard, et al. "Technique for Detecting Serial Topographic Changes in the Optic Disc and Peripapillary Retina Using Scanning Laser Tomograph." *Invest. Ophthalmol Vis Sci* 41: 775-782. (2000).

Chen, Z. P., T. E. Milner, et al. (1997). "Optical Doppler tomographic imaging of fluid flow velocity in highly scattering media." *Optics Letters* 22(1): 64-66.

Chen, Z. P., T. E. Milner, et al. (1997). "Noninvasive imaging of in vivo blood flow velocity using optical Doppler tomography." *Optics Letters* 22(14): 1119-1121.

Chen, Z. P., Y. H. Zhao, et al. (1999). "Optical Doppler tomography." *Ieee Journal of Selected Topics in Quantum Electronics* 5(4): 1134-1142.

Cheong, W. F., S. A. Prahl, et al. (1990). "A Review of the Optical-Properties of Biological Tissues." *Ieee Journal of Quantum Electronics* 26(12): 2166-2185.

Chernikov, S. V., Y. Zhu, et al. (1997). "Supercontinuum self-Q-switched ytterbium fiber laser." *Optics Letters* 22(5): 298-300.

Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.

Choma, M. A., M. V. Sarunic, et al. (2003). "Sensitivity advantage of swept source and Fourier domain optical coherence tomography." *Optics Express* 11(18): 2183-2189.

Choma, M. A., C. H. Yang, et al. (2003). "Instantaneous quadrature low-coherence interferometry with 3×3 fiber-optic couplers." *Optics Letters* 28(22): 2162-2164.

Choplin, N. T. and D. C. Lundy (2001). "The sensitivity and specificity of scanning laser polarimetry in the detection of glaucoma in a clinical setting." *Ophthalmology* 108 (5): 899-904.

Christens Barry, W. A., W. J. Green, et al. (1996). "Spatial mapping of polarized light transmission in the central rabbit cornea." *Experimental Eye Research* 62(6): 651-662.

Chvapil, M., D. P. Speer, et al. (1984). "Identification of the depth of burn injury by collagen stainability." *Plastic & Reconstructive Surgery* 73(3): 438-41.

Cioffi, G. A. (2001). "Three common assumptions about ocular blood flow and glaucoma." *Survey of Ophthalmology* 45: S325-S331.

Coleman, A. L. (1999). "Glaucoma." *Lancet* 354(9192): 1803-10.

Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.

Collaborative Normal-Tension Glaucoma Study Group (1998). "The effectiveness of intraocular pressure reduction in the treatment of normal-tension glaucoma." *Am J Ophthalmol* 126: 498-505.

Collaborative Normal-Tension Glaucoma Study Group (2001). "Natural History of Normal-Tension Glaucoma." *Ophthalmology* 108: 247-253.

Colston, B. W., M. J. Everett, et al. (1998). "Imaging of hard- and soft-tissue structure in the oral cavity by optical coherence tomography." *Applied Optics* 37(16): 3582-3585.

Colston, B. W., U. S. Sathyam et al. (1998). "Dental OCT." *Optics Express* 3(6): 230-238.

Congdon, N. G., D. S. Friedman, et al. (2003). "Important causes of visual impairment in the world today." *Jama-Journal of the American Medical Association* 290(15): 2057-2060.

Cregan, R. F., B. J. Mangan, et al. (1999). "Single-mode photonic band gap guidance of light in air." *Science* 285(5433): 1537-1539.

DalMolin, M., A. Galtarossa, et al. (1997). "Experimental investigation of linear polarization in high-birefringence single-mode fibers." *Applied Optics* 36(12): 2526-2528.

Danielson, B. L. and C. D. Whittenberg (1987). "Guided-Wave Reflectometry with Micrometer Resolution." *Applied Optics* 26(14): 2836-2842.

Dave, D. P. and T. E. Milner (2000). "Doppler-angle measurement in highly scattering media." *Optics Letters* 25(20): 1523-1525.

de Boer, J. F., T. E. Milner, et al. (1998). *Two dimensional birefringence imaging in biological tissue using phase and polarization sensitive optical coherence tomography*. Trends in Optics and Photonics (TOPS): Advances in Optical Imaging and Photon Migration, Orlando, USA, Optical Society of America, Washington, DC 1998.

de Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling of White-Light Interferograms." *Optics Letters* 18(17): 1462-1464.

Denk, W., J. H. Strickler, et al. (1990). "2-Photon Laser Scanning Fluorescence Microscopy." *Science* 248(4951): 73-76.

Descour, M. R., A. H. O. Karkkainen, et al. (2002). "Toward the development of miniaturized Imaging systems for detection of precancer." *Ieee Journal of Quantum Electronics* 38(2): 122-130.

Dettwiller, L. (1997). "Polarization state interference: A general investigation." *Pure and Applied Optics* 6(1): 41-53.

DiCarlo, C. D., W. P. Roach, et al. (1999). "Comparison of optical coherence tomography imaging of cataracts with histopathology." *Journal of Biomedical Optics* 4.

Ding, Z., Y. Zhao, et al. (2002). "Real-time phase-resolved optical coherence tomography and optical Doppler tomography." *Optics Express* 10(5): 236-245.

Dobrin, P. B. (1996). "Effect of histologic preparation on the cross-sectional area of arterial rings." *Journal of Surgical Research* 61(2): 413-5.

Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.

Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." *Journal of Biomedical Optics* 3 (1): 55-65.

Drexler, W., O. Findl, et al. (1998). "Partial coherence interferometry: A novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hitzenberger, et al. (1998). "Investigation of dispersion effects in ocular media by multiple wavelength partial coherence interferometry." *Experimental Eye Research* 66(1): 25-33.

Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.

Drexler, W., C. K. Hitzenberger, et al. (1995). "Measurement of the Thickness of Fundus Layers by Partial Coherence Tomography." *Optical Engineering* 34(3): 701-710.

Drexler, W., U. Morgner, et al. (2001). "Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid vol. scatterers." *Proceedings of SPIE—The International Society for Optical Engineering* 2925: 169-178.

Eisenbeiss, W., J. Marotz, et al. (1999). "Reflection-optical multispectral imaging method for objective determination of burn depth." *Burns* 25(8): 697-704.

Elbaum, M., M. King, et al. (1972). "Wavelength-Diversity Technique for Reduction of Speckle Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo OCT imaging of hard and soft tissue of the oral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro-Ophthalmology* 18(2): 39-49.

Fercher, A. F., W. Drexler, et al. (1994). *Measurement of optical distances by optical spectrum modulation*. Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurements of Intraocular Optical Distances Using Partially Coherent Laser-Light." *Journal of Modern Optics* 38(7): 1327-1333.

Fercher, A. F., C. K. Hitzenberger, et al. (1996). *Ocular partial coherence interferometry*. Proceedings of SPIE—The International Society for Optical Engineering.

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). *In-vivo dual-beam optical coherence tomography*. Proceedings of SPIE—The International Society for Optical Engineering.
Fercher, A. F., C. K. Hitzenberger, et al. (1995). "Measurement of Intraocular Distances by Backscattering Spectral Interferometry." *Optics Communications* 117(1-2): 43-48.
Fercher, A. F., C. K. Hitzenberger, et al. (2000). "A thermal light source technique for optical coherence tomography." *Optics Communications* 185(1-3): 57-64.
Fercher, A. F., C. K. Hitzenberger, et al. (2001). "Numerical dispersion compensation for Partial Coherence Interferometry and Optical Coherence Tomography." *Optics Express* 9(12): 610-615.
Fercher, A. F., C. K. Hitzenberger, et al. (2002). "Dispersion compensation for optical coherence tomography depth- scan signals by a numerical technique." *Optics Communications* 204(1-6): 67-74.
Fercher, A. F., H. C. Li, et al. (1993). "Slit Lamp Laser-Doppler Interferometer." *Lasers in Surgery and Medicine* 13(4): 447-452.
Fercher, A. F., K. Mengedoht, et at. (1988). "Eye-Length Measurement by Interferometry with Partially Coherent-Light." *Optics Letters* 13(3): 186-188.
Ferro, P., M. Haelterman, et al. (1991). "All-Optical Polarization Switch with Long Low-Birefringence Fiber." *Electronics Letters* 27(16): 1407-1408.
Fetterman, M. R., D. Goswami, et al. (1998). "Ultrafast pulse shaping: amplification and characterization." *Optics Express* 3(10): 366-375.
Findl, O., W. Drexler, et al. (2001). "Improved prediction of intraocular lens power using partial coherence interferometry." *Journal of Cataract and Refractive Surgery* 27 (6): 861-867.
Fork, R. L., C. H. B. Cruz, et al. (1987). "Compression of Optical Pulses to 6 Femtoseconds by Using Cubic Phase Compensation." *Optics Letters* 12(7): 483-485.
Foschini, G. J. and C. D. Poole (1991). "Statistical-Theory of Polarization Dispersion in Single-Mode Fibers." *Journal of Lightwave Technology* 9(11): 1439-1456.
Francia, C., F. Bruyere, et al. (1998). "PMD second-order effects on pulse propagation in single-mode optical fibers." *Ieee Photonics Technology Letters* 10(12): 1739-1741.
Fried, D., R. E. Glena, et al. (1995). "Nature of Light-Scattering in Dental Enamel and Dentin at Visible and near-Infrared Wavelengths." *Applied Optics* 34(7): 1278-1285.
Fujimoto, J. G., M. E. Brezinski, et al. (1995). "Optical Biopsy and Imaging Using Optical Coherence Tomography." *Nature Medicine* 1(9): 970-972.
Fukasawa, A. and H. Iijima (2002). "Optical coherence tomography of choroidal osteoma." *American Journal of Ophthalmology* 133(3): 419-21.
Fymat, A. L. (1981). "High-Resolution Interferometric Spectrophotopolarimetry." *Optical Engineering* 20(1): 25-30.
Galtarossa, A., L. Palmieri, et al. (2000). "Statistical characterization of fiber random birefringence." *Optics Letters* 25(18): 1322-1324.
Galtarossa, A., L. Palmieri, et al. (2000). "Measurements of beat length and perturbation length in long single-mode fibers." *Optics Letters* 25(6): 384-386.
Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.
Garcia, N. and M. Nieto-Vesperinas (2002). "Left-handed materials do not make a perfect lens." *Physical Review Letters* 88(20).
Gelikonov, V. M., G. V. Gelikonov, et al. (1995). "Coherent Optical Tomography of Microscopic Inhomogeneities in Biological Tissues." *Jetp Letters* 61(2): 158-162.
George, N. and A. Jain (1973). "Speckle Reduction Using Multiple Tones of Illumination." *Applied Optics* 12(6): 1202-1212.
Gibson, G. N., R. Klank, et al. (1996). "Electro-optically cavity-dumped ultrashort-pulse Ti:sapphire oscillator." *Optics Letters* 21(14): 1055.
Gil, J. J. (2000). "Characteristic properties of Mueller matrices." *Journal of the Optical Society of America a-Optics Image Science and Vision* 17(2): 328-334.

Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.
Gladkova, N. D., G. A. Petrova, et al. (2000). "In vivo optical coherence tomography imaging of human skin: norm and pathology." *Skin Research and Technology* 6 (1): 6-16.
Glaessl, A., A. G. Schreyer, et al. (2001). "Laser surgical planning with magnetic resonance imaging-based 3-dimensional reconstructions for intralesional Nd : YAG laser therapy of a venous malformation of the neck." *Archives of Dermatology* 137(10): 1331-1335.
Gloesmann, M., B. Hermann, et al. (2003). "Histologic correlation of pig retina radial stratification with ultrahigh-resolution optical coherence tomography." *Investigative Ophthalmology & Visual Science* 44(4): 1696-1703.
Goldberg, L. and D. Mehuys (1994). "High-Power Superluminescent Diode Source." *Electronics Letters* 30(20): 1682-1684.
Goldsmith, J. A., Y. Li, et al. (2005). "Anterior chamber width measurement by high speed optical coherence tomography." *Ophthalmology* 112(2): 238-244.
Goldstein, L. E., J. A. Muffat, et al. (2003). "Cytosolic beta-amyloid deposition and supranuclear cataracts in lenses from people with Alzheimer's disease." *Lancet* 361(9365): 1258-1265.
Golubovic, B., B. E. Bouma, et al. (1996). "Thin crystal, room-temperature Cr/sup 4 +/:forstefite laser using near-infrared pumping." *Optics Letters* 21(24): 1993-1995.
Gonzalez, S. and Z. Tannous (2002). "Real-time, in vivo confocal reflectance microscopy of basal cell carcinoma." *Journal of the American Academy of Dermatology* 47(6): 869-874.
Gordon, M. O. and M. A. Kass (1999). "The Ocular Hypertension Treatment Study: design and baseline description of the participants." *Archives of Ophthalmology* 117(5): 573-83.
Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.
Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.
Greenfield, D. S., H. Bagga, et al. (2003). "Macular thickness changes in glaucomatous optic neuropathy detected using optical coherence tomography." *Archives of Ophthalmology* 121(1): 41-46.
Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.
Griffin, R. A., D. D. Sampson, et al. (1995). "Coherence Coding for Photonic Code-Division Multiple-Access Networks." *Journal of Lightwave Technology* 13(9): 1826-1837.
Guedes, V., J. S. Schuman, et al. (2003). "Optical coherence tomography measurement of macular and nerve fiber layer thickness in normal and glaucomatous human eyes." *Ophthalmology* 110(1): 177-189.
Gueugniaud, P. Y., H. Carsin, et al. (2000). "Current advances in the initial management of major thermal burns. [Review] [76 refs]." *Intensive Care Medicine* 26(7): 848-56.
Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.
Gurses-Ozden, R., H. Ishikawa, et al. (1999). "Increasing sampling density improves reproducibility of optical coherence tomography measurements." *Journal of Glaucoma* 8(4): 238-41.
Guzzi, R. (1998). "Scattering Theory from Homogeneous and Coated Spheres." 1-11.
Haberland, U. B., Vladimir; Schmitt, Hans J. (1996). "Optical coherent tomography of scattering media using electrically tunable near-infrared semiconductor laser." *Applied Optics* Draft Copy.
Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.

Hale, G. M. and M. R. Querry (1973). "Optical-Constants of Water in 200-Nm to 200-Mum Wavelength Region." *Applied Optics* 12(3): 555-563.

Hammer, D. X., R. D. Ferguson, et al. "Image stabilization for scanning laser ophthalmoscopy." *Optics Express* 10(26): (2002). 1542.

Hara, T., Y. Ooi, et al. (1989). "Transfer Characteristics of the Microchannel Spatial Light-Modulator." *Applied Optics* 28(22): 4781-4786.

Harland, C. C., S. G. Kale, et al. (2000). "Differentiation of common benign pigmented skin lesions from melanoma by high-resolution ultrasound." *British Journal of Dermatology* 143(2): 281-289.

Hartl, I., X. D. Li, et al. (2001). "Ultrahigh-resolution optical coherence tomography using continuum generation in an air-silica microstructure optical fiber." *Optics Letters* 26(9): 608-610.

Hassenstein, A., A. A. Bialasiewicz, et al. (2000). "Optical coherence tomography in uveitis patients." *American Journal of Ophthalmology* 130(5): 669-70.

Hattenhauer, M. G., D. H. Johnson, et al. (1998). "The probability of blindness from open-angle glaucoma. [see comments]." *Ophthalmology* 105(11): 2099-104.

Hausler, G., J. M. Herrmann, et al. (1996). "Observation of light propagation in volume scatterers with 10(11)-fold slow motion." *Optics Letters* 21(14): 1087-1089.

Hazebroek, H. F. and A. A. Holscher (1973). "Interferometric Ellipsometry." *Journal of Physics E-Scientific Instruments* 6(9): 822-826.

Hazebroek, H. F. and W. M. Visser (1983). "Automated Laser Interferometric Ellipsometry and Precision Reflectometry." *Journal of Physics E-Scientific Instruments* 16(7): 654-661.

He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.

Hee, M. R., J. A. Izatt, et al. (1993). "Femtosecond Transillumination Optical Coherence Tomography." *Optics Letters* 18(12): 950-952.

Hee, M. R., J. A. Izatt, et al. (1995). "Optical coherence tomography of the human retina." *Archives of Ophthalmology* 113(3): 325-32.

Hee, M. R., C. A. Puliafito, et al. (1998). "Topography of diabetic macular edema with optical coherence tomography." *Ophthalmology* 105(2): 360-70.

Hee, M. R., C. A. Puliafito, et al. (1995). "Quantitative assessment of macular edema with optical coherence tomography." *Archives of Ophthalmology* 113(8): 1019-29.

Hellmuth, T. and M. Welle (1998). "Simultaneous measurement of dispersion, spectrum, and distance with a fourier transform spectrometer." *Journal of Biomedical Optics* 3(1): 7-11.

Hemenger, R. P. (1989). "Birefringence of a medium of tenuous parallel cylinders." *Applied Optics* 28(18): 4030-4034.

Henry, M. (1981). "Fresnel-Arago Laws for Interference in Polarized-Light —Demonstration Experiment." *American Journal of Physics* 49(7): 690-691.

Herz, P. R., Y. Chen, et al. (2004). "Micromotor endoscope catheter for in vivo, ultrahigh-resolution optical coherence tomography." *Optics Letters* 29(19): 2261-2263.

Hirakawa, H., H. Iijima, et al. (1999). "Optical coherence tomography of cystoid macular edema associated with retinitis pigmentosa." *American Journal of Ophthalmology* 128(2): 185-91.

Hitzenberger, C. K., A. Baumgartner, et al. (1994). "Interferometric Measurement of Corneal Thickness with Micrometer Precision." *American Journal of Ophthalmology* 118(4): 468-476.

Hitzenberger, C. K., A. Baumgartner, et al. (1999). "Dispersion effects in partial coherence interferometry: Implications for intraocular ranging." *Journal of Biomedical Optics* 4(1): 144-151.

Hitzenberger, C. K., A. Baumgartner, et al. (1998). "Dispersion induced multiple signal peak splitting in partial coherence interferometry." *Optics Communications* 154 (4): 179-185.

Hitzenberger, C. K., M. Danner, et al. (1999). "Measurement of the spatial coherence of superluminescent diodes." *Journal of Modern Optics* 46(12): 1763-1774.

Hitzenberger, C. K. and A. F. Fercher (1999). "Differential phase contrast in optical coherence tomography." *Optics Letters* 24(9): 622-624.

Hitzenberger, C. K., M. Sticker, et al. (2001). "Differential phase measurements interferometry without 2 pi ambiguity." *Optics Letters* 26(23): 1864-1866.

Hoeling, B. M., A. D. Fernandez, et al. (2000). "An optical coherence microscope for 3-dimensional imaging in developmental biology." *Optics Express* 6(7): 136-146.

Hoerauf, H., C. Scholz, et al. (2002). "Transscleral optical coherence tomography: a new imaging method for the anterior segment of the eye." *Archives of Ophthalmology* 120(6): 816-9.

Hoffmann, K., M. Happe, et al. (1998). "Optical coherence tomography (OCT) in dermatology." *Journal of Investigative Dermatology* 110(4): 583-583.

Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.

Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.

Holland, A. J. A., H. C. O. Martin, et al. (2002). "Laser Doppler imaging prediction of burn wound outcome in children." *Burns* 28(1): 11-17.

Hotate, K. and T. Okugawa (1994). "Optical Information-Processing by Synthesis of the Coherence Function." *Journal of Lightwave Technology* 12(7): 1247-1255.

Hourdakis, C. J. and A. Perris (1995). "A Monte-Carlo Estimation of Tissue Optical-Properties for Use in Laser Dosimetry." *Physics in Medicine and Biology* 40(3): 351-364.

Hu, Z., F. Li, et al. (2000). "Wavelength-tunable narrow-linewidth semiconductor fiber-ring laser." *IEEE Photonics Technology Letters* 12(8): 977-979.

Huang, F., W. Yang, et al. (2001). "Quadrature spectral interferometric detection and pulse shaping." *Optics Letters* 26(6): 382-384.

Huang, X. R. and R. W. Knighton (2002). "Linear birefringence of the retinal nerve fiber layer measured in vitro with a multispectral imaging micropolarimeter." *Journal of Biomedical Optics* 7(2): 199-204.

Huber, R., M. Wojtkowski, et al. (2005). "Amplified, frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a-Optics Image Science and Vision* 16(9): 2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Banos, et al. (1999). "Polarization-induced pulse spreading optical fibers with zero differential group delay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.

Hyde, S. C. W., N. P. Barry, et al. (1995). "Depth-Resolved Holographic Imaging through Scattering Media by Photorefraction." *Optics Letters* 20(11): 1331-1333.

Iftimia, N. V., B. E. Bouma, et al. (2004). "Adaptive ranging for optical coherence tomography." *Optics Express* 12(17): 4025-4034.

Iida, T., N. Hagimura, et al. (2000). "Evaluation of central serous chorioretinopathy with optical coherence tomography." *American Journal of Ophthalmology* 129(1): 16-20.

Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132(1): 81-4.

Indebetouw, G. and P. Klysubun (2000). "Imaging through scattering media with depth resolution by use of low-coherence gating in spatiotemporal digital holography." *Optics Letters* 25(4): 212-214.

Ip, M. S., B. J. Baker, et al. (2002). "Anatomical outcomes of surgery for idiopathic macular hole as determined by optical coherence tomography." *Archives of Ophthalmology* 120(1): 29-35.

Ismail, R., V. Tanner, et al. (2002). "Optical coherence tomography imaging of severe commotio retinae and associated macular hole." *British Journal of Ophthalmology* 86(4): 473-4.

Izatt, J. A., M. R. Hee, et al. (1994). "Optical Coherence Microscopy in Scattering Media." *Optics Letters* 19(8): 590-592.

Izatt, J. A., M. R. Hee, et al. (1994). "Micrometer-scale resolution imaging of the anterior eye in vivo with optical coherence tomography." *Archives of Ophthalmology* 112 (12): 1584-9.

Izatt, J. A., M. D. Kulkarni, et al. (1997). "In vivo bidirectional color Doppler flow imaging of picoliter blood volumes using optical coherence tomography." *Optics Letters* 22(18): 1439-1441.

Izatt, J. A., M. D. Kulkarni, et al. (1996). "Optical coherence tomography and microscopy in gastrointestinal tissues." *IEEE Journal of Selected Topics in Quantum Electronics* 2(4): 1017.

Jacques, S. L., J. S. Nelson, et al. (1993). "Pulsed Photothermal Radiometry of Port-Wine-Stain Lesions." *Applied Optics* 32(13): 2439-2446.

Jacques, S. L., J. R. Roman, et al. (2000). "Imaging superficial tissues with polarized light." *Lasers in Surgery and Medicine* 26(2): 119-129.

Jang, I. K., B. E. Bouma, et al. (2002). "Visualization of coronary atherosclerotic plaques in patients using optical coherence tomography: Comparison with intravascular ultrasound." *American College of Cardiology* 39(4): 604-609.

Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S,.

Jang, I. K., G. J. Tearney, et al. (2000). "Comparison of optical coherence tomography and intravascular ultrasound for detection of coronary plaques with large lipid-core in living patients." *Circulation* 102(18): 509-509.

Jeng, J. C., A. Bridgeman, et al. (2003). "Laser Doppler imaging determines need for excision and grafting in advance of clinical judgment: a prospective blinded trial." *Burns* 29(7): 665-670.

Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.

Johnson, C. A., J. L. Keltner, et al. (2002). "Baseline visual field characteristics in the ocular hypertension treatment study." *Ophthalmology* 109(3): 432-7.

Jones, R. C. (1941). "A new calculus for the treatment of optical systems III. The Sohncke theory of optical activity." *Journal of the Optical Society of America* 31 (7): 500-503.

Jones, R. C. (1941). "A new calculus for the treatment of optical systems I. Description and discussion of the calculus." *Journal of the Optical Society of America* 31(7): 488-493.

Jones, R. C. (1942). "A new calculus for the treatment of optical systems. IV." *Journal of the Optical Society of America* 32(8): 486-493.

Jones, R. C. (1947). "A New Calculus for the Treatment of Optical Systems .6. Experimental Determination of the Matrix." *Journal of the Optical Society of America* 37(2): 110-112.

Jones, R. C. (1947). "A New Calculus for the Treatment of Optical Systems .5. A More General Formulation, and Description of Another Calculus." *Journal of the Optical Society of America* 37(2): 107-110.

Jones, R. C. (1948). "A New Calculus for the Treatment of Optical Systems .7. Properties of the N-Matrices." *Journal of the Optical Society of America* 38(8): 671-685.

Jones, R. C. (1956). "New Calculus for the Treatment of Optical Systems .8. Electromagnetic Theory." *Journal of the Optical Society of America* 46(2): 126-131.

Jopson, R. M., L. E. Nelson, et al. (1999). "Measurement of second-order polarization-mode dispersion vectors in optical fibers." *Ieee Photonics Technology Letters* 11 (9): 1153-1155.

Jost, B. M., A. V. Sergienko, et al. (1998). "Spatial correlations of spontaneously down-converted photon pairs detected with a single-photon-sensitive CCD camera." *Optics Express* 3(2): 81-88.

Kaplan, B., E. Compain, et al. (2000). "Phase-modulated Mueller ellipsometry characterization of scattering by latex sphere suspensions." *Applied Optics* 39 (4): 629-636.

Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.

Kasuga, Y., J. Arai, et al. (2000). "Optical coherence tomograghy to confirm early closure of macular holes." *American Journal of Ophthalmology* 130(5): 675-6.

Kaufman, T., S. N. Lusthaus, et al. (1990). "Deep Partial Skin Thickness Burns—a Reproducible Animal-Model to Study Burn Wound-Healing." *Burns* 16(1): 13-16.

Kemp, N. J., J. Park, et al. (2005). "High-sensitivity determination of birefringence in turbid media with enhanced polarization-sensitive optical coherence tomography." *Journal of the Optical Society of America a-Optics Image Science and Vision* 22(3): 552-560.

Kerrigan-Baumrind, L. A., H. A. Quigley, et al. (2000). "Number of ganglion cells in glaucoma eyes compared with threshold visual field tests in the same persons." *Investigative Ophthalmology & Visual Science* 41(3): 741-8.

Kesen, M. R., G. L. Spaeth, et al. (2002). "The Heidelberg Retina Tomograph vs clinical impression in the diagnosis of glaucoma." *American Journal of Ophthalmology* 133(5): 613-6.

Kienle, A. and R. Hibst (1995). "A New Optimal Wavelength for Treatment of Port-Wine Stains." *Physics in Medicine and Biology* 40(10): 1559-1576.

Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.

Kim, B. Y. and S. S. Choi (1981). "Analysis and Measurement of Birefringence in Single-Mode Fibers Using the Backscattering Method." *Optics Letters* 6(11): 578-580.

Kimel, S., L. O. Svaasand, et al. (1994). "Differential Vascular-Response to Laser Photothermolysis." *Journal of Investigative Dermatology* 103(5): 693-700.

Kloppenberg, F. W. H., G. Beerthuizen, et al. (2001). "Perfusion of burn wounds assessed by Laser Doppler Imaging is related to burn depth and healing time." *Burns* 27(4): 359-363.

Knighton, R. W. and X. R. Huang (2002). "Analytical methods for scanning laser polarimetry." *Optics Express* 10(21): 1179-1189.

Knighton, R. W., X. R. Huang, et al. (2002). "Analytical model of scanning laser polarimetry for retinal nerve fiber layer assessment." *Investigative Ophthalmology & Visual Science* 43(2): 383-392.

Knuettel, A. R. S., Joseph M.: Shay, M.; Knutson, Jay R. (1994). "Stationary low-coherence light imaging and spectroscopy using a CCD camera." *Proc. SPIE*, vol. 2135: p. 239-250.

Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.

Knuttel, A. and J. M. Schmitt (1993). "Stationary Depth-Profiling Reflectometer Based on Low-Coherence Interferometry." *Optics Communications* 102(3-4): 193-198.

Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.

Kobayashi, M., H. Hanafusa, et al. (1991). "Polarization-Independent Interferometric Optical-Time-Domain Reflectometer." *Journal of Lightwave Technology* 9(5): 623-628.

Kolios, M. C., M. D. Sherar, et al. (1995). "Large Blood-Vessel Cooling in Heated Tissues—a Numerical Study." *Physics in Medicine and Biology* 40(4): 477-494.

Koozekanani, D., K. Boyer, et al. (2001). "Retinal thickness measurements from optical coherence tomography using a Markov boundary model." *Ieee Transactions on Medical Imaging* 20(9): 900-916.

Kop, R. H. J. and R. Sprik (1995). "Phase-sensitive interferometry with ultrashort optical pulses." *Review of Scientific Instruments* 66(12): 5459-5463.

Kramer, R. Z., J. Bella, et al. (1999). "Sequence dependent conformational variations of collagen triple-helical structure." *Nature Structural Biology* 6(5): 454-7.

Kulkarni, M. D., T. G. van Leeuwen, et al. (1998). "Velocity-estimation accuracy and frame-rate limitations in color Doppler optical coherence tomography." *Optics Letters* 23(13): 1057-1059.

Kwon, Y. H., C. S. Kim, et al. (2001). "Rate of visual field loss and long-term visual outcome in primary open-angle glaucoma." *American Journal of Ophthalmology* 132(1): 47-56.

Kwong, K. F., D. Yankelevich, et al. (1993). "400-Hz Mechanical Scanning Optical Delay-Line." *Optics Letters* 18(7): 558-560.

Landers, J., I. Goldberg, et al. (2002). "Analysis of risk factors that may be associated with progression from ocular hypertension to primary open angle glaucoma." *Clin Experiment Ophthalmogy* 30(4): 242-7.

Laszlo, A. and A. Venetianer (1998). Heat resistance in mammalian cells: Lessons and challenges. *Stress of Life*. 851: 169-178.

Laszlo, A. and A. Venetianer (1998). "Heat resistance in mammalian cells: lessons and challenges [Review] [52 refs]." *Annals of the New York Academy of Sciences* 851: 169-78.

Laufer, J., R. Simpson, et al. (1998). "Effect of temperature on the optical properties of ex vivo human dermis and subdermis." *Physics in Medicine and Biology* 43(9): 2479-2489.

Lederer, D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121(9): 1303-1310.

Lehrer, M. S., T. T. Sun, et al. (1998). "Strategies of epithelial repair: modulation of stem cell and transit amplifying cell proliferation." *Journal of Cell Science* 111(Pt 19): 2867-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb, R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.

Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetterer, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utilization of Mueller matrix formalism to obtain optical targets depolarization and polarization properties." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7): 918-24.

Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.

Leske, M. C., A. Heijl, et al. (1999). "Early Manifest Glaucoma Trial. Design and Baseline Data." *Ophthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth- independent transversal resolution." *Journal of Modern Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26: 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evaluation of skin subjected to instantaneous heating." *IEEE Transactions on Biomedical Engineering* 46(4): 420-8.

Luke, D. G., R. McBride, et al. (1995). "Polarization mode dispersion minimization in fiber-wound piezoelectric cylinders." *Optics Letters* 20(24): 2550-2552.

MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.

Maitland, D. J. and J. T. Walsh, Jr. (1997). "Quantitative measurements of linear birefringence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Applied Optics* 30(22): 3154-3162.

Marshall, G. W., S. J. Marshall, et al. (1997). "The dentin substrate: structure and properties related to bonding." *Journal of Dentistry* 25(6): 441-458.

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion—Application to Fiber Compensation in 1.3-1.6 Mu-M Region." *Ieee Journal of Quantum Electronics* 23(1): 59-64.

Martinez, O. E., J. P. Gordon, et al. (1984). "Negative Group-Velocity Dispersion Using Refraction." *Journal of the Optical Society of America a-Optics Image Science and Vision* 1(10): 1003-1006.

McKinney, J. D., M. A. Webster, et al. (2000). "Characterization and imaging in optically scattering media by use of laser speckle and a variable-coherence source." *Optics Letters* 25(1): 4-6.

Miglior, S., M. Casula, et al. (2001). "Clinical ability of Heidelberg retinal tomograph examination to detect glaucomatous visual field changes." *Ophthalmology* 108 (9): 1621-7.

Milner, T. E., D. M. Goodman, et al. (1996). "Imaging laser heated subsurface chromophores in biological materials: Determination of lateral physical dimensions." *Physics in Medicine and Biology* 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a-Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.

Mitsui, T. (1999). "High-speed detection of ballistic photons propagating through suspensions using spectral interferometry." *Japanese Journal of Applied Physics* Part 1-Regular Papers Short Notes & Review Papers 38(5A): 2978-2982.

Molteno, A. C., N. J. Bosma, et al. (1999). "Otago glaucoma surgery outcome study: long-term results of trabeculectomy—1976 to 1995." *Ophthalmology* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.

Mourant, J. R., A. H. Hielscher, et al. (1998). "Evidence of intrinsic differences in the light scattering properties of tumorigenic and nontumorigenic cells." *Cancer Cytopathology* 84(6): 366-374.

Muller, M., J. Squier, et al. (1998). "Dispersion pre-compensation of 15 femtosecond optical pulses for high-numerical-aperture objectives." *Journal of Microscopy-Oxford* 191: 141-150.

Muscat, S., N. McKay, et al. (2002). "Repeatability and reproducibility of corneal thickness measurements by optical coherence tomography." *Investigative Ophthalmology & Visual Science* 43(6): 1791-5.

Musch, D. C., P. R. Lichter, et al. (1999). "The Collaborative Initial Glaucoma Treatment Study. Study Design, Methods, and Baseline Characteristics of Enrolled Patients." *Ophthalmology* 106: 653-662.

Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.

Nelson, J. S., K. M. Kelly, et al. (2001). "Imaging blood flow in human port-wine stain in situ and in real time using optical Doppler tomography." *Archives of Dermatology* 137(6): 741-744.

Newson, T. P., F. Farahi, et al. (1988). "Combined Interferometric and Polarimetric Fiber Optic Temperature Sensor with a Short Coherence Length Source." *Optics Communications* 68(3): 161-165.

Nov., L. J. (1993). "Recovery of the Matrix Operators in the Similarity and Congruency Transformations—Applications in Polarimetry." *Journal of the Optical Society of America a-Optics Image Science and Vision* 10(4): 719-739.

Oh, W. Y., S. H. Yun, et al. (2005). "Wide tuning range wavelength-swept laser with two semiconductor optical amplifiers." *Ieee Photonics Technology Letters* 17(3): 678-680.

Oka, K. and T. Kato (1999). "Spectroscopic polarimetry with a channeled spectrum." *Optics Letters* 24(21): 1475-1477.

Okugawa, T. and K. Rotate (1996). "Real-time optical image processing by synthesis of the coherence function using real-time holography." *Ieee Photonics Technology Letters* 8(2): 257-259.

Oshima, M., R. Torii, et al. (2001). "Finite element simulation of blood flow in the cerebral artery." *Computer Methods in Applied Mechanics and Engineering* 191 (6-7): 661-671.

Pan, Y. T., H. K. Xie, et al. (2001). "Endoscopic optical coherence tomography based on a microelectromechanical mirror." *Optics Letters* 26(24): 1966-1968.

Parisi, V., G. Manni, et al. (2001). "Correlation between optical coherence tomography, pattern electroretinogram, and visual evoked potentials in open-angle glaucoma patients." *Ophthalmology* 108(5): 905-12.

Park, B. H., M. C. Pierce, et al. (2005). "Real-time fiber-based multifunctional spectral-domain optical coherence tomography at 1.3 mu m." *Optics Express* 13(11): 3931-3944.

Park, D. H., J. W. Hwang, et al. (1998). "Use of laser Doppler flowmetry for estimation of the depth of burns." *Plastic and Reconstructive Surgery* 101(6): 1516-1523.

Pendry, J. B., A. J. Holden, et al. (1999). "Magnetism from conductors and enhanced nonlinear phenomena." *Ieee Transactions on Microwave Theory and Techniques* 47(11): 2075-2084.

Penninckx, D. and V. Morenas (1999). "Jones matrix of polarization mode dispersion." *Optics Letters* 24(13): 875-877.

Pierce, M. C., M. Shishkov, et al. (2005). "Effects of sample arm motion in endoscopic polarization-sensitive optical coherence tomography." *Optics Express* 13(15): 5739-5749.

Pircher, M., E. Gotzinger, et al. (2003). "Measurement and imaging of water concentration in human cornea with differential absorption optical coherence tomography." *Optics Express* 11(18): 2190-2197.

Pircher, M., E. Gotzinger, et al. (2003). "Speckle reduction in optical coherence tomography by frequency compounding." *Journal of Biomedical Optics* 8(3): 565-569.

Podoleanu, A. G., G. M. Dobre, et al. (1998). "En-face coherence imaging using galvanometer scanner modulation." *Optics Letters* 23(3): 147-149.

Podoleanu, A. G. and D. A. Jackson (1999). "Noise analysis of a combined optical coherence tomograph and a confocal scanning ophthalmoscope." *Applied Optics* 38(10): 2116-2127.

Podoleanu, A. G., J. A. Rogers, et al. (2000). "Three dimensional OCT images from retina and skin." *Optics Express* 7(9): 292-298.

Podoleanu, A. G., M. Seeger, et al. (1998). "Transversal and longitudinal images from the retina of the living eye using low coherence reflectometry." *Journal of Biomedical Optics* 3(1): 12-20.

Poole, C. D. (1988). "Statistical Treatment of Polarization Dispersion in Single-Mode Fiber." *Optics Letters* 13(8): 687-689.

Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.

Radhakrishnan, S., A. M. Rollins, et al. (2001). "Real-time optical coherence tomography of the anterior segment at 1310 nm." *Archives of Ophthalmology* 119(8): 1179-1185.

Rogers, A. J. (1981). "Polarization-Optical Time Domain Reflectometry—a Technique for the Measurement of Field Distributions." *Applied Optics* 20(6): 1060-1074.

Rollins, A. M. and J. A. Izatt (1999). "Optimal interferometer designs for optical coherence tomography." *Optics Letters* 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.

Rollins, A. M., S. Yazdanfar, et al. (2002). "Real-time in vivo colors Doppler optical coherence tomography." *Journal of Biomedical Optics* 7(1): 123-129.

Rollins, A. M., S. Yazdanfar, et al. (2000). "Imaging of human retinal hemodynamics using color Doppler optical coherence tomography." *Investigative Ophthalmology & Visual Science* 41(4): S548-S548.

Sandoz, P. (1997). "Wavelet transform as a processing tool in white-light interferometry." *Optics Letters* 22(14): 1065-1067.

Sankaran, V., M. J. Everett, et al. (1999). "Comparison of polarized-light propagation in biological tissue and phantoms." *Optics Letters* 24(15): 1044-1046.

Sankaran, V., J. T. Walsh, et al. (2000). "Polarized light propagation through tissue phanto, ehms containing densely packed scatterers." *Optics Letters* 25(4): 239-241.

Sarunic, M. V., M. A. Choma, et al. (2005). "Instantaneous complex conjugate resolved spectral domain and swept-source OCT using 3 × 3 fiber couplers." *Optics Express* 13(3): 957-967.

Sathyam, U. S., B. W. Colston, et al. (1999). "Evaluation of optical coherence quantitation of analytes in turbid media by use of two wavelengths." *Applied Optics* 38(10): 2097-2104.

Schmitt, J. M. (1997). "Array detection for speckle reduction in optical coherence microscopy." *Physics in Medicine and Biology* 42(7): 1427-1439.

Schmitt, J. M. (1999). "Optical coherence tomography (OCT): A review." *Ieee Journal of Selected Topics in Quantum Electronics* 5(4): 1205-1215.

Schmitt, J. M. and A. Knuttel (1997). "Model of optical coherence tomography of heterogeneous tissue." *Journal of the Optical Society of America a-Optics Image Science and Vision* 14(6): 1231-1242.

Schmitt, J. M., S. L. Lee, et al. (1997). "An optical coherence microscope with enhanced resolving power in thick tissue." *Optics Communications* 142(4-6): 203-207.

Schmitt, J. M., S. H. Xiang, et al. (1998). "Differential absorption imaging with optical coherence tomography." *Journal of the Optical Society of America a-Optics Image Science and Vision* 15(9): 2288-2296.

Schmitt, J. M., S. H. Xiang, et al. (1999). "Speckle in optical coherence tomography." *Journal of Biomedical Optics* 4(1): 95-105.

Schmitt, J. M., M. J. Yadlowsky, et al. (1995). "Subsurface Imaging of Living Skin with Optical Coherence Microscopy." *Dermatology* 191(2): 93-98.

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode lasers." *Optics Letters* 24(4): 238-240.

Simon, R. (1982). "The Connection between Mueller and Jones Matrices of Polarization Optics." *Optics Communications* 42(5): 293-297.

Smithies, D. J., T. Lindmo, et al. (1998). "Signal attenuation and localization in optical coherence tomography studied by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optic acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain Reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimura, et al. (1994). "Optical Multimode Frequency-Domain Reflectometer." *Optics Letters* 19(8): 587-589.

Tan-no, N., T. Ichimura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optic catheter- endoscope for optical coherence tomography (vol. 21, p. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* 92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jang, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

Tower, T. T. and R. T. Tranquillo (2001). "Alignment maps of tissues: I. Microscopic elliptical polarimetry." *Biophysical Journal* 81(5): 2954-2963.

Tower, T. T. and R. T. Tranquillo (2001). "Alignment maps of tissues: II. Fast harmonic analysis for imaging." *Biophysical Journal* 81(5): 2964-2971.

Troy, T. L. and S. N. Thennadil (2001). "Optical properties of human skin in the near infrared wavelength range of 1000 to 2200 nm." *Journal of Biomedical Optics* 6 (2): 167-176.

Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.

Vakhtin, A. B., K. A. Peterson, et al. (2003). "Differential spectral interferometry: an imaging technique for biomedical applications." *Optics Letters* 28(15): 1332-1334.

Vakoc, B. J., S. H. Yun, et al. (2005). "Phase-resolved optical frequency domain imaging." *Optics Express* 13(14): 5483-5493.

van Leeuwen, T. G., M. D. Kulkarni, et al. (1999). "High-flow-velocity and shear-rate imaging by use of color Doppler optical coherence tomography." *Optics Letters* 24(22): 1584-1586.

Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.

Vargas, O., E. K. Chan, et al. (1999). "Use of an agent to reduce scattering in skin." *Lasers in Surgery and Medicine* 24(2): 133-141.

Wang, R. K. (1999). "Resolution improved optical coherence-gated tomography for imaging through biological tissues." *Journal of Modern Optics* 46(13): 1905-1912.

Wang, X. J., T. E. Milner, et al. (1997). "Measurement of fluid-flow-velocity profile in turbid media by the use of optical Doppler tomography." *Applied Optics* 36(1): 144-149.

Wang, X. J., T. E. Milner, et al. (1995). "Characterization of Fluid-Flow Velocity by Optical Doppler Tomography." *Optics Letters* 20(11): 1337-1339.

Wang, Y. M., J. S. Nelson, et al. (2003). "Optimal wavelength for ultrahigh-resolution optical coherence tomography." *Optics Express* 11(12): 1411-1417.

Wang, Y. M., Y. H. Zhao, et al. (2003). "Ultrahigh-resolution optical coherence tomography by broadband continuum generation from a photonic crystal fiber." *Optics Letters* 28(3): 182-184.

Watkins, L. R., S. M. Tan, et al. (1999). "Determination of interferometer phase distributions by use of wavelets." *Optics Letters* 24(13): 905-907.

Wetzel, J. (2001). "Optical coherence tomography in dermatology: a review." *Skin Research and Technology* 7(1): 1-9.

Wentworth, R. H. (1989). "Theoretical Noise Performance of Coherence-Multiplexed Interferometric Sensors." *Journal of Lightwave Technology* 7(6): 941-956.

Westphal, V., A. M. Rollins, et al. (2002). "Correction of geometric and refractive image distortions in optical coherence tomography applying Fermat's principle." *Optics Express* 10(9): 397-404.

Westphal, V., S. Yazdanfar, et al. (2002). "Real-time, high velocity-resolution color Doppler optical coherence tomography." *Optics Letters* 27(1): 34-36.

Williams, P. A. (1999). "Rotating-wave-plate Stokes polarimeter for differential group delay measurements of polarization-mode dispersion." *Applied Optics* 38(31): 6508-6515.

Wojtkowski, M., T. Bajraszewski, et al. (2003). "Real-time in vivo imaging by high-speed spectral optical coherence tomography." *Optics Letters* 28(19): 1745-1747.

Wojtkowski, M., A. Kowalczyk, et al. (2002). "Full range complex spectral optical coherence tomography technique in eye imaging." *Optics Letters* 27(16): 1415-1417.

Wojtkowski, M., R. Leitgeb, et al. (2002). "In vivo human retinal imaging by Fourier domain optical coherence tomography." *Journal of Biomedical Optics* 7(3): 457-463.

Wojtkowski, M., R. Leitgeb, et al. (2002). "Fourier domain OCT imaging of the human eye in vivo." *Proc. SPIE* 4619: 230-236.

Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.

Wong, B. J. F., Y. H. Zhao, et al. (2004). "Imaging the internal structure of the rat cochlea using optical coherence tomography at 0.827 mu m and 1.3 mu m." *Otolaryngology-Head and Neck Surgery* 130(3): 334-338.

Yang, C., A. Wax, et al. (2001). "Phase-dispersion optical tomography." *Optics Letters* 26(10): 686-688.

Yang, C., A. Wax, et al. (2001). "Phase-referenced interferometer with subwavelength and subhertz sensitivity applied to the study of cell membrane dynamics." *Optics Letters* 26(16): 1271-1273.

Yang, C. H., A. Wax, et al. (2001). "Phase-dispersion optical tomography." *Optics Letters* 26(10): 686-688.

Yang, C. H., A. Wax, et al. (2000). "Interferometric phase-dispersion microscopy." *Optics Letters* 25(20): 1526-1528.

Yang, V. X. D., M. L. Gordon, et al. (2002). "Improved phase-resolved optical Doppler tomography using the Kasai velocity estimator and histogram segmentation." Optics Communications 208(4-6): 209-214.

Yang, V. X. D., M. L. Gordon, et al. (2003). "High speed, wide velocity dynamic range Doppler optical coherence tomography (Part I): System design, signal processing, and performance." *Optics Express* 11(7): 794-809.

Yang, V. X. D., M. L. Gordon, et al. (2003). "High speed, wide velocity dynamic range Doppler optical coherence tomography (Part II): Imaging in vivo cardiac dynamics of Xenopus laevis." *Optics Express* 11(14): 1650-1658.

Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.

Yang, V. X. D., B. Qi, et al. (2003). "In vivo feasibility of endoscopic catheter-based Doppler optical coherence tomography." *Gastroenterology* 124(4): A49-A50.

Yao, G. and L. H. V. Wang (2000). "Theoretical and experimental studies of ultrasound-modulated optical tomography in biological tissue." *Applied Optics* 39(4): 659-664.

Yazdanfar, S. and J. A. Izatt (2002). "Self-referenced Doppler optical coherence tomography." *Optics Letters* 27(23): 2085-2087.

Yazdanfar, S., M. D. Kulkarni, et al. (1997). "High resolution imaging of in vivo cardiac dynamics using color Doppler optical coherence tomography." *Optics Express* 1 (13) : 424-431.

Yazdanfar, S., A. M. Rollins, et al. (2000). "Imaging and velocimetry of the human retinal circulation with color Doppler optical coherence tomography." *Optics Letters* 25(19): 1448-1450.

Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.

Yazdanfar, S., A. M. Rollins, et al. (2003). "In vivo imaging of human retinal flow dynamics by color Doppler optical coherence tomography." *Archives of Ophthalmology* 121(2): 235-239.

Yazdanfar, S., C. H. Yang, et al. (2005). "Frequency estimation precision in Doppler optical coherence tomography using the Cramer-Rao lower bound." *Optics Express* 13(2): 410-416.

Yun, S. H., C. Boudoux, et al. (2004). "Extended-cavity semiconductor wavelength-swept laser for biomedical imaging." *Ieee Photonics Technology Letters* 16(1): 293-295.

Yun, S. H., C. Boudoux, et al. (2003). "High-speed wavelength-swept semiconductor laser with a polygon-scanner-based wavelength filter." *Optics Letters* 28(20): 1981-1983.

Yun, S. H., G. J. Tearney, et al. (2004). "Pulsed-source and swept-source spectral- domain optical coherence tomography with reduced motion artifacts." *Optics Express* 12(23): 5614-5624.

Yun, S. H., G. J. Tearney, et al. (2004). "Removing the depth-degeneracy in optical frequency domain imaging with frequency shifting." *Optics Express* 12(20): 4822-4828.

Yun, S. H., G. J. Tearney, et al. (2004). "Motion artifacts in optical coherence tomography with frequency-domain ranging." *Optics Express* 12(13): 2977-2998.

Zhang, J., J. S. Nelson, et al. (2005). "Removal of a minor image and enhancement of the signal-to-noise ratio in Fourier-domain optical coherence tomography using an electro-optic phase modulator." *Optics Letters* 30(2): 147-149.

Zhang, Y., M. Sato, et al. (2001). "Numerical investigations of optimal synthesis of several low coherence sources for resolution improvement." *Optics Communications* 192(3-6): 183-192.

Zhang, Y., M. Sato, et al. (2001). "Resolution improvement in optical coherence tomography by optimal synthesis of light-emitting diodes." *Optics Letters* 26(4): 205-207.

Zhao, Y., Z. Chen, et al. (2002). "Real-time phase-resolved functional optical coherence tomography by use of optical Hilbert transformation." *Optics Letters* 27(2): 98-100.

Zhao, Y. H., Z. P. Chen, et al. (2000). "Doppler standard deviation imaging for clinical monitoring of in vivo human skin blood flow." *Optics Letters* 25(18): 1358-1360.

Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.

Zhou, D., P. R. Prucnal, et al. (1998). "A widely tunable narrow linewidth semiconductor fiber ring laser." *IEEE Photonics Technology Letters* 10(6): 781-783.

Zuluaga, A. F. and R. Richards-Kortum (1999). "Spatially resolved spectral interferometry for determination of subsurface structure." *Optics Letters* 24(8): 519-521.

Zvyagin, A. V., J. B. FitzGerald, et al. (2000). "Real-time detection technique for Doppler optical coherence tomography." *Optics Letters* 25(22): 1645-1647.

Marc Nikles et al., "Brillouin gain spectrum characterization in single-mode optical fibers", *Journal of Lightwave Technology* 1997, 15 (10): 1842-1851.

Tsuyoshi Sonehara et al., "Forced Brillouin Spectroscopy Using Frequency-Tunable Continuous-Wave Lasers", *Physical Review Letters* 1995, 75 (23): 4234-4237.

Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.

Webb RH et al. "Confocal Scanning Laser Ophthalmoscope", *Applied Optics* 1987, 26 (8): 1492-1499.

Andreas Zumbusch et al. "Three-dimensional vibrational imaging by coherent anti-Stokes Raman scattering", *Physical Review Letters* 1999, 82 (20): 4142-4145.

Katrin Kneipp et al., "Single molecule detection using surface-enhanced Raman scattering (SERS)", *Physical Review Letters* 1997, 78 (9): 1667-1670.

K.J. Koski et al., "Brillouin imaging" *Applied Physics Letters* 87, 2005.

Boas et al., "Diffusing temporal light correlation for burn diagnosis", *SPIE*, 1999, 2979:468-477.

David J. Briers, "Speckle fluctuations and biomedical optics: implications and applications", *Optical Engineering*, 1993, 32(2):277-283.Clark et al., "Tracking Speckle Patterns with Optical Correlation", *SPIE*, 1992, 1772:77-87.

Clark et al., "Tracking Speckle Patterns with Optical Correlation", *SPIE*, 1992, 1772:77-87.

Facchini et al., "An endoscopic system for DSPI", *Optik*, 1993, 95(1):27-30.

Hrabovsky, M., "Theory of speckle dispacement and decorrelation: application in mechanics", *SPIE*, 1998, 3479:345-354.

Sean J. Kirkpatrick et al., "Micromechanical behavior of cortical bone as inferred from laser speckle data", *Journal of Biomedical Materials Research*, 1998, 39(3):373-379.

Sean J. Kirkpatrick et al., "Laser speckle microstrain measurements in vascular tissue", *SPIE*, 1999, 3598:121-129.

Loree et al., "Mechanical Properties of Model Atherosclerotic Lesion Lipid Pools", *Arteriosclerosis and Thrombosis*, 1994, 14(2):230-234.

Podbielska, H. "Interferometric Methods and Biomedical Research", *SPIE*, 1999, 2732:134-141.

Richards-Kortum et al., "Spectral diagnosis of atherosclerosis using an optical fiber laser catheter", *American Heart Journal*, 1989, 118(2):381-391.

Ruth, B. "blood flow determination by the laser speckle method", *Int J Microcirc: Clin Exp*, 1990, 9:21-45.

Shapo et al., "Intravascular strain imaging: Experiments on an Inhomogeneous Phantom", *IEEE Ultrasonics Symposium* 1996, 2:1177-1180.

Shapo et al., "Ultrasonic displacement and strain imaging of coronary arteries with a catheter array", *IEEE Ultrasonics Symposium* 1995, 2:1511-1514.

Thompson et al., "Imaging in scattering media by use of laser speckle", *Opt. Soc. Am. A.*, 1997, 14(9):2269-2277.

Thompson et al., "Diffusive media characterization with laser speckle", *Applied Optics*, 1997, 36(16):3726-3734.

Tuchin, Valery V., "Coherent Optical Techniques for the Analysis of Tissue Structure and Dynamics," *Journal of Biomedical Optics*, 1999, 4(1):106-124.

M. Wussling et al., "Laser diffraction and speckling studies in skeletal and heart muscle", *Biomed, Biochim, Acta*, 1986, 45(1/2):S 23- S 27.

T. Yoshimura et al., "Statistical properties of dynamic speckles", *J. Opt. Soc. Am A*. 1986, 3(7):1032-1054.

Zimnyakov et al., "Spatial speckle correlometry in applications to tissue structure monitoring", *Applied Optics* 1997, 36(22): 5594-5607.

Zimnyakov et al., "A study of statistical properties of partially developed speckle fields as applied to the diagnosis of structural changes in human skin", *Optics and Spectroscopy*, 1994, 76(5): 747-753.

Zimnyakov et al., "Speckle patterns polarization analysis as an approach to turbid tissue structure monitoring", *SPIE* 1999, 2981:172-180.

Ramasamy Manoharan et al., "Biochemical analysis and mapping of atherosclerotic human artery using FT-IR microspectroscopy", *Atherosclerosis*, May 1993, 181-1930.

N.V. Salunke et al., "Biomechanics of Atherosclerotic Plaque" *Critical Reviews™ in Biomedical Engineering* 1997, 25(3):243-285.

D. Fu et al., "Non-invasive quantitative reconstruction of tissue elasticity using an iterative forward approach", Phys. Med. Biol. 2000 (45): 1495-1509.

S.B. Adams Jr. et al., "The use of polarization sensitive optical coherence tomography and elastography to assess connective tissue", Optical Soc. of American Washington 2002, p. 3.

Erdelyi et al. "Generation of diffraction-free beams for applications in optical microlithography", J. Vac. Sci. Technol. B 15 (12) Mar./Apr. 1997, pp. 287-292.

Tearney et al., "Spectrally encoded miniature endoscopy" Optical Society of America; Optical Letters vol. 27, No. 6, Mar. 15, 2002; pp. 412-414.

Yelin et al., "Double-clad Fiber for Endoscopy" Optical Society of America; Optical Letters vol. 29, No. 20, Oct. 16, 2005; pp. 2408-2410.

PCT International Preliminary Report on Patentability for International Application No. PCT/US2004/038404 dated Jun. 2, 2006.

Office Action dated Aug. 24, 2006 for U.S. Appl. No. 10/137,749.

Barry Cense et al., "Spectral-domain polarization-sensitive optical coherence tomography at 850nm", Coherence Domain Optical Methods and Optical Coherence Tomography in Biomedicine IX, 2005, pp. 159-162.

A. Ymeti et al., "Integration of microfluidics with a four-channel integrated optical Young interferometer immunosensor", Biosensors and Bioelectronics, Elsevier Science Publishers, 2005, pp. 1417-1421.

PCT International Search Report for Application No. PCT/US2006/018865 filed May 5, 2006.

International Written Opinion for International Patent application No. PCT/US2006/018865 filed May 5, 2006.

John M. Poneros, "Diagnosis of Barrett's esophagus using optical coherence tomography", Gastrointestinal Endoscopy clinics of North America, 14 (2004) pp. 573-588.

P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.

Ko T et al., "Ultrahigh resolution in vivo versus ex vivo OCT imaging and tissue preservation", Conference on Lasers and electro-optics, 2001, pp. 252-253.

Paul M. Ripley et al., "A comparison of Artificial Intelligence techniques for spectral classification in the diagnosis of human pathologies based upon optical biopsy", Journal of Optical Society of America, 2000, pp. 217-219.

Wolfgang Drexler et al., "Ultrahigh-resolution optical coherence tomography", Journal of Biomedical Optics Spie USA, 2004, pp. 47-74.

PCT International Search Report for Application No. PCT/US2006/016677 filed Apr. 28, 2006.

International Written Opinion for International Patent application No. PCT/US2006/016677 filed Apr. 28, 2006.

Fernandez, Cabrera Delia et al. "Automated detection of retinal layer structures on optical coherence tomography images", *Optics Express* vol. 13, No. 25, Oct. 4, 2005, pp. 10200-10216.

Ishikawa, Hiroshi et al. "Macular Segmentation with optical coherence tomography", Investigative Ophthalmology & Visual Science, vol. 46, No. 6, Jun. 2005, pp. 2012-2017.

Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.

PCT International Search Report and Written Opinion for Application No. PCT/US2006/031905 dated May 3, 2007.

PCT International Search Report and Written Opinion for Application No. PCT/US2007/060481 dated May 23, 2007.

PCT International Search Report and Written Opinion for Application No. PCT/US2007/060717 dated May 24, 2007.

PCT International Search Report and Written Opinion for Application No. PCT/US2007/060319 dated Jun. 6, 2007.

D. Yelin et al., "Three-dimensional imaging using spectral encoding heterodyne interferometry", Optics Letters, Jul. 15, 2005, vol. 30, No. 14, pp. 1794-1796.

Akiba, Masahiro et al. "En-face optical coherence imaging for three-dimensional microscopy", SPIE, 2002, pp. 8-15.

Office Action dated Aug. 10, 2007 for U.S. Appl. No. 10/997,789.

Office Action dated Feb. 2, 2007 for U.S. Appl. No. 11/174,425.

PCT International Search Report and Written Opinion for Application No. PCT/US2007/060657 dated Aug. 13, 2007.

Joo, Chulmin et al., Spectral-domain optical coherence phase microscopy for quantitative phase-contrast imaging, Optics Letters, Aug. 15, 2005, vol. 30, No. 16, pp. 2131-2133.

Guo, Bujin et al., "Laser-based mid-infrared reflectance imaging of biological tissues", Optics Express, Jan. 12, 2004, vol. 12, No. 1, pp. 208-219.

Office Action dated Mar. 28, 2007 for U.S. Appl. No. 11/241,907.

Office Action dated May 23, 2007 for U.S. Appl. No. 10/406,751.

Office Action dated May 23, 2007 for U.S. Appl. No. 10/551,735.

PCT International Search Report and Written Opinion for Application No. PCT/US2007/061815 dated Aug. 2, 2007.

Sir Randall, John et al., "Brillouin scattering in systems of biological significance", Phil. Trans. R. Soc. Lond. A 293, 1979, pp. 341-348.

Takagi, Yasunari, "Application of a microscope to Brillouin scattering spectroscopy", Review of Scientific Instruments, No. 12, Dec. 1992, pp. 5552-5555.

Lees, S. et al., "Studies of Compact Hard Tissues and Collagen by Means of Brillouin Light Scattering", Connective Tissue Research, 1990, vol. 24, pp. 187-205.

Berovic, N. "Observation of Brillion scattering from single muscle fibers", European Biophysics Journal, 1989, vol. 17, pp. 69-74.

PCT International Search Report and Written Opinion for Application No. PCT/US2007/062465 dated Aug. 8, 2007.

Pyhtila John W. et al., "Rapid, depth-resolved light scattering measurements using Fourier domain, angle-resolved low coherence interferometry", Optics Society of America, 2004.

Pyhtila John W. et al., "Determining nuclear morphology using an improved angle-resolved low coherence interferometry system", Optics Express, Dec. 15, 2003, vol. 11, No. 25, pp. 3473-3484.

Desjardins A.E., et al., "Speckle reduction in OCT using massively-parallel detection and frequency-domain ranging", Optics Express, May 15, 2006, vol. 14, No. 11, pp. 4736-4745.

Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-8.

PCT International Search Report and Written Opinion for Application No. PCT/US2007/066017 dated Aug. 30, 2007.

Yamanari M. et al., "Polarization sensitive Fourier domain optical coherence tomography with continuous polarization modulation", Proc. of SPIE, vol. 6079, 2006.

Zhang Jun et al., "Full range polarization-sensitive Fourier domain optical coherence tomography", Optics Express, Nov. 29, 2004, vol. 12, No. 24, pp. 6033-6039.

European Patent Office Search report for Application No. 01991092.6-2305 dated Jan. 12, 2006.

PCT International Search Report and Written Opinion for Application No. PCT/US2007/060670 dated Sep. 21, 2007.

Office Action dated Oct. 11, 2007 for U.S. Appl. No. 11/534,095.

Office Action dated Oct. 9, 2007 for U.S. Appl. No. 09/709,162.

Notice of Allowance dated Oct. 3, 2007 for U.S. Appl. No. 11/225,840.

Siavash Yazdanfar et al., "In Vivo imaging in blood flow in human retinal vessels using color Doppler optical coherence tomography", SPIE, 1999 vol. 3598, pp. 177-184.

Office Action dated Oct. 30, 2007 for U.S. Appl. No. 11/670,069.

Office Action dated Nov. 13, 2006 for U.S. Appl. No. 10/501,268.

Office Action dated Nov. 20, 2006 for U.S. Appl. No. 09/709,162.

PCT International Search Report and Written Opinion for Application No. PCT/US2004/023585 filed Jul. 23, 2004.

International Search Report and Written Opinion dated Feb. 24, 2009 for PCT/US2008/076447.

Gelikono, V.M. et al. (Oct. 2004) Two-Wavelength Optical Coherence Tomography Radio physics and Quantum Electronics, Kluwe Academic Publishers-Consultants. vol. 47, No. 10-1.

J.M. Schmitt et al., (1999) "Speckle in Optical Coherence Tomography: An overview", SPIE vol. 3726, pp. 450-461.

Lewis, Neil E. et al., (1997) "Applications of Fourier Transform Infrared Imaging Microscopy in Neurotoxicity", Annals New York Academy of Sciences, pp. 234-246.

Yabushita, H. B., et al. (2002) "Measurement of Thin Fibrous Caps in Atherosclerotic Plaques by Optical Coherence Tomography." American Heart Association, INC, Circulation 2002;106;1640.

Smith, P. J. M., E.M.; Taylor, C.M.; Selviah, D.R.; Day, S.E.; Commander, L.G. (2000) "Variable-Focus Microlenses as a Potential Technology for Endoscopy." SPIE (vol. 3919), USA pp. 187-192.

* cited by examiner

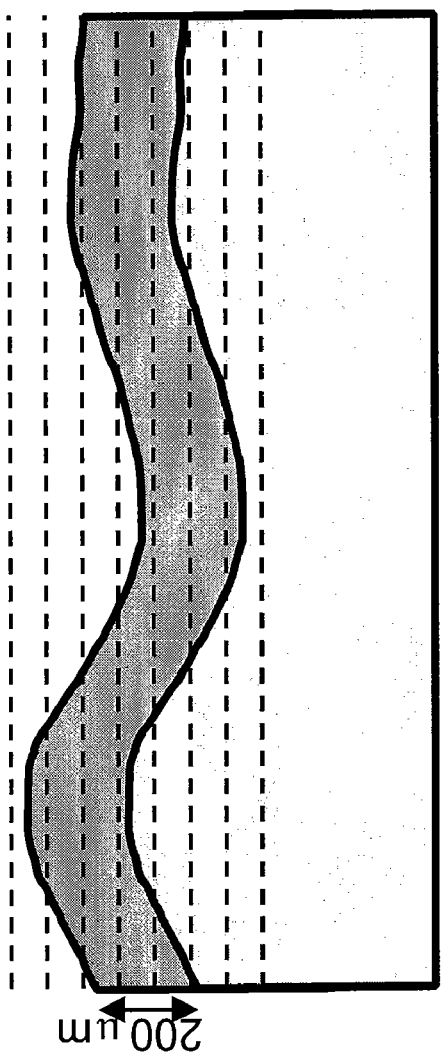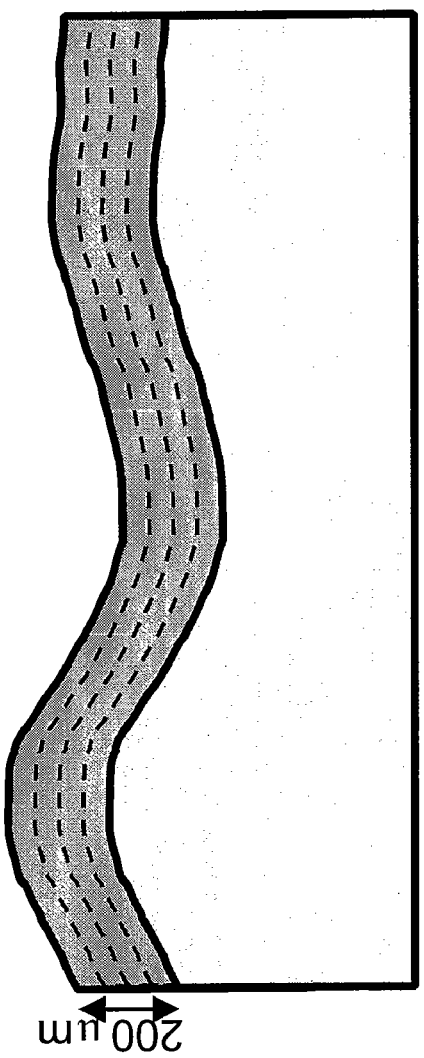
FIG. 13A
FIG. 13B

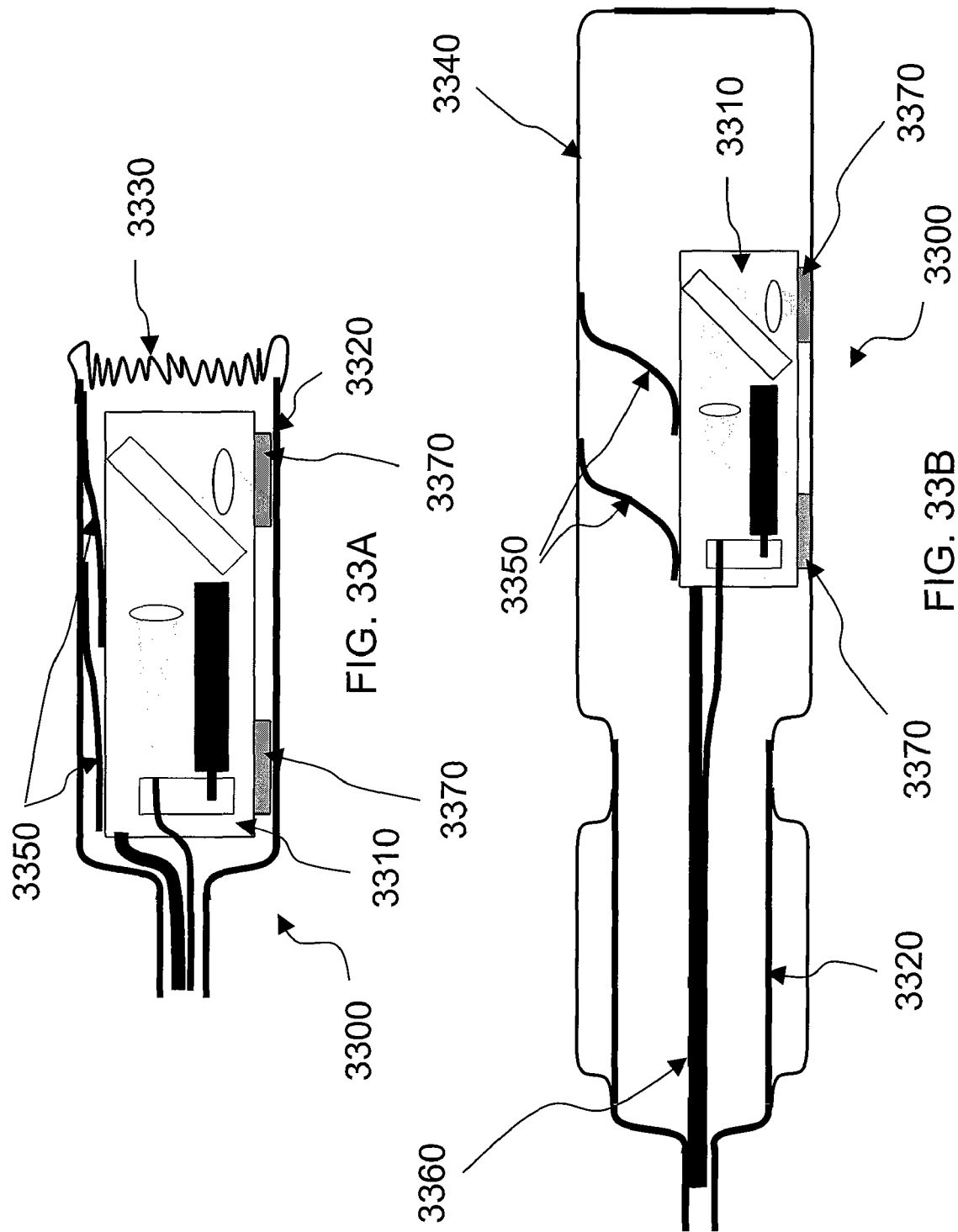

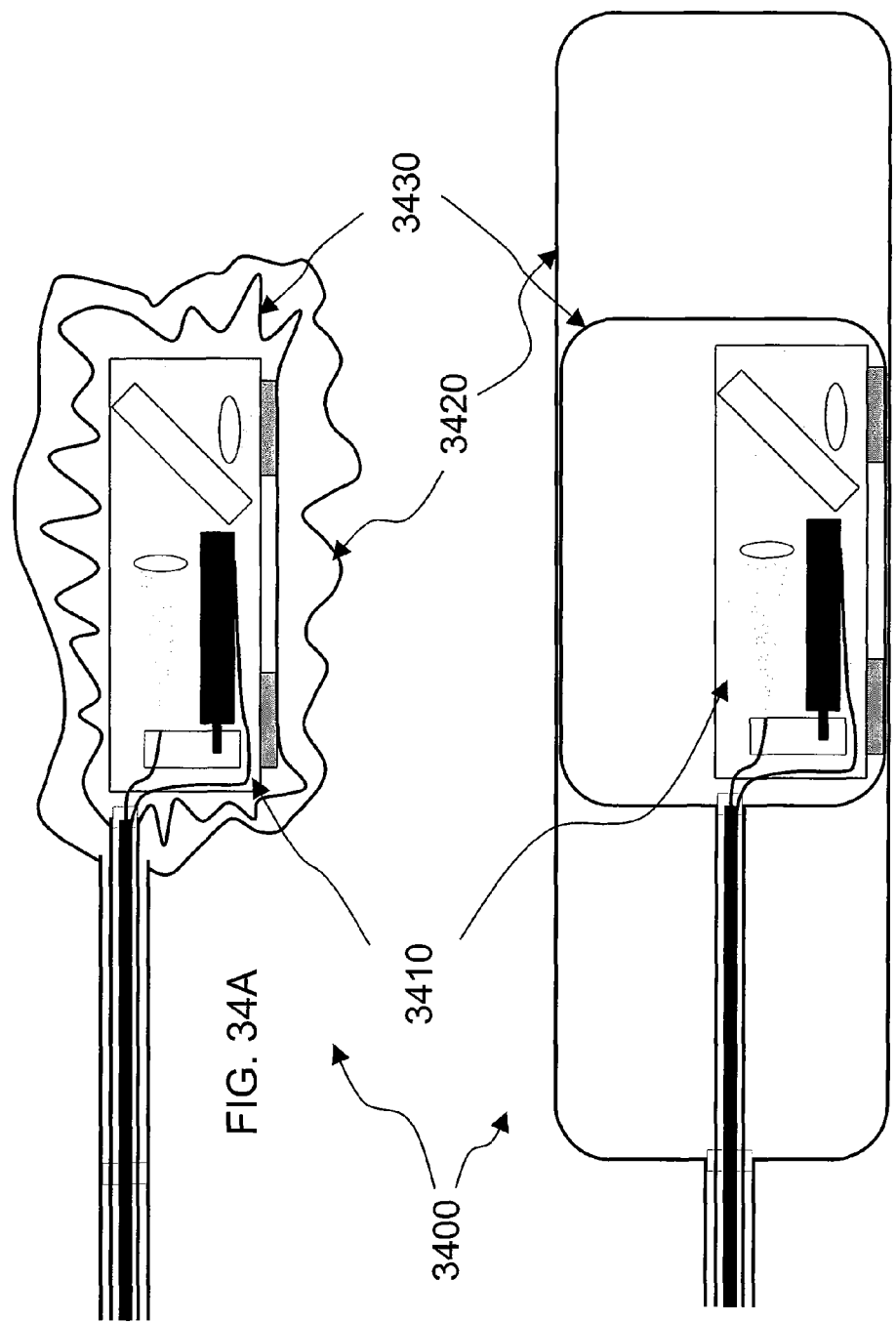

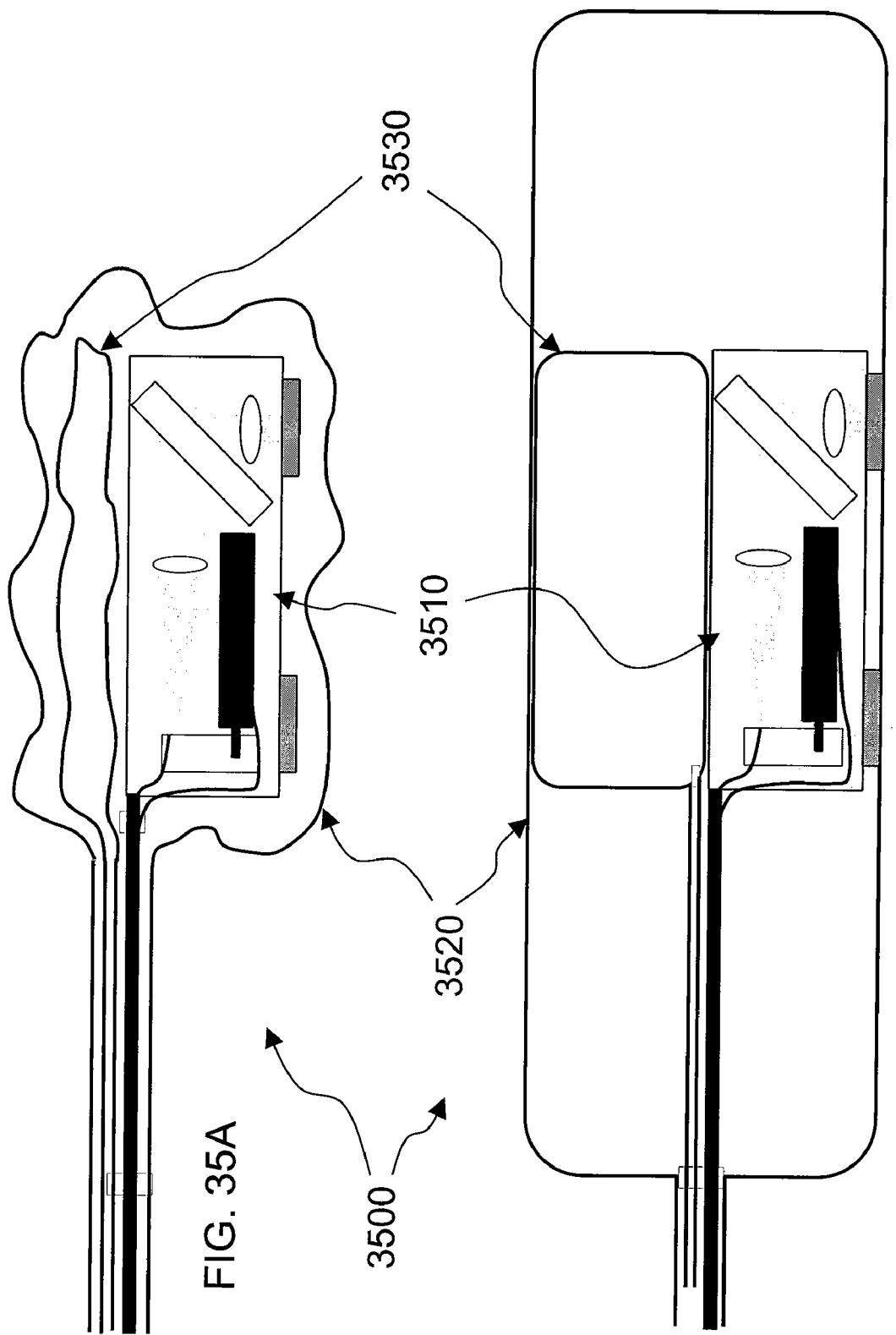

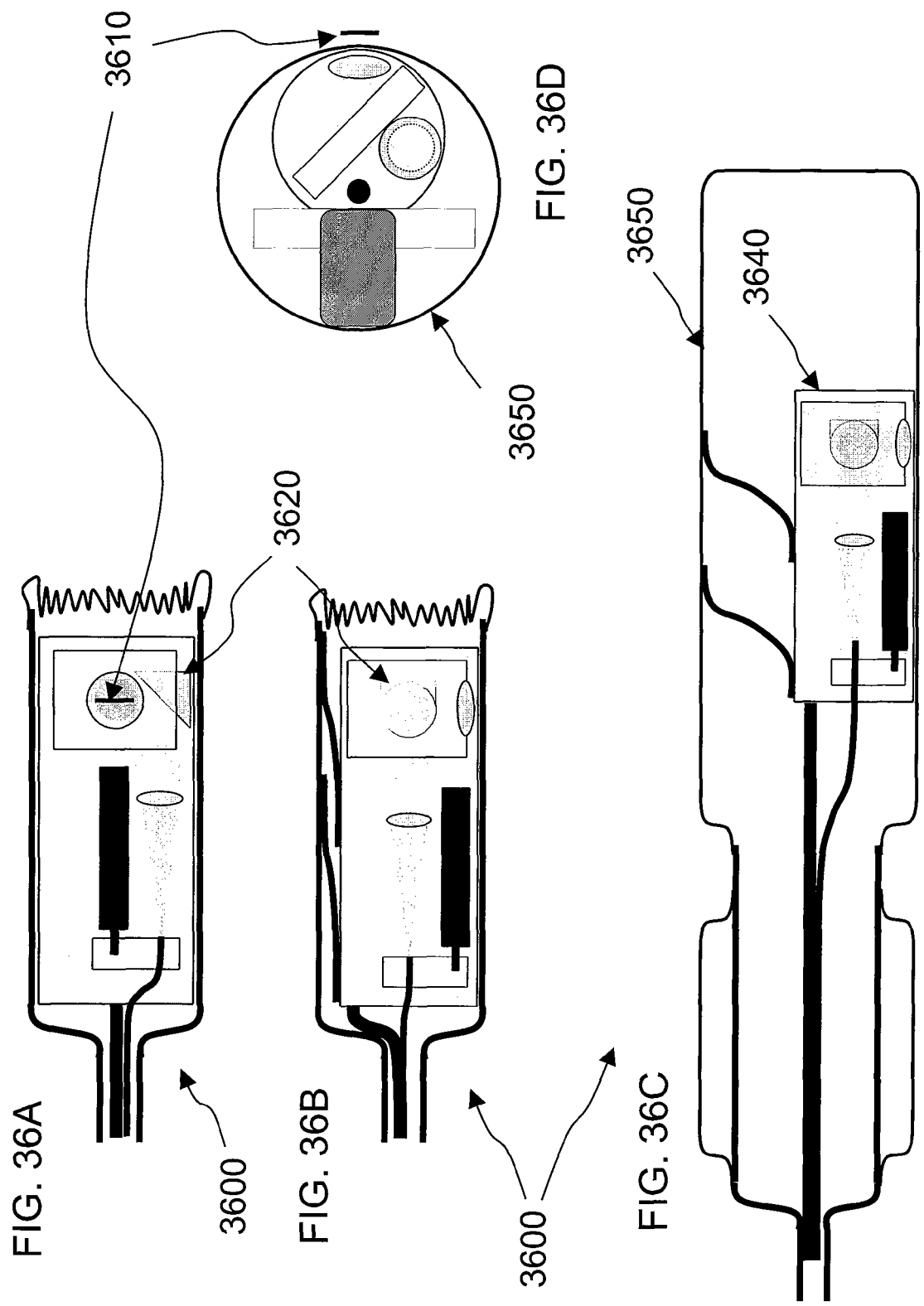

METHOD AND APPARATUS FOR OPTICAL IMAGING VIA SPECTRAL ENCODING

CROSS-REFERENCE TO RELATED APPLICATION(S)

This application is based upon and claims the benefit of priority from U.S. Patent Application Ser. No. 60/721,802, filed Sep. 29, 2005, the entire disclosure of which is incorporated herein by reference.

FIELD OF THE INVENTION

The present invention relates to devices and methods for comprehensive optical imaging of epithelial organs and other biological structures via spectral encoding.

BACKGROUND OF THE INVENTION

Radiological techniques such as X-ray computed tomography ("CT"), magnetic resonance imaging ("MRI"), and ultrasound can enable noninvasive visualization of human pathology at the organ level. Although these modalities may be capable of identifying large-scale pathology, the diagnosis of cancer can require the evaluation of microscopic structures that is beyond the resolution of conventional imaging techniques. Consequently, biopsy and histopathologic examination may be required for diagnosis. Because precancerous growth and early stage cancers often arise on a microscopic scale, they can present significant challenges for identification and diagnosis. Conventional screening and surveillance of these pathologies relies on unguided biopsy and morphological analysis of Hematoxylin and Eosin ("H&E") stained slides. Although this approach may be regarded as a current standard for microscopic diagnosis, it requires the removal of tissue from the patient and significant processing time to generate slides. More importantly, histopathology is inherently a point sampling technique; frequently only a very small fraction of the diseased tissue can be excised and often less than 1% of a biopsy sample may be examined by a pathologist.

It may be preferable to obtain microscopic diagnoses from an entire organ or biological system in a living human patient. However, the lack of an appropriate imaging technology can greatly limits options for screening for pre-neoplastic conditions (e.g. metaplasia) and dysplasia. In addition, an inability to identify areas of dysplasia and carcinoma in situ has led to screening procedures such as, e.g., random biopsy of the prostate, colon, esophagus, and bladder, etc., which can be highly undesirable and indiscriminate. Many diagnostic tasks presently referred to a frozen section laboratory, such as the delineation of surgical tumor margins, could be improved by a diagnostic modality capable of rapidly imaging large tissue volumes on a microscopic scale. A technology that could fill this gap between pathology and radiology would be of great benefit to patient management and health care.

Technical advances have been made to increase the resolution of non-invasive imaging techniques such as, e.g., micro-CT, micro-PET, and magnetic resonance imaging ("MRI") microscopy. Resolutions approaching 20 µm have been achieved by these technologies, but fundamental physical limitations can still prevent their application in patients. Microscopic optical biopsy techniques, performed in situ, have recently been advanced for non-excisional histopathologic diagnosis. Reflectance confocal microscopy ("RCM") may be particularly well-suited for non-invasive microscopy in patients, as it is capable of measuring microscopic structure without tissue contact and does not require the administration of extrinsic contrast agents. RCM can reject out of focus light and detects backscattered photons selectively originating from a single plane within the tissue. RCM can be implemented, e.g., by rapidly scanning a focused beam of electromagnetic radiation in a plane parallel to a tissue surface, yielding transverse or en face images of tissue. The large numerical aperture (NA) that may be used in RCM can yield a very high spatial resolution (1-2 µm), enabling visualization of subcellular structures. High NA imaging, however, can be particularly sensitive to aberrations that arise as light propagates through inhomogeneous tissue. Also, high-resolution imaging with RCM is typically limited to a depth of about 100-400 µm.

RCM has been extensively demonstrated as a viable imaging technique for skin tissue. Development of endoscopic confocal microscopy systems has been more difficult, owing at least in part to the substantial technical challenges involved in miniaturizing a scanning microscope. One major obstacle to direct application of the concepts of confocal microscopy to endoscopy is the engineering of a mechanism for rapidly rastering a focused beam at the distal end of a small-diameter, flexible probe. A variety of approaches have been proposed to address this problem, including the use of distal micro-electromechanical systems ("MEMS") beam scanning devices and proximal scanning of single-mode fiber bundles. Also, RCM may provide microscopic images only at discrete locations—a "point sampling" technique. As currently implemented, point sampling can be inherent to RCM because it has a limited field of view, which may be comparable to or less than that of an excisional biopsy, and the imaging rate can be too slow for comprehensive large field microscopy.

Another challenge in adapting confocal microscopy to endoscopic applications can include miniaturization of high NA objectives that may be used for optical sectioning. Such miniaturization may be achieved by providing, e.g., a gradient-index lens system, dual-axis objectives, or custom designs of miniature objectives. For example, detailed images of the morphology of cervical epithelium may be obtained in vivo using a fiber optic bundle coupled to a miniature objective lens, and fluorescence-based images of colorectal lesions may be achieved using commercial instruments such as those which may be obtained, e.g., from Olympus Corp. and Pentax/Optiscan.

Despite these advances, there may be a need for improved imaging techniques that can provide microscopic resolution of biological structures in situ over large regions.

OBJECTS AND SUMMARY OF THE INVENTION

One of the objects of the present invention is to overcome certain deficiencies and shortcomings of the prior art systems and methods (including those described herein above), and provide an exemplary embodiment of a method and an apparatus which are capable of providing comprehensive microscopic optical imaging of a sample such as, e.g., an anatomical structure, an epithelial organ or other bodily tissue.

For example, an apparatus in accordance with exemplary embodiments of the present invention can be provided which is capable of providing information associated with a sample. The information can be based on first data associated with a region of the sample and second data associated with both a second signal obtained from the sample and a reference signal. The region may be less than about 10 microns in length. A two- or three-dimensional image of the region may be generated using the information. Optionally, the first and second data can be obtained essentially simultaneously, and they each may be associated with a common location on the sample.

The apparatus can be provided in a form of a probe or a single enclosure. In exemplary embodiments of the present invention, the apparatus may include a positioning arrangement configured to position the probe or enclosure at a particular location relative to the sample based on the first and/or second data. Certain common components such as, e.g., optical components, may be used to obtain the first and second data. These common components can include, for example, a source and/or detector of light or other radiation.

In exemplary embodiments of the present invention, the first data can include confocal microscopy information including, e.g., reflectance confocal microscopy information, and/or spectral encoding microscopy information. The second data can include optical coherence tomography information. A light source having a plurality of wavelengths and/or wavelengths that can vary with time may be used to obtain the second data, which may be further based on an interference between a signal obtained form the sample and a reference sample.

In certain exemplary embodiments of the present invention, the apparatus can be configured to control a position of the probe or enclosure relative to the sample based on the first and/or second data.

In a further exemplary embodiment of the present invention, separate images may be generated using the first and second data, and these images may be associated with one another based on locations on the sample that the first and second data may be associated with.

For example, the apparatus in accordance with exemplary embodiments of the present invention can include a focusing arrangement capable of controlling a focal length and/or position associated with confocal microscopy information, spectral encoding microscopy information, and/or optical coherence tomography information.

Other features and advantages of the present invention will become apparent upon reading the following detailed description of embodiments of the invention, when taken in conjunction with the appended claims.

BRIEF DESCRIPTION OF THE DRAWINGS

Further objects, features and advantages of the present invention will become apparent from the following detailed description taken in conjunction with the accompanying figures showing illustrative embodiments of the present invention, in which:

FIG. 13A is an illustration of an exemplary technique which may be used to acquire the desired depth range by stepping through a range of focal depths;

FIG. 13B is an illustration of an exemplary technique which may be used for imaging tissue at a particular depth by actively adjusting a focal plane;

FIG. 33A is a schematic illustration of a probe which includes a forward inflatable balloon and an inner housing that is configured to scan while in contact with an inner wall of the balloon;

FIG. 33B is a schematic illustration of the probe shown in FIG. 33A which is in contact with an inner wall of the inflated balloon;

FIG. 34A is a schematic illustration of an exemplary probe that includes an outer inflatable balloon and an inner inflatable balloon which may be configured to maintain contact between the probe and a wall of the outer balloon when inflated;

FIG. 34B is a schematic illustration of the probe shown in FIG. 34A, where the inflated inner balloon is provided around the probe and is configured to maintain contact between the probe and the wall of the inflated outer balloon;

FIG. 35A is a schematic illustration of a further exemplary probe that includes an outer inflatable balloon and an inner inflatable balloon which may be configured to maintain contact between the probe and a wall of the outer balloon when inflated;

FIG. 35B is a schematic illustration of the probe shown in FIG. 35A, where the inflated inner balloon is provided between the probe and the outer balloon and is configured to maintain contact between the probe and the wall of the inflated outer balloon;

FIG. 36A is a schematic illustration of a bottom view of a probe that is configured to scan along a pullback axis while in contact with an inner wall of an inflatable balloon;

FIG. 36B is a schematic illustration of a side view of the probe shown in FIG. 36A;

FIG. 36C is a schematic illustration of a side view of the probe shown in FIG. 36A, where the probe is in contact with the inner wall of the inflated balloon; and FIG. 36D is a front view of the probe shown in FIG. 36C.

Figure 1:
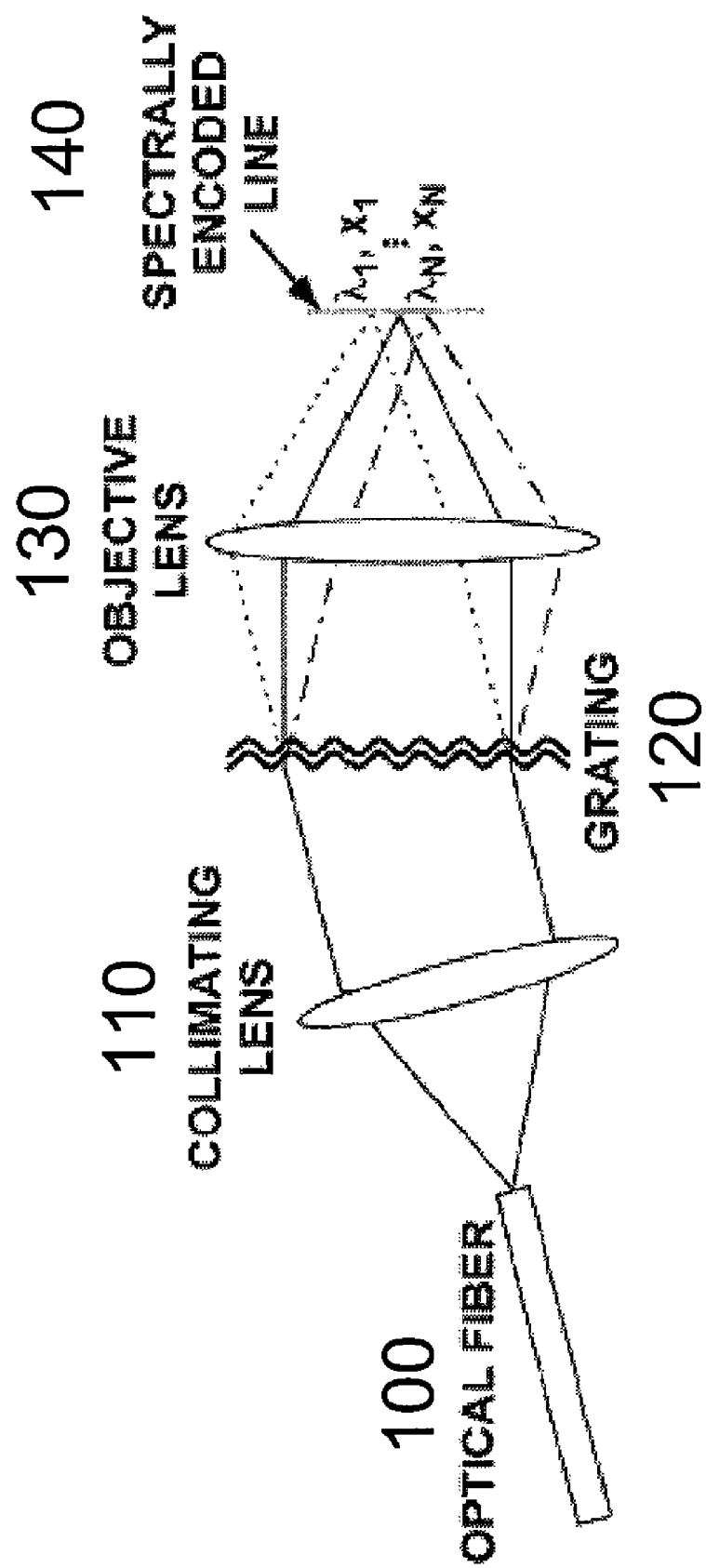
FIG. 1 is a schematic illustration of an exemplary spectrally encoded confocal microscopy (SECM) system.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF EXEMPLARY EMBODIMENTS OF INVENTION

In accordance with exemplary embodiments of the present invention, a method and apparatus for endoscopic confocal microscopy is provided which circumvents the need for miniature, high-speed scanning mechanisms within a probe. Spectrally encoded confocal microscopy ("SECM") is a wavelength-division multiplexed confocal approach that may be used. SECM utilizes a broad bandwidth light source and can encode one dimension of spatial information in the optical spectrum.

An exemplary SECM technique is shown in FIG. 1. The output from a single-mode optical fiber 100, which may be located at a distal end of a probe, can be collimated by a collimating lens 110, and then illuminate a dispersive optical element (such as, e.g., a transmission diffraction grating 120). An objective lens 130 can then focus each diffracted wavelength to a distinct spatial location within the specimen, resulting in a transverse line focus 140 where each point on the line may be characterized by a distinct wavelength. After reflection from the specimen, which may be, e.g., biological tissue, the optical signal can be recombined by the diffraction element 120 and collected by the single-mode fiber 100. The core aperture of the single-mode fiber 100 can provide a spatial filtering mechanism that is capable of rejecting out-of-focus light. Outside the probe (and optionally within a system console) the spectrum of the returned light can be measured and converted into confocal reflectance as a function of transverse displacement within the specimen. The spectral decoding can be performed rapidly. Thus an image created by scanning the beam in a direction orthogonal to the line focus can be accomplished by relatively slow and straightforward mechanical actuation.

SECM techniques may allow the use of endoscopic RCM, and it can be capable of providing image data at extremely high rates using high-speed linear CCD cameras. Commercially available linear CCD arrays can obtain data at a rate greater than about 60 million pixels per second. When incorporated into an SECM spectrometer, these arrays can produce confocal images at speeds that are about 10 times faster than a typical video rate and up to 100 times faster than some endoscopic RCM techniques. The rapid imaging rate and fiber-optic design of typical SECM systems can permit comprehensive, large area microscopy through an endoscopic probe.

Techniques using optical coherence tomography ("OCT") and variations thereof may be used for comprehensive architectural screening. Acquiring an OCT signal in the wavelength domain, rather than in the time domain, can provide orders of magnitude improvement in imaging speed while maintaining excellent image quality. Using spectral domain OCT ("SD-OCT") techniques, high-resolution ranging can be conducted in biological tissue by detecting spectrally resolved interference between a tissue sample and a reference. Because SD-OCT systems can utilize the same high-speed linear CCD's as SECM systems, they can also be capable of capturing images at 60 million pixels/s, which is approximately two orders of magnitude faster than conventional time-domain OCT ("TD-OCT") systems. With this acquisition rate and resolution, SD-OCT systems can provide comprehensive volumetric microscopy at the architectural level in a clinical environment.

The information provided by exemplary SD-OCT and SECM systems can be complementary, and a hybrid platform utilizing both techniques can provide information on the architectural and cellular structure of tissue that may be essential to accurate diagnosis. Although a combination of disparate technologies typically requires extensive engineering and may compromises performance, SECM and SD-OCT systems can share key components, and a high-performance multi-modality system can be provided without substantially increasing complexity or cost of the individual systems.

An SECM system in accordance with certain exemplary embodiments of the present invention can utilize a wavelength-swept 1300 nm source and a single-element photodetector to obtain spectrally encoded information as a function of time. With this system, images can be acquired at rates of up to about 30 frames/second having high lateral (1.4 µm) and axial (6 µm) resolutions, over a 400 µm field of view ("FOV"). Images of freshly excised swine duodenum segments were imaged ex vivo with a high speed system to illustrate the capability of an SECM system to identify subcellular structures that may be found in, e.g., specialized intestinal metaplasia ("SIM") or the metaplastic change of Barretts esophagus.

Figures 2A, 2B, 2C:
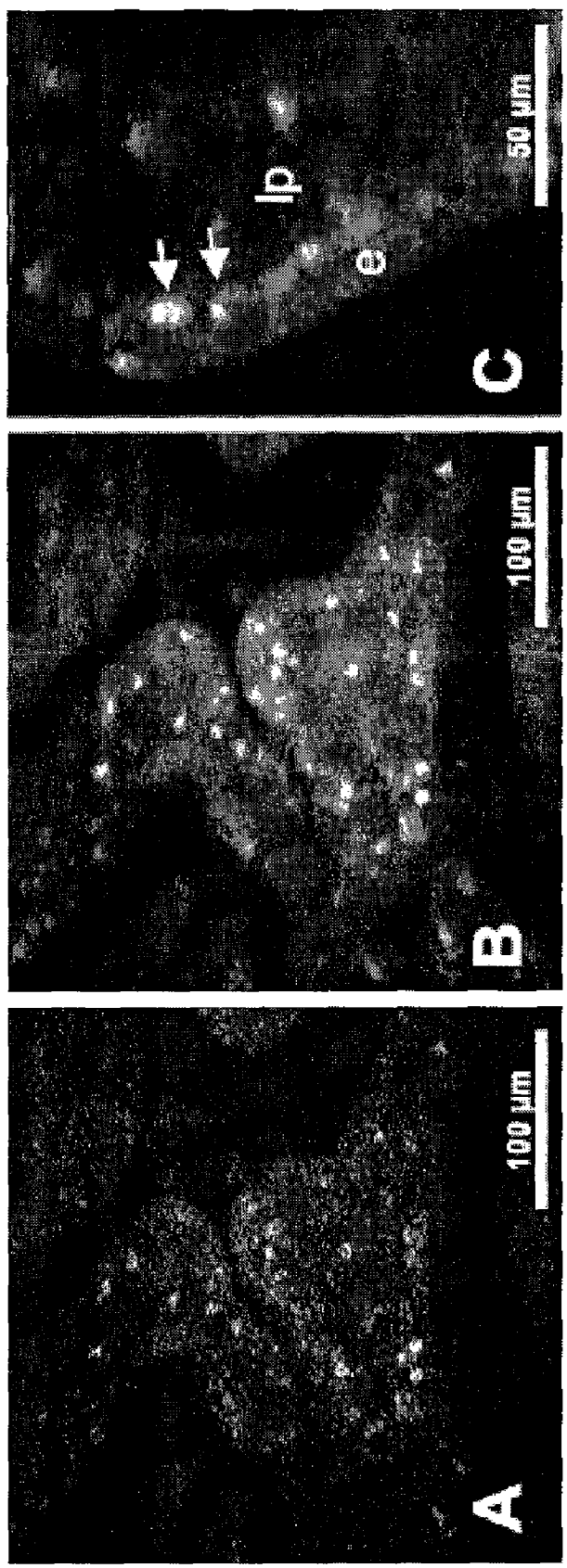
FIG. 2A is an exemplary SECM image of a swine intestinal epithelium, obtained ex vivo, 100 µm from the tissue surface using a single mode source and single-mode detection (SM-MM) configuration.
FIG. 2B is another exemplary SECM image of a swine intestinal epithelium, obtained using a single-mode source and multi-mode detection (SM-MM) configuration.
FIG. 2C is a magnified view of an SECM image of a swine intestinal epithelium.

FIGS. 2A-2C depict exemplary SECM images of a swine intestinal epithelium obtained ex vivo using two imaging modes and corresponding fiber configurations: a single-mode illumination with single-mode detection ("SM-SM"), and a single-mode illumination with multi-mode detection ("SM-MM"). The SM-SM image in FIG. 2A shows the epithelium structure located 100 µm from the tissue surface using a single mode source and single-mode detection. The image of the same tissue region shown in FIG. 2B, obtained using a using a single mode source and multi-mode detection (SM-MM) with a core:aperture ratio of 1:4, may have a smoother appearance and may be more easily interpreted because of a reduction in speckle noise. FIG. 2C is a magnified view of the image shown in FIG. 2B that indicates a presence of villi containing a poorly reflecting core (e.g., lamina propria or "lp") and a more highly scattering columnar epithelium. Bright image densities visible at the base of the columnar cells, consistent with nuclei (indicated by arrows) are shown in FIG. 2C.

Figures 3A, 3B:
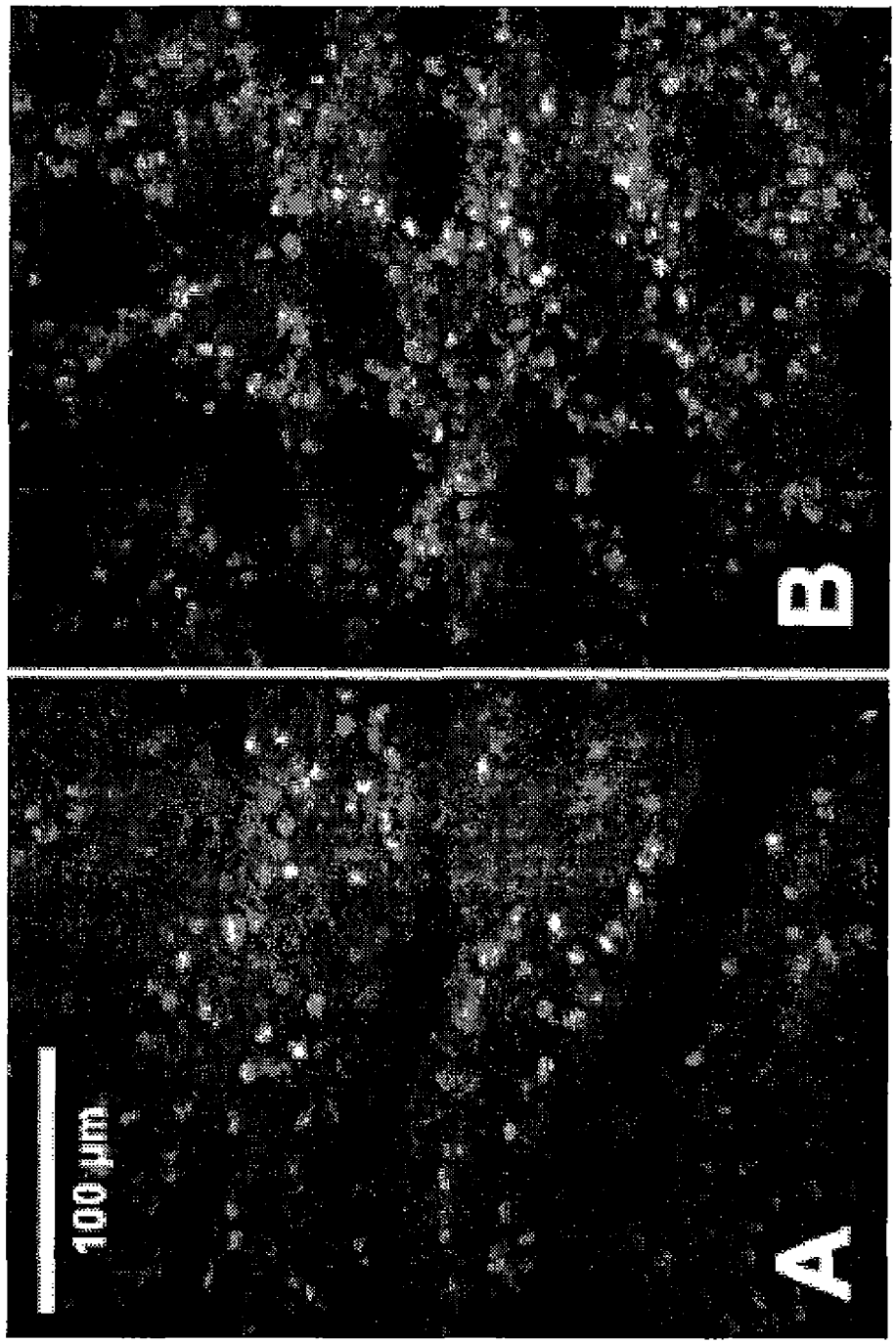
FIG. 3A is an exemplary SECM image of a swine intestinal epithelium, obtained ex vivo, after compression of the bowel wall at an imaging depth of 50 µm.
FIG. 3B is an exemplary SECM image of a swine intestinal epithelium, obtained ex vivo, after compression of the bowel wall at an imaging depth of 100 µm.

The thickness of an esophageal wall being imaged in vivo using OCT techniques can be decreased, e.g., by about a factor of two using an inflated balloon. The swine intestinal sample thickness shown in FIGS. 2A-2C was decreased by the same amount, and the subcellular features observed using SECM techniques were well preserved. FIGS. 3A and 3B show images of this thinned sample obtained at a depth of 50 µm and 100 µm, respectively.

The penetration depth of a commercial 800 nm laser scanning confocal microscope was observed to be reduced by about 20% as compared to that obtained with a 1300 nm SECM system. This reduced penetration may be a result of increased scattering of the shorter wavelength source. Thus an SECM system using an 840 nm source may provide sufficient penetration to identify subcellular structure of, e.g., an intestinal epithelium.

Figure 4:
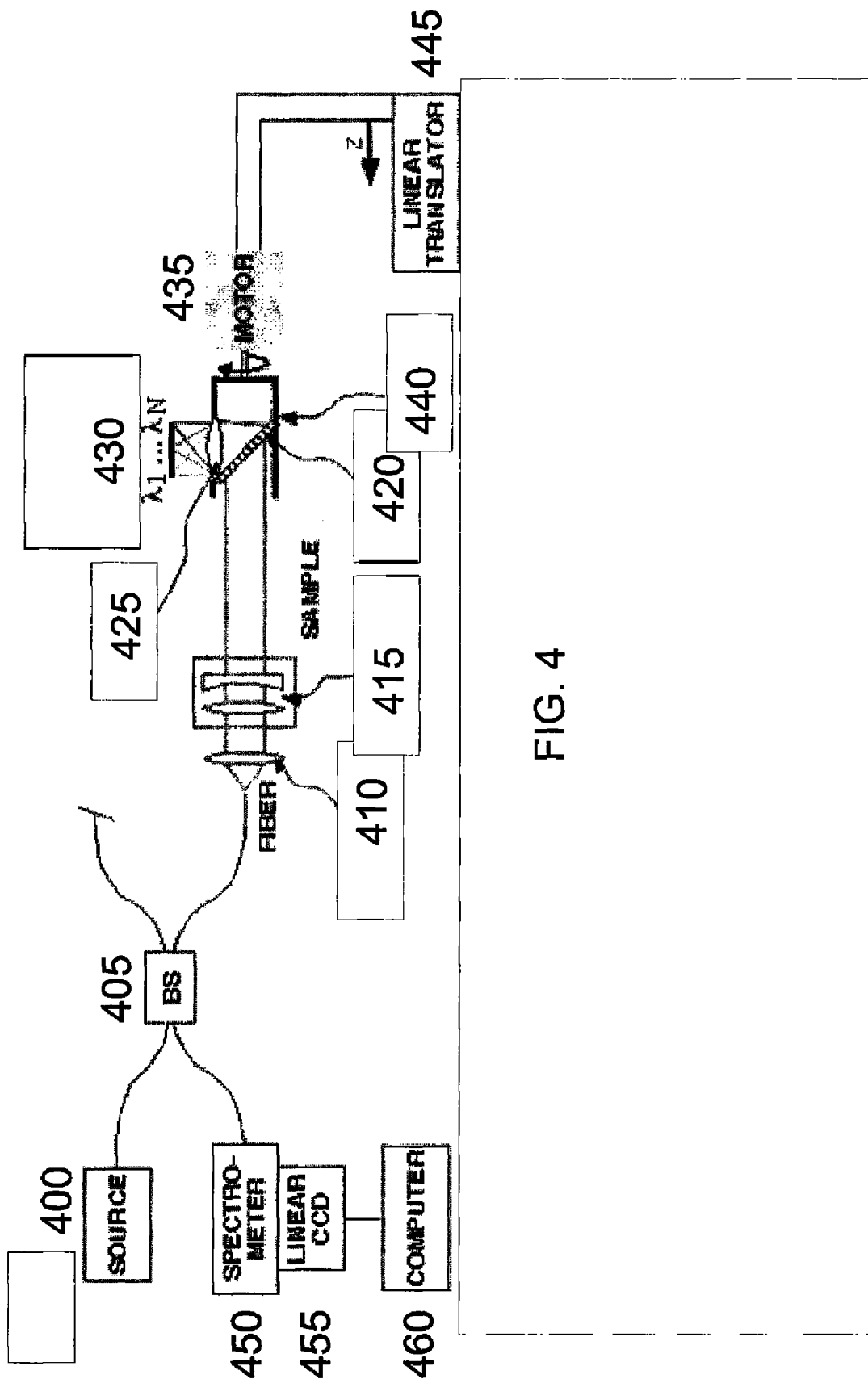
FIG. 4 is a schematic illustration of an exemplary SECM apparatus.

An apparatus in accordance with certain exemplary embodiments of the present invention that is configured to provide comprehensive SECM images is illustrated schematically in FIG. 4. This exemplary apparatus can be configured to obtain images from a cylindrical sample having a length of 2.5 cm and a diameter of 2.0 cm, which are approximately the dimensions of the distal esophagus. A fiber-coupled 2.0 mW superluminescent diode 200, having a wavelength centered at 800 nm and a bandwidth of 45 nm (QSSL- 790-2, qPhotonics, Chesapeake, Va.) can be configured to illuminate a 50/50 single-mode fiber optic beam splitter 405. Light transmitted through one port of the splitter can be collimated by a collimator 410 and transmitted through a fiber 412 to a focusing apparatus 415 and to a grating-lens pair that includes a grating 420 (1780 1 pmm, Holographix, LLC, Hudson, Mass.) and a 350230-B asphere lens 425 (Thor Labs, Inc., Newton, N.J.) having a focal length, f, of 4.5 mm, a clear aperture of 5.0 mm, and a NA of 0.55. This arrangement can be capable of producing a 500 µm longitudinal linear array, or line, of focused, spectrally-encoded spots 430 on an interior surface of the cylindrical sample. The grating-lens pair may be affixed to a shaft of a motor 435 (e.g., a 1516SR, 15 mm diameter motor obtained from MicroMo Electronics, Inc., Clearwater, Fla.) by a housing 440. As the motor 435 rotates, the spectrally encoded line can be scanned across the inner circumference of the cylindrical sample. The motor 435, housing 440, and grating-lens pair may be translated along a longitudinal axis of the cylindrical sample during rotation of the motor 435 using, e.g., a computer-controlled linear stage 445 (such as, e.g., a Nanomotion II, 2.5 cm range, obtained from Melles Griot, Rochester, N.Y.). This procedure produced a helical scan of the entire interior surface of the cylindrical sample.

Light reflected from the sample can be transmitted back through the optical system into the single-mode fiber 412 and provided by the fiber 412 to a spectrometer 450 and linear CCD 455 that can include, e.g., 2048 pixels and has a 30 kHz line rate (such as, e.g., a Basler L104K, obtained from Basler Vision Technologies, Exton, Pa.). A computer 460 can be used to store, analyze and display image data provided by the spectrometer 450 and CCD 455. Approximately 60,000 points per motor rotation (at 0.5 Hz, or 30 rpm) may be digitized. to provide a circumferential sampling density of approximately 1.0 µm. The longitudinal velocity of the motor can be approximately 0.25 mm/s and the time required for one complete scan of the cylindrical sample may be about 100 seconds.

The $1/e^2$ diameter of the collimated beam on the grating-lens pair can be about 4.0 mm. As a result, the effective NA of this exemplary apparatus can be approximately 0.4, which corresponds to a theoretical spot diameter of approximately 1.2 µm and a confocal parameter of approximately 2.5 µm. In a system that is free of optical aberrations, a theoretical spectral resolution on the sample may be 0.8 Å, which can yield up to approximately 630 resolvable points across the spectrally encoded line 430. The spectrometer 450 in the detection arm can be designed to exceed the predicted spectral resolution of the probe.

Figure 5:
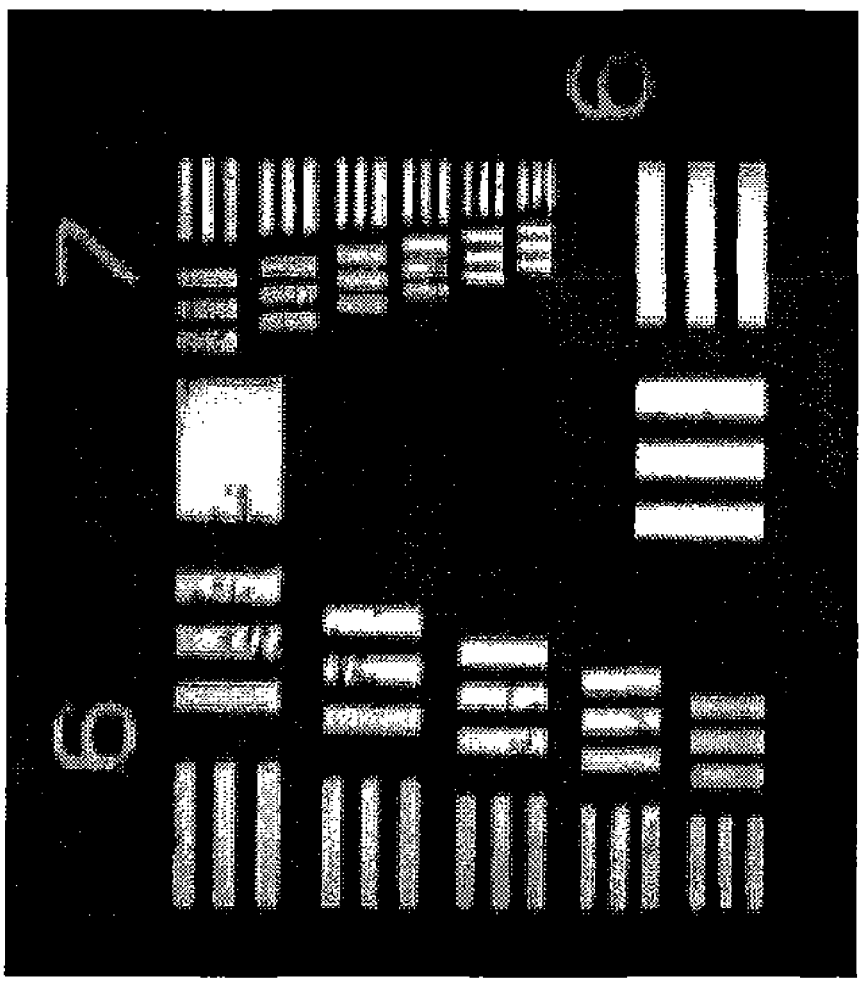
FIG. 5 is an exemplary SECM image of a USAF chart.

An SECM scan of a 1951 USAF resolution chart obtained using this apparatus is shown in FIG. 5. The smallest bars in this Figure, which are separated by 2.2 µm, were resolved. A transverse line spread function full-width-half-maximum ("FWHM") and an axial FWHM function obtained using a mirror scanned through the focus were measured as 2.1 µm and 5.5 µm, respectively. The field of view was observed to be about 500 µm. These measurements were slightly lower than corresponding theoretical values, which may be attributed to aberrations in the optical path. These parameters indicate that the exemplary apparatus described herein can be capable of providing sufficient resolution to be used for confocal microscopy in biological tissue.

Figure 6:
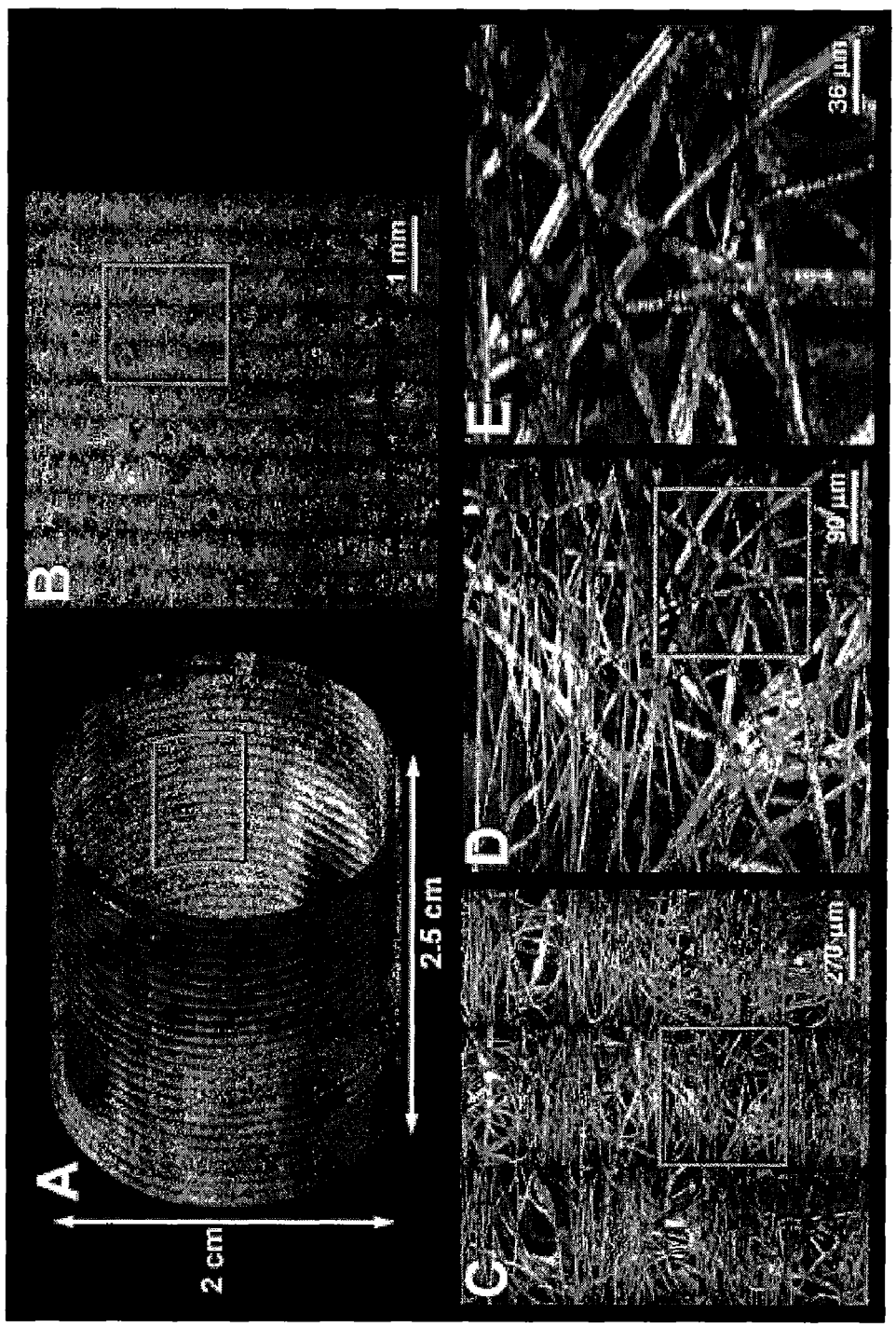
FIG. 6A is an exemplary SECM image based on data taken from a lens paper sample, displayed at a magnification of 1×.
FIG. 6B is an exemplary SECM image based on data taken from a lens paper sample, displayed at a magnification of 4.5×.
FIG. 6C is an exemplary SECM image based on data taken from a lens paper sample, displayed at a magnification of 16.7×.
FIG. 6D is an exemplary SECM image based on data taken from a lens paper sample, displayed at a magnification of 50×.
FIG. 6E is an exemplary SECM image based on data taken from a lens paper sample, displayed at a magnification of 125×.

Exemplary SECM image data for a complete pullback image of a 2.5 cm phantom specimen are shown in FIG. 6. Polar coordinates were converted to rectangular coordinates prior to generating these displayed images. The phantom specimen was made using lens paper affixed to the inner surface of a 2.1 cm inner diameter Teflon tube. In a low magnification image shown in FIG. 6A, macroscopic structure of the paper, including folds and voids, can be observed. Circumferential stripes that are visible may have resulted from the lower spectral power and lens aberrations that may be present at or near the ends of the spectrally-encoded line. Individual fibers and fiber microstructure can be clearly resolved in regions of this data set that are presented at higher magnifications, as shown in FIGS. 6B-6E.

Figure 7:
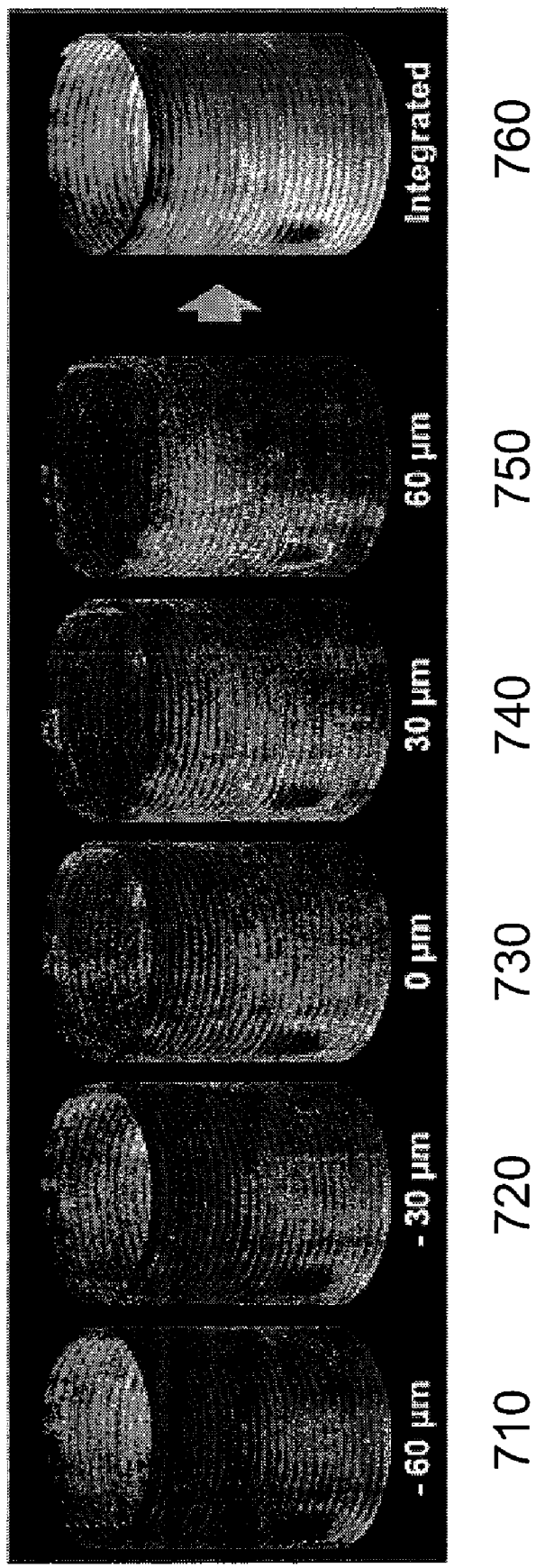
FIG. 7 is a series of exemplary SECM data obtained from a lens paper sample at five different focal positions, together with a combine image that was generated by combining the data in the five individual images.

By adjusting the focusing apparatus 415 in FIG. 4A, cylindrical two-dimensional ("2D") images of the phantom sample were acquired at five discrete focal depths over a range of 120 µm. These five images 710-750 shown in FIG. 7 were then summed to create an integrated image 760, which demonstrates a nearly complete coverage of the surface of the phantom sample.

Figure 8:
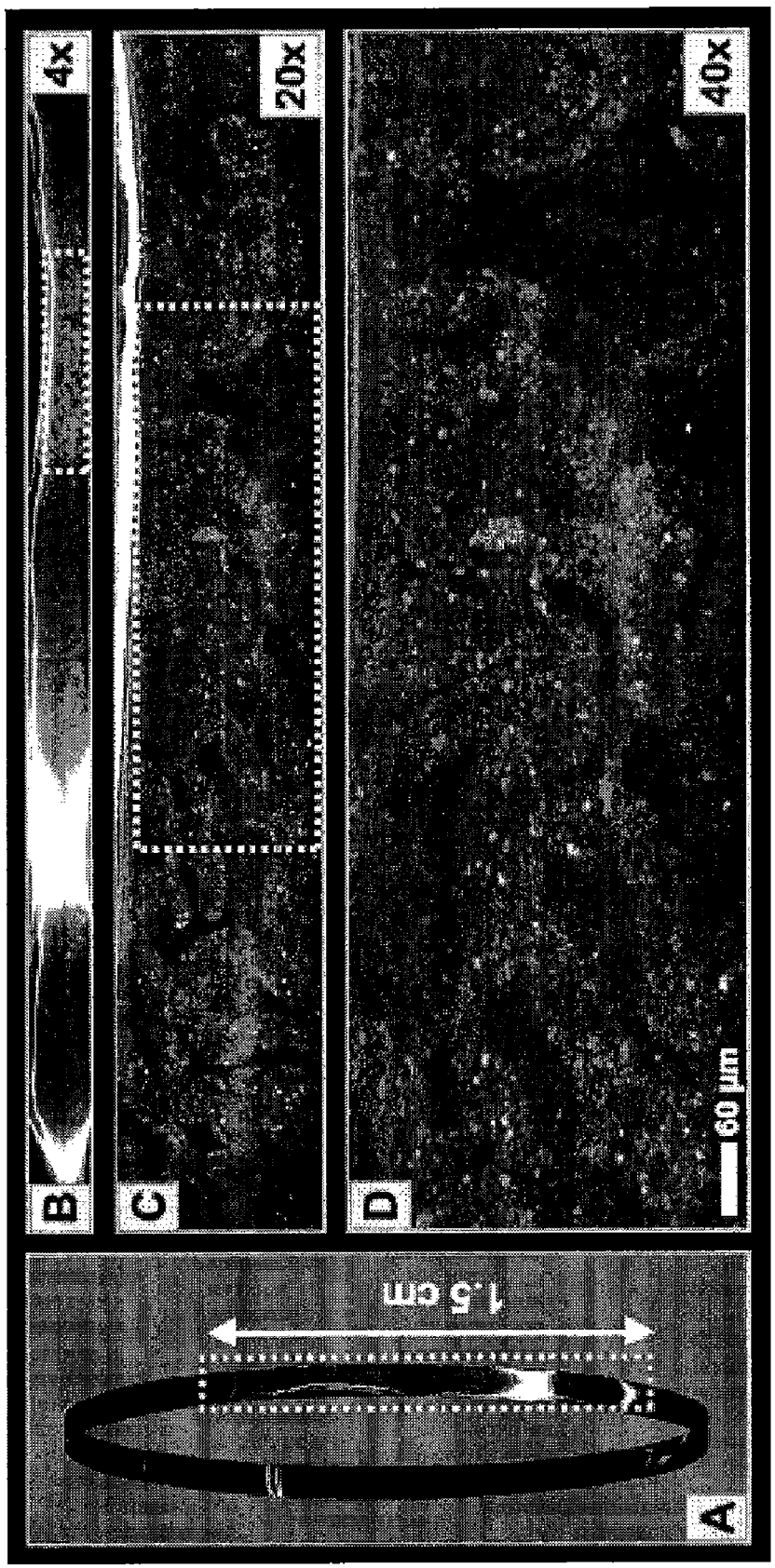
FIG. 8A is an exemplary SECM image based on data taken from a swine intestinal tissue fragment, displayed at a magnification of 1×.
FIG. 8B is an exemplary SECM image based on data taken from a swine intestinal tissue fragment, displayed at a magnification of 4×.
FIG. 8C is an exemplary SECM image based on data taken from a swine intestinal tissue fragment, displayed at a magnification of 20×.
FIG. 8D is an exemplary SECM image based on data taken from a swine intestinal tissue fragment, displayed at a magnification of 40×.

Imaging biological samples using an SECM apparatus such as that described herein can be complicated by the lack of a centering apparatus for the optical scan head. In order to provide further improvements for generating wide-field microscopy images and data, a sample of swine intestine was placed on top of a 2.0 cm diameter transparent cylinder. A 360° scan of this sample, which was acquired in 1 second, is shown in FIG. 8A. Imaged tissue likely appears in only one sector of the cylindrical scan because the probe was not centered and the sample did not wrap completely around the cylinder. FIGS. 8B-8D show a sequence of exemplary magnified regions of this tissue sample. The image shown in FIG. 8B is an expansion of a 1.5 cm sector outlined by a dotted rectangle in FIG. 8A. Similarly, the image in FIG. 8C represents an expansion of the rectangle outlined in FIG. 8B, and the image in FIG. 8D represents an expansion of the rectangle outlined in FIG. 8C. Magnified images of the tissue in the image FIG. 8B are suggestive of a glandular structure. The magnified images in FIGS. 8C-8D exhibit villi and nuclear features that are similar to those observed using a 1300 nm SECM system, as shown in FIGS. 2 and 3. Other areas of the SECM scan in FIG. 8A show artifacts, including specular reflectance from the transparent cylinder and complete signal dropout, both of which may result from improper positioning of a focused SECM beam.

Conducting comprehensive confocal microscopy in patients can present a variety of technical challenges. Such challenges may include, e.g., increasing the imaging rate, miniaturizing the probe optical components and mechanical components, incorporating a centering mechanism, and implementing a technique for dynamically changing the focal plane.

The image acquisition speed of an SECM system can be improved by, e.g., a factor of about 2-4 as compared with the exemplary system described hereinabove. Such an improvement can be realized by providing certain modifications. For example, a higher power semiconductor light source (such as, e.g., a Superlum Diode, T-840 HP: 25 mW, 840 nm, 100 nm spectral bandwidth) can provide, e.g., approximately 1000 spectrally resolvable points. Such an increase in optical power can improve sensitivity and a larger bandwidth may widen the field of view, making it possible to scan the SECM beam approximately two times faster. Also, using an optical circulator such as, e.g., an OC-3-850 (Optics for Research, Caldwell, N.J.) can increase the efficiency of light delivered to the probe and collected from the probe. Using a faster, more sensitive linear CCD such as, for example, an AVIIVA M4-2048 having 2048 pixels and a 60 kHz readout rate (Atmel Corporation,) can provide a twofold increase in data acquisition speed and an improved spectral response over the wavelength range used to generate image data. Performance may also be improved by using, e.g., a Camera Link interface that can be capable of transferring data at a rate of approximately 120 MB/s from a camera to a hard-drive array for storage.

Sensitivity, which can be understood to refer to a minimum detectable reflectance, is a system parameter that can affect confocal image quality and penetration depth. A fraction of the incident light, which may be approximately $10^{-4}$ to $10^{-7}$, can be reflected from skin at depths up to approximately 300 μm when using a near-infrared RCM technique. Based on the NA of the objective lens used in the exemplary system in accordance with certain exemplary embodiments of the present invention described herein, and the observation that skin may attenuate light more significantly than non-keratinized epithelial mucosa, the exemplary SECM probe objective described herein may collect approximately $3 \times 10^{-4}$ to $3 \times 10^{-7}$ of the illuminating light reflected from deep within tissue. A 25 mW light source may be separated into, e.g., approximately 1000 independent beams. A maximum double pass insertion loss can be estimated to be approximately 10 dB (which can include a 6 dB loss from the probe, and a 4 dB loss from the fiber optics and spectrometer). Each pixel in an array may thus be illuminated by approximately 50 to 50,000 photons/pixel for each line integration period based on these estimated parameters.

Using a multi-mode detection technique, a factor of 10 signal gain may be achieved, resulting in approximately 500 to 500,000 photons/pixel per scan for such a configuration. A single pixel on an Atmel AVIIVA M4 camera, e.g., can reliably detect light if a signal is above the dark current fluctuation that occurs at approximately 240 photons. If this device has approximately a 50% quantum efficiency at these wavelengths, a minimum detectable signal can be produced at approximately 480 photons/pixel per scan. Based on these approximations, an Atmel camera may have sufficient sensitivity to allow SECM imaging at deeper tissue depths. Quantum noise-limited detection of a predicted minimum reflectance can be achieved by using a multi-mode fiber for collection or by increasing the source power.

Figure 9:
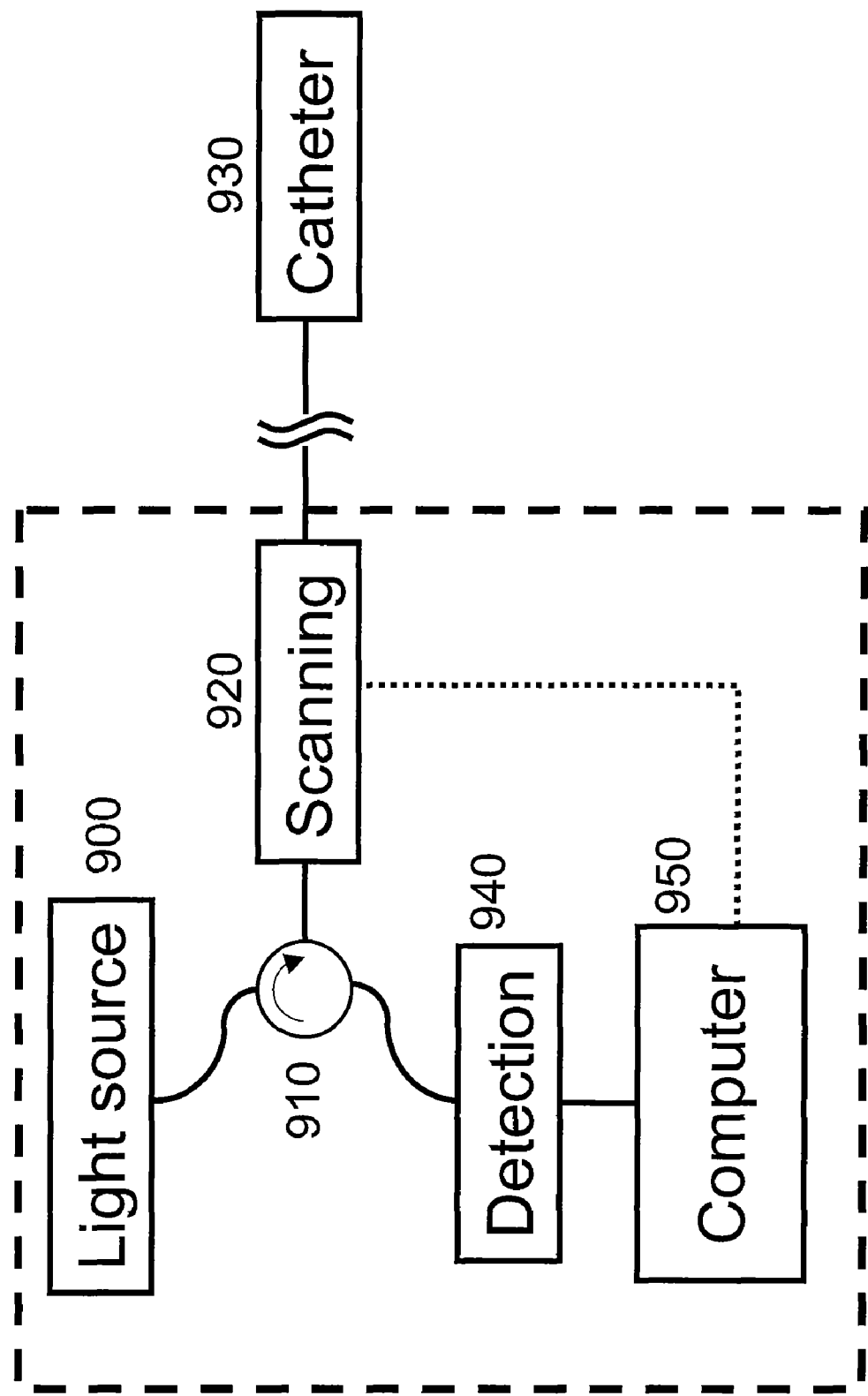
FIG. 9 is a schematic illustration of an exemplary SECM system capable of imaging large tissue volumes.

A schematic diagram of an apparatus capable of performing large-area microscopic imaging of epithelial organs in accordance with certain exemplary embodiments of the present invention is shown in FIG. 9. A light source 900, which may be a broadband source or a wavelength swept source, can provide light which may be conveyed through a circulator 910 or, alternatively, through a fiber splitter. The light can then be transmitted to an imaging catheter 930 through a scanning mechanism 920. Scanning can be performed either externally to the catheter or within the catheter. In certain preferred exemplary embodiments, pullback scanning may be performed outside the catheter, and rotational scanning may be performed inside the catheter. Reflected light that is collected may then be detected with a detector 940 which may be, e.g., a spectrometer if a broadband light is used. The detector 940 may also be, e.g., a single detector if a wavelength swept source is used. Data provided by the detector 940 may be processed, displayed and/or saved by a computer 950 which may also be configured to control and synchronize the scanning procedure.

Screening large luminal organs may preferably utilize a centering of a distal portion of a catheter within the lumen to provide a consistent focus distance and/or depth relative to the tissue, and rapid acquisition of circumferential images over lengths of several centimeters. These criteria can be satisfied by incorporating a circumferentially scanning imaging probe within a centering device. Provided an imaging optical arrangement located at or near the middle of the centering device can provide several additional advantages, including, e.g., elimination of surface height fluctuations, which may simplify focusing requirements, and physical coupling of the imaging system to a patient, which can greatly reduce motion artifacts that may otherwise occur.

Figure 10:
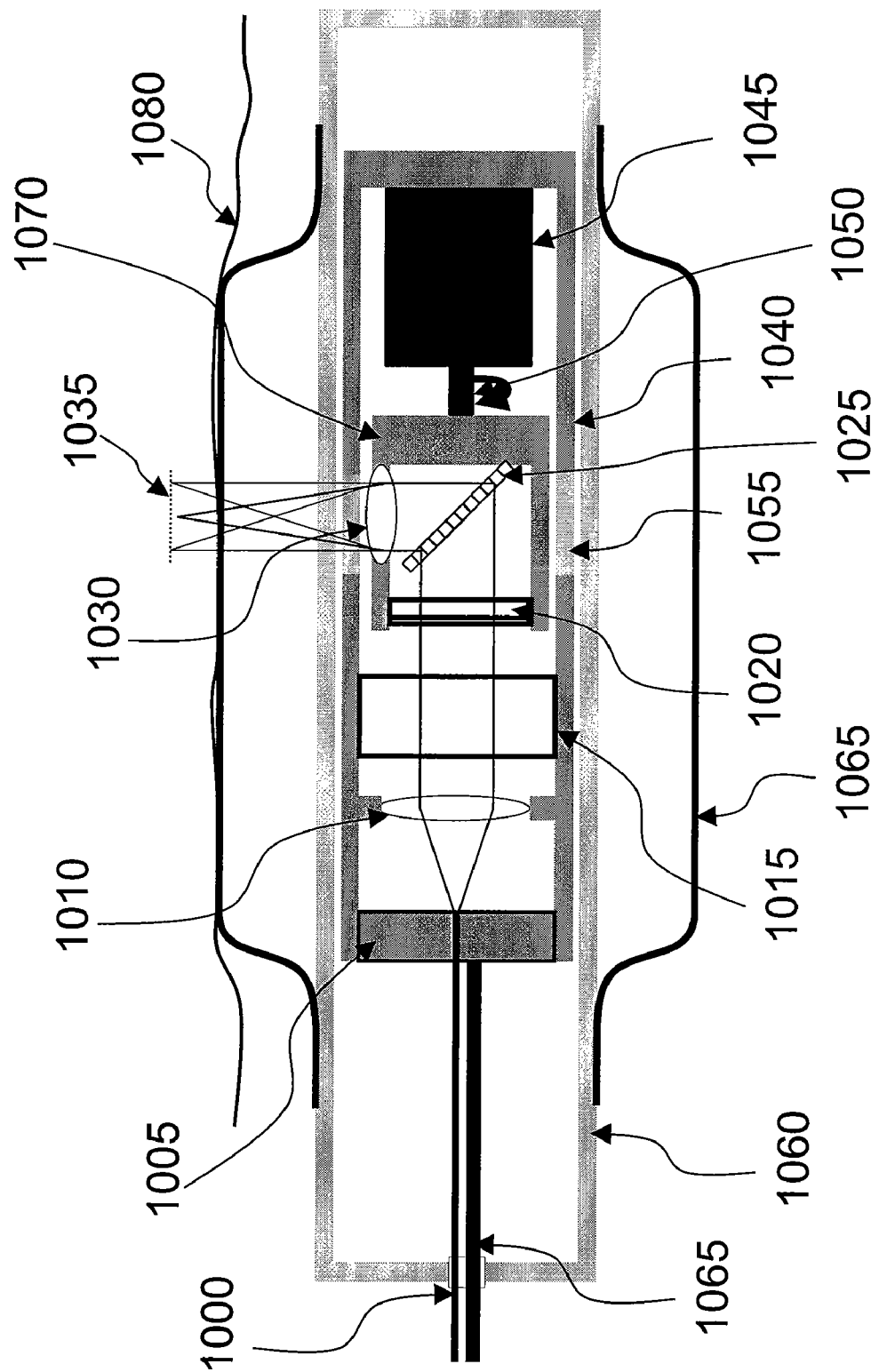
FIG. 10 is a schematic illustration of a distal end of an exemplary catheter that may be used for imaging in accordance with exemplary embodiments of the present invention.

A schematic diagram of the distal end of an SECM catheter in accordance with certain exemplary embodiments of the present invention is shown in FIG. 10. Light can be provided through an optical fiber 1000, which may be fixed by a fiber chuck 1005, and then collimated using a collimating lens 1010. This light may then pass through a variable focusing mechanism 1015 and a cylindrical lens 1020 that can be configured to pre-compensate the optical path to correct for astigmatism effects. The light may then be diffracted through a diffraction grating 1025, which can be configured to diffract a center wavelength of the light by, for example, approximately 90 degrees, and focused by an imaging lens 1030 onto a spectral encoded line 1035.

Speckle artifact may be reduced using multi-mode detection by increasing the diameter of a pinhole aperture associated with the optical fiber 1000. This technique can provide an increased signal throughput and a reduction in speckle artifacts, together with only a slight decrease in spatial resolution. A double clad optical fiber may be used to implement this technique for spectral encoding, in which a single-mode core can illuminate a tissue and a multi-mode inner cladding can detect reflected light.

The imaging lens 1030 may preferably have a relatively large working distance that can be, e.g., approximately 2-7 mm, and maintain a large NA of approximately 0.25 to 0.5. In addition, the imaging lens 1030 can be thin, preferably not more than about 5 mm thick. Conventional lenses, such as aspheres or achromats, may be used as imaging lenses.

The inner housing 1040 may surround some or all of the various optical components and the motor 1045, and it may allow for longitudinal positioning of these components within the outer housing 1060. The inner housing 1040 can include portions thereof that have good optical transmission characteristics and low wavefront distortion to allow high quality imaging, while still maintaining structural rigidity to maintain a motor shaft 1050 centered within the probe. Materials that may be used to form transparent windows as part or all of the inner housing 1040 may include, for example, glass or plastic materials such as, e.g., Pebax and high-density polyethylene (HDPE).

The outer housing 1060 can surround the inner housing 1040, and can be configured to remain in a fixed position relative to the imaged tissue 1080 using the centering mechanism 1065. An opening in a wall of the outer housing 1060 can allow a pullback cable 1065 to move the inner housing 1040. Linear scanning can be conducted by affixing the inner housing 1040 to a computer-controlled translator (such as a translator that may be provided, e.g., by Newport Corp., Irvine, Calif.), while maintaining the outer housing 1060 in a fixed position relative to the tissue 1080 being imaged. Such a pullback technique may be used, e.g., to obtain longitudinal esophageal OCT images. All or a portion of the outer housing 1060 may be transparent to allow a transmission of light therethrough. Optical characteristics of the transparent portions of the outer housing 1060 can be similar to those of the inner optical window 1055.

The cylindrical lens 1020, the diffraction grating 1025, and the imaging lens 1030 may be housed in a rotational housing 1070, which may be attached to the motor shaft 1050. A conventional motor 1045 may be used, which can have a diameter as small as about 1.5 mm or less. Using an encoder may improve image quality and registration, and may also increase the diameter of the motor 1045 to approximately 6-10 mm. Such a motor can be provided, e.g., by (MicroMo Electronics, Inc. (Clearwater, Fla.). Dimensions of motor wires can be minimized to limit obstruction of a field of view of the apparatus. Circumferential scanning may be performed by rotating the rotational housing 1070 within the inner housing 1040 using the motor 1045 via the motor shaft 1050.

Figure 11:
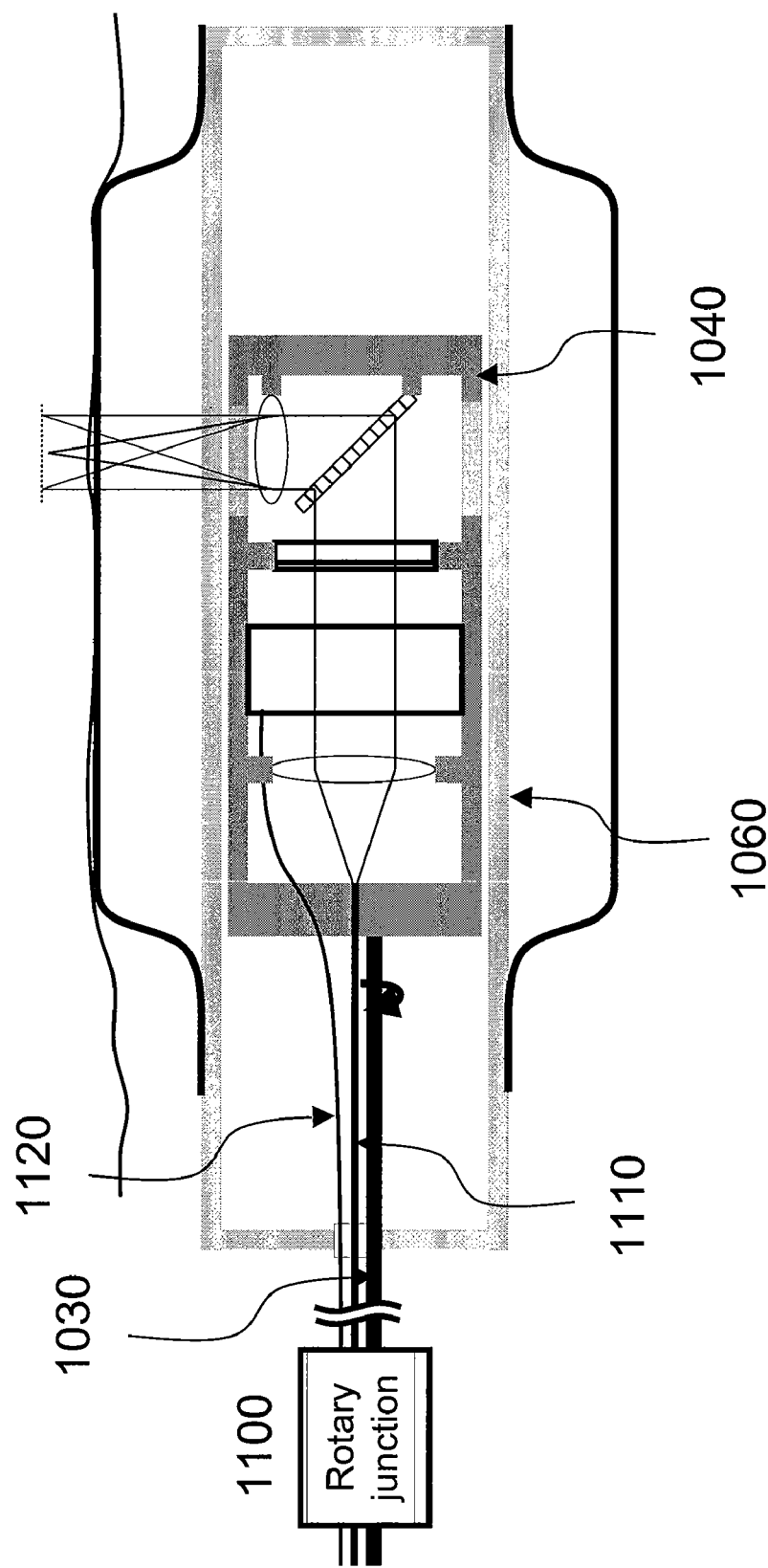
FIG. 11 is a schematic illustration of an exemplary catheter that may be used for imaging in accordance with exemplary embodiments of the present invention that includes an external rotational scanning arrangement.

A catheter configured to provide rotation of the inner housing 1040 relative to the external housing 1060 from a location external to a distal end of the catheter, in accordance with certain exemplary embodiments of the present invention, is illustrated schematically in FIG. 11. A rotary motion can be transmitted through an optical rotary junction 1100, and light may be coupled into a rotation optical fiber 1110. The rotary junction may also maintain electrical contact via one or more electrical wires 1120 and mechanical contacts via a rotatable pullback cable 1030 that can be configured to control pullback and focusing mechanisms. In the exemplary apparatus configuration shown in FIG. 11, the inner housing 1140 does not surround a motor and thus it can be smaller and lighter.

Figure 12B:
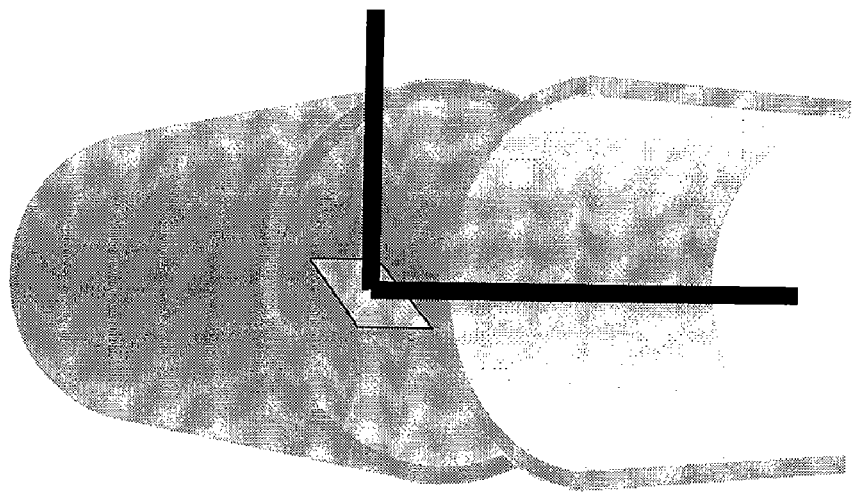
FIG. 12B is a schematic illustration of an astigmatic aberration correction using a curved window.
Figure 12A:
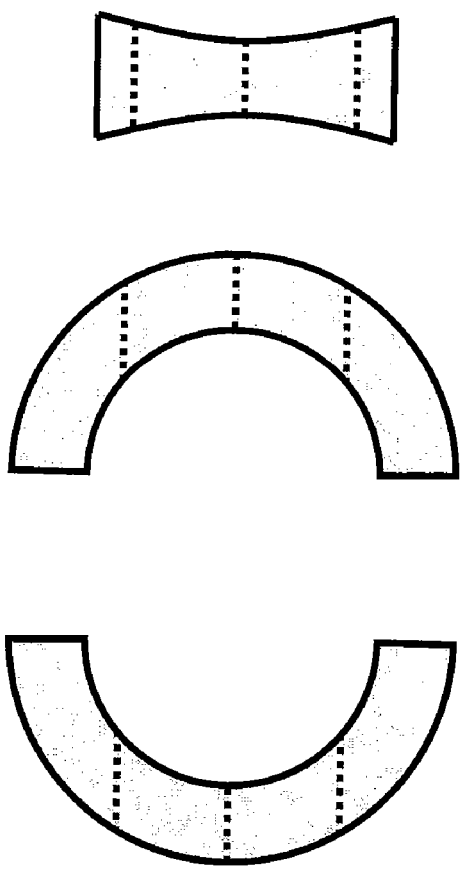
FIG. 12A is a schematic illustration of optical effects of a curved window and a negative cylindrical lens.

A cylindrical lens may be used to correct for astigmatism effects that can be created by a wall of a balloon or another centering device and/or by a transparent window or a transparent section of the inner and/or outer housing. A curved glass can induce astigmatism in a manner similar to that of a negative cylindrical lens. For example, the astigmatism induced by the two curved transparent walls shown in FIG. 12A are optically similar to the negative cylindrical lens shown towards the right side of this Figure. Light passing through the central dashed line of any of the objects shown in FIG. 12A may have a shorter path than light passing through the upper or lower dashed lines, which leads to induced astigmatism. Efficient and accurate correction of this optical distortion can be achieved, e.g., by placing a curved window, similar to the window that induces the astigmatism, in the optical path, as shown in FIG. 12B. The curvature axis of the correcting curved window should be perpendicular to the axis of the curved housing windows to provide optical correction of the astigmatism.

In another exemplary embodiment of the present invention, an endoscopic SECM system can be provided that is capable of comprehensively imaging an organ without user intervention during the acquisition of image data. The system can be capable of accounting for motion due to, e.g., heartbeat, respiration, and/or peristalsis movements. Utilization of a centering mechanism can greatly reduces artifacts caused by motion of the tissue being imaged. For example, variations in distance between an imaging arrangement and the tissue being imaged can vary, for example, by as much as approximately ±250 μm during one comprehensive scan. This distance variation can occur on a slow time scale (e.g., over several seconds) relative to a circumferential scanning speed, but it may be significant relative to a time required to scan the length of a tissue region being imaged during longitudinal pullback of the imaging arrangement.

An exemplary technique can be used in accordance with certain exemplary embodiments of the present invention to reduce or eliminate the effects of tissue motion during sampling. This technique, illustrated in FIG. 13A, can include a procedure for obtaining image data over a wider range of focal depths. If a desired total imaging depth is, for example, 200 μm, and a variation in tissue distance from the imaging arrangement is, e.g., 1250 μm, then image data can be acquired over a focal range of about 700 μm. This procedure can ensure that image data is obtained throughout the desired tissue volume. Although many portions of the volumetric image may not contain tissue when imaged, it is likely that at least one good image would be obtained from most regions of the tissue volume of interest.

A second exemplary technique that may be used to compensate for motion of tissue during imaging is illustrated in FIG. 13B. This technique can include a procedure for determining a distance between the imaging lens and a surface of the tissue being imaged. This distance can be tracked, and a focus of the lens can be adaptively controlled to provide a known focal distance relative to the tissue surface throughout the acquisition of image data in the tissue volume of interest. Adaptive focusing can decrease the number of focal scans required, and therefore may also decrease the time needed to obtain comprehensive coverage of the tissue volume of interest. Focus of the beam can be controlled, e.g., using an interferometric signal, a time-of-flight signal, an intensity of the electromagnetic radiation, etc.

Figure 14:
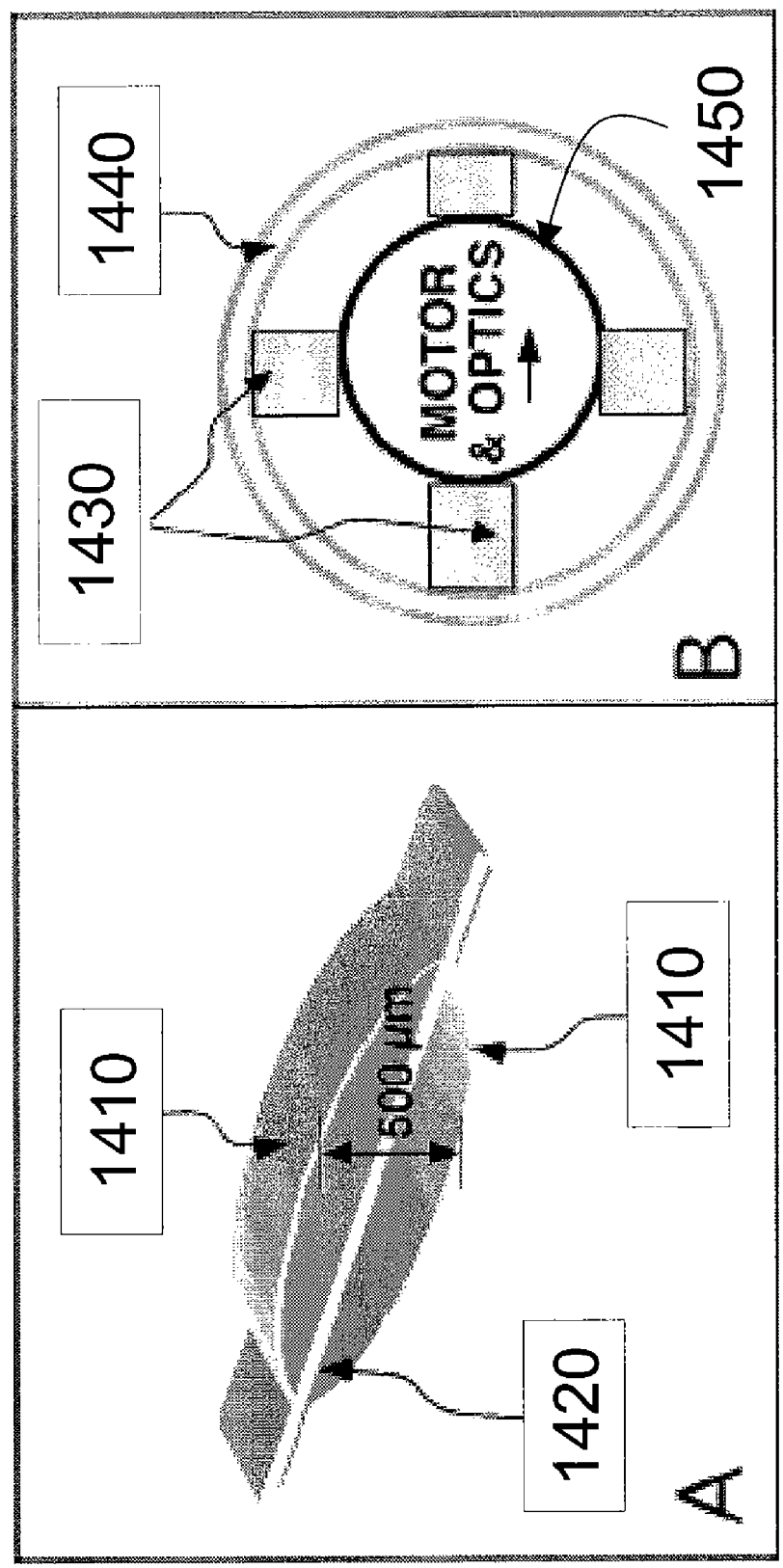
FIG. 14A is a schematic illustration of a dual bimorph piezoelectric bender.
FIG. 14B is a schematic illustration of an exemplary arrangement whereby a motor may be moved within a transparent outer sheath using bending actuators.

The above-described exemplary techniques for addressing motion of the tissue being imaged can utilize a mechanism for adjusting the focal distance of the imaging arrangement. There are several exemplary techniques that may be used for adjusting the focal depth within the tissue volume being imaged. For example, an inner housing of the imaging arrangement that includes a focus lens can be moved relative to an exterior housing. To achieve this motion, for example, multi-layered bimorph piezoelectric actuators 1410 (e.g., D220-A4-103YB, Piezo Systems, Inc., Cambridge, Mass.) shown in FIG. 14A can be attached to, e.g., a metal sheet 1420 at both ends, which may provide a buckling of the ceramic material. These actuators can be placed back-to-back, as shown in FIG. 14A, which can effectively double the range of their free motion. Four such actuators 1430 can be arranged between an outer sheath 1440 and an assembly 1450 that can include a motor and focal optical components surround the motor, as shown in FIG. 14B. These actuators 1430 can be utilized to change the focal position over the required range by controllably displacing the assembly 1450 relative to the outer housing 1440. This technique can require the presence of a high voltage within the probe, additional electrical wires that may traverse and interrupt the field of view, and/or an increase of the overall diameter of a probe containing the imaging arrangement by, e.g., several mm.

Figure 15:
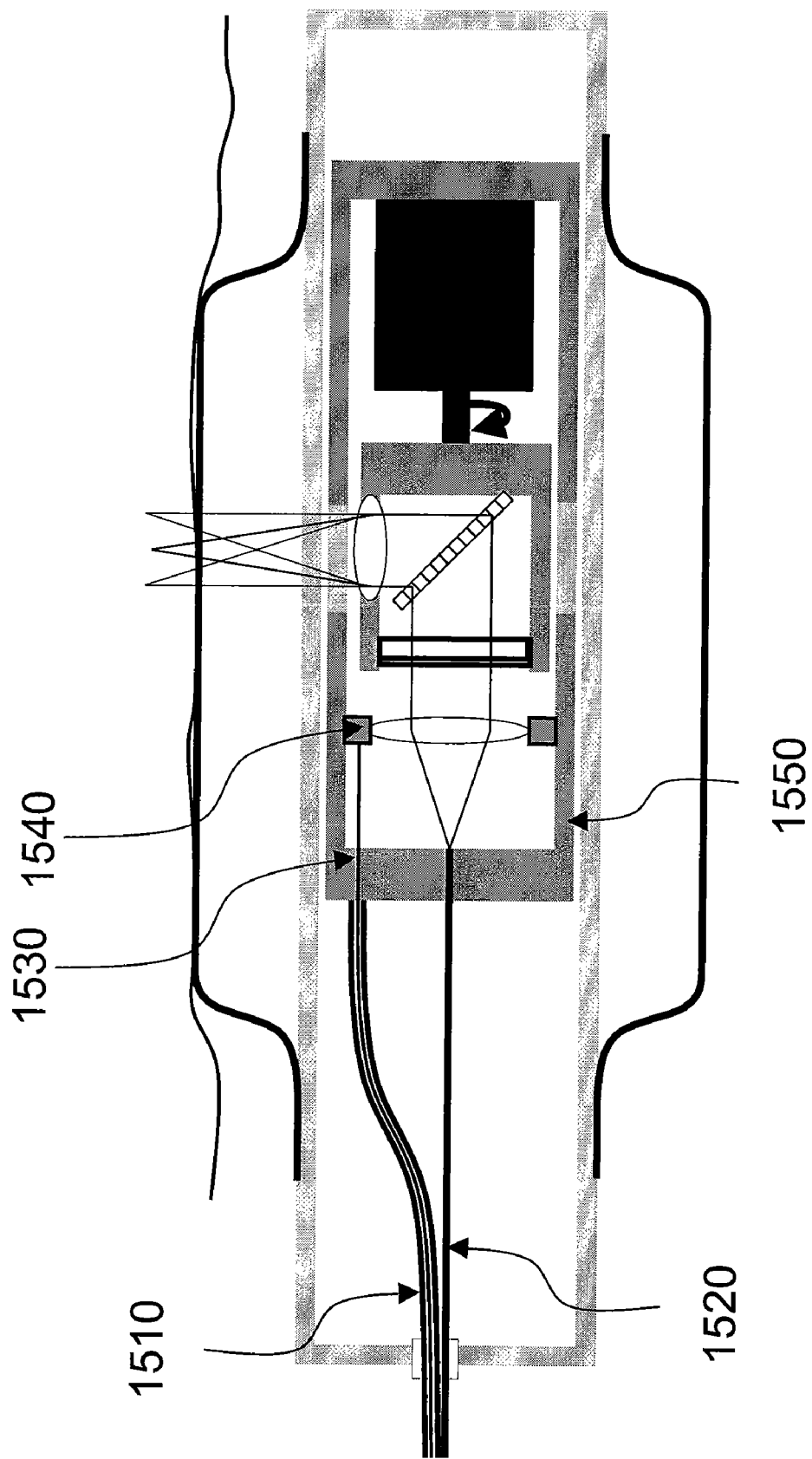
FIG. 15 is a schematic illustration of an exemplary balloon catheter design that is configured to control a focus by translating a collimating lens.

An alternate exemplary technique that may be used to adjust the focal distance of the imaging arrangement is shown in FIG. 15. A cable housing 1510 can be provided that surrounds a cable 1530. The cable 1530 can be attached at one end to a collimating lens 1540, which may be configured to be movable in a longitudinal direction relative to a housing 1550. The collimating lens 1540 can be moved relative to the housing 1550 and other optical components to vary the focal distance. This translation can be controlled, e.g., externally to the imaging catheter, using the cable 1530 as is illustrated in FIG. 15. Alternatively, motion of the collimating lens 1540 can be controlled, e.g., by an electric or piezoelectric motor that can be provided inside the catheter. The focal distance can also be varied by moving an optical fiber 1520, which can provide the light used to image tissue, relative to the collimating lens 1540. Alternatively, both the optical fiber 1520 and the collimating lens 1540 may be moved relative to each other to vary the focal distance.

The focal length can be shifted by a distance $\Delta z$ by changing the separation between the optical fiber 1520 and the collimating lens 1540 by a distance of approximately $M^2 \Delta z$, where M is a magnification factor of the imaging apparatus. For example, an exemplary imaging apparatus can have a magnification factor that is approximately 3. To obtain a change in the focal distance of approximately ±450 μm, the distance between the optical fiber 1520 and the collimating lens 1540 would need to move approximately ±4.0 mm, which is a distance that can be achieved using any of the techniques described above for changing the focal distance.

Figure 16:
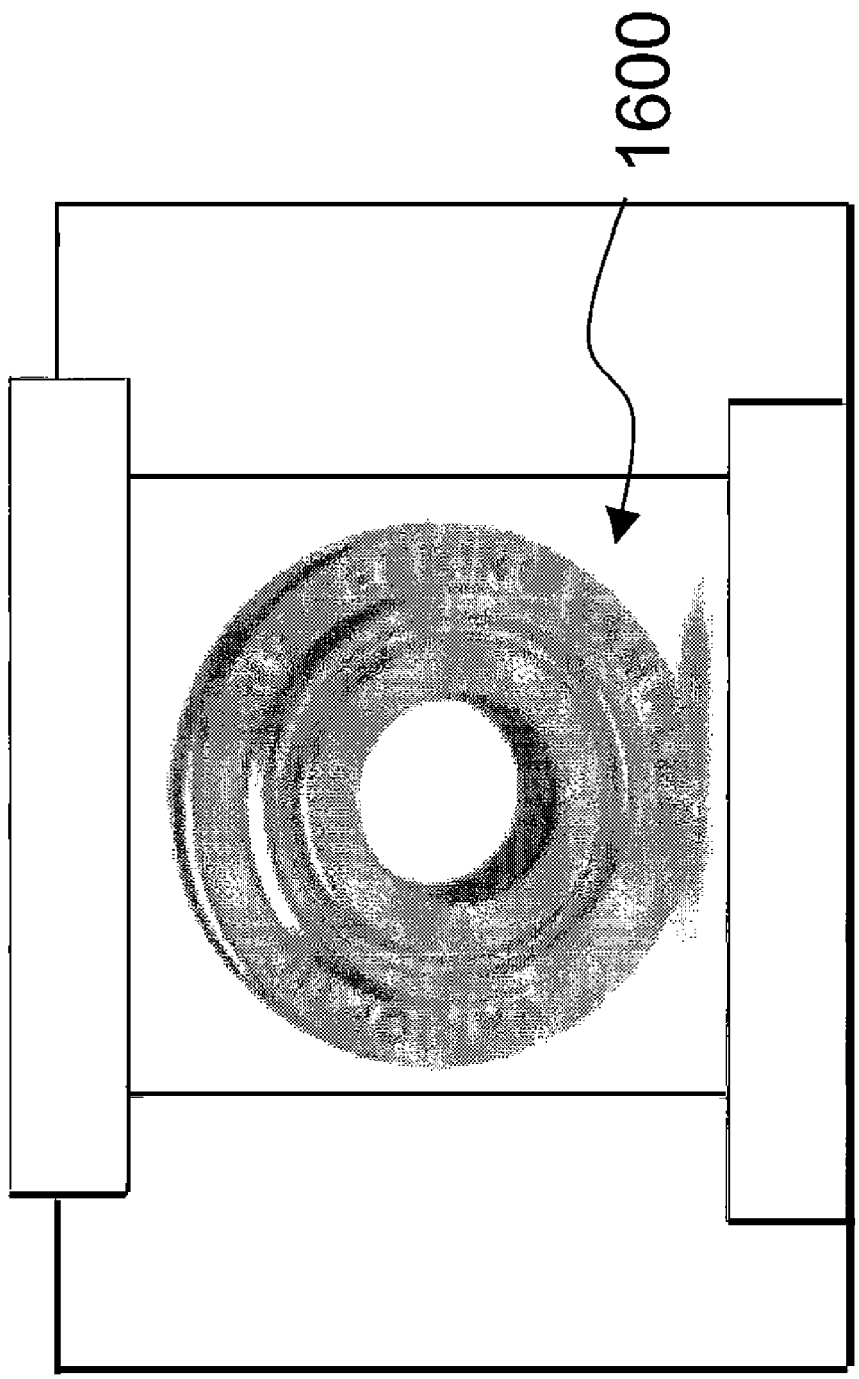
FIG. 16 is a photograph of a particular variable-focus lens.

A further exemplary technique that can be used to vary the focal distance can be to utilize an electronically tunable variable lens. For example, a commercially available lens 1600 (Varioptic AMS-1000, Lyon, France) shown in FIG. 16, which may be used in cell phone cameras, may be utilized to vary the focal length in an imaging apparatus in accordance with an exemplary embodiment of the present invention. This lens 1600 uses an electrowetting principle, and can provide a variable focal length between about −200 mm and 40 mm, with optical quality that may only be limited by diffraction effects. The current effective clear aperture (CA) of this exemplary lens 1600 is 3.0 mm and the total outer diameter (OD) is 10 mm. A similar lens having a 4.0 mm CA and a 6.0 mm OD may be possible to produce. The full-range response time of this exemplary lens 1600 is about 150 ms, which can be sufficiently fast to be used to track the distance between the optical components and the tissue surface and adjust the focal distance accordingly. It may be possible to produce this type of lens having a response time of about 10 ms. Utilizing a variable lens such as the one described above between the collimator and the SECM grating can provide, e.g., a focal distance that can vary by about ±300 μm or greater.

Figure 17:
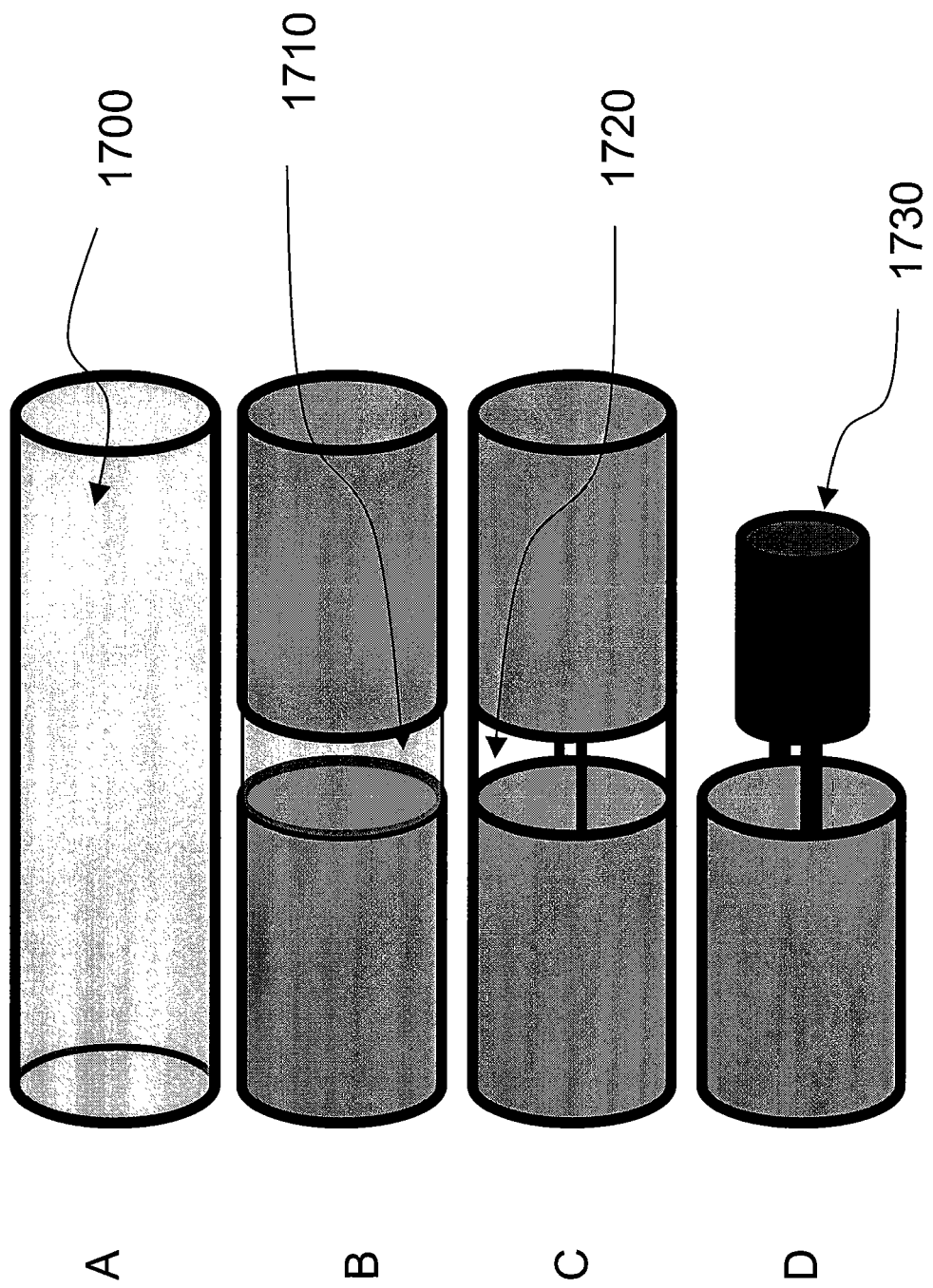
FIG. 17A is a schematic illustration of a cylindrical inner housing design which has a form of a transparent cylinder.
FIG. 17B is a schematic illustration of a cylindrical inner housing design which includes a transparent window.
FIG. 17C is a schematic illustration of a cylindrical inner housing design which includes several openings in the housing wall.
FIG. 17D is a schematic illustration of a cylindrical inner housing design which includes openings in a connection between the housing and a motor.

Various configurations can be provided for the inner housing in accordance with certain exemplary embodiments of the present invention. For example, a housing formed from transparent material 1700 can be used, as shown in FIG. 17A. Alternatively, a housing can be provided that includes a transparent window 1710, as shown in FIG. 17B. A housing may also be provided that includes an opening 1720 between two walls, such as that as shown in FIG. 17C, or an opening adjacent to a motor 1730 that may be attached to the housing as shown, e.g., in FIG. 17D.

Figure 18:
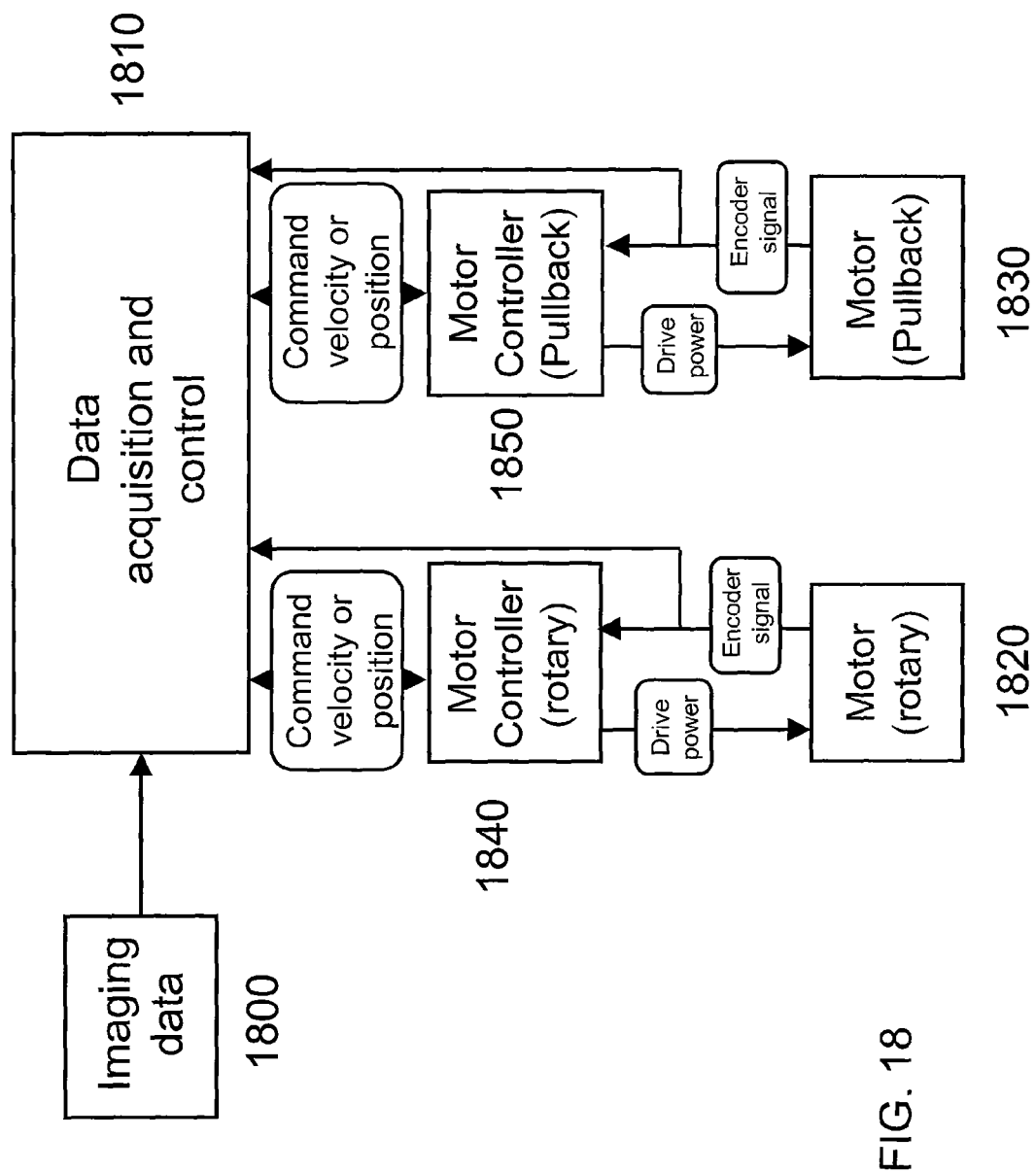
FIG. 18 is a schematic illustration of electrical and data connections between components of an exemplary imaging system.

An exemplary schematic diagram of a control and data recording arrangement which can be used with the exemplary system shown in FIG. 9 is provided in FIG. 18. The arrangement shown in FIG. 18 can be configured to record a beam position while acquiring imaging data 1800, which can provide a more precise spatial registration of the imaging data 1800. As shown in FIG. 18, the imaging data 1800 can be acquired by a data acquisition and control unit 1810. A catheter scanner arrangement may scan a beam, e.g., using a rotary motor 1820 to provide angular motion of the beam and a pullback motor 1830 to move the beam longitudinally. The rotary motor 1820 can be controlled by a rotary motor controller 1840, and the pullback motor 1830 can be controlled by a pullback motor controller 1850. Each of these control techniques may be performed using a closed loop operation. The data acquisition and control unit 1810 can direct the motor controller units 1840, 1850 to provide specified motor velocities and/or positions. Encoder signals generated by the motors 1820, 1830 can be provided to both the motor controller units 1840, 1850 and the data acquisition and control unit 1810. In this manner, the encoder signals associated with each motor 1820, 1830 can be recorded when a line of imaging data 1800 is acquired, thereby allowing a precise beam position to be associated with each line of data 1800.

Figure 19:
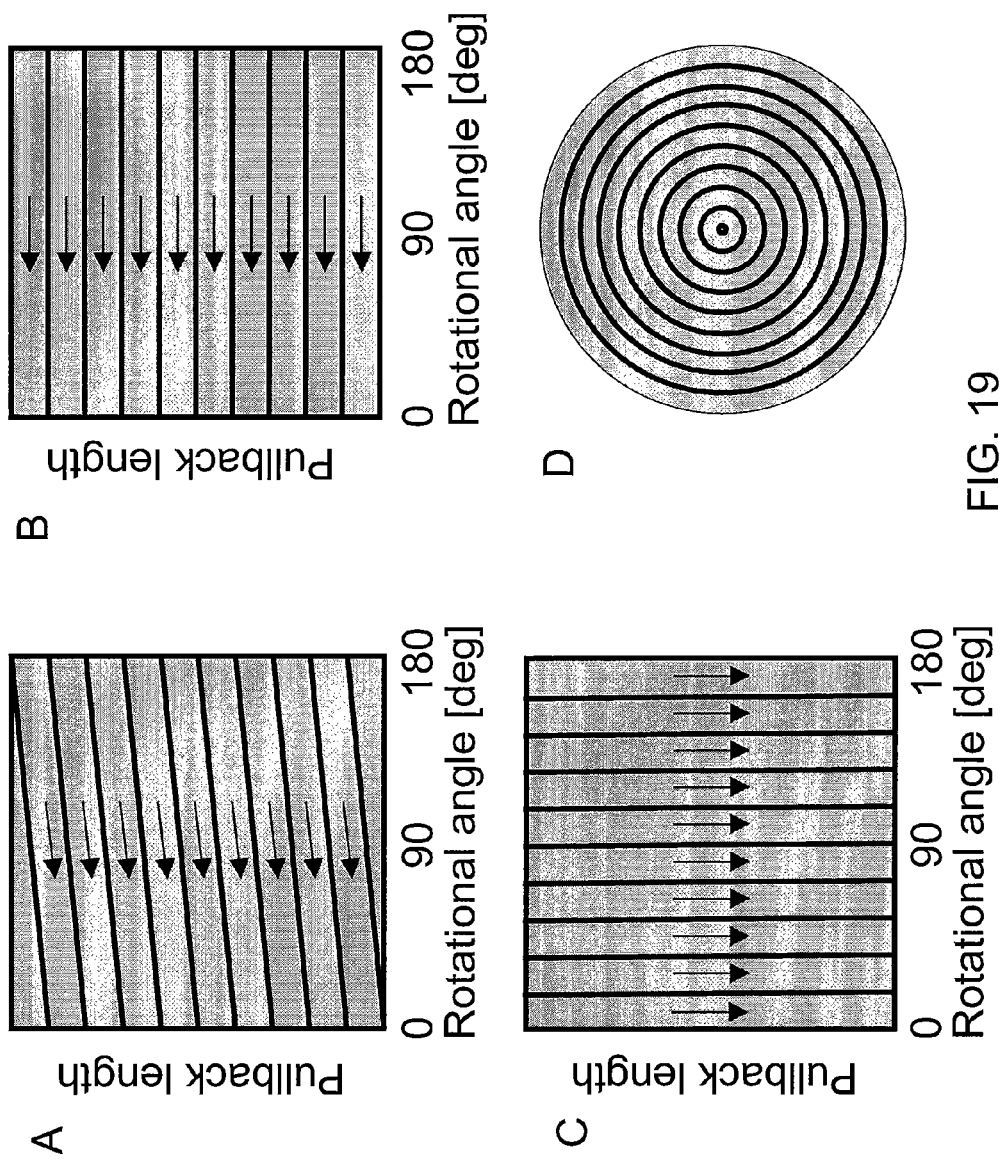
FIG. 19A is an illustration of an exemplary probe scanning pattern in which a beam is rotated quickly and simultaneously displaced slowly in an axial direction to provide a spiral imaging pattern.
FIG. 19B is an illustration of an exemplary probe scanning pattern in which the beam is rotated quickly and then repositioned axially.
FIG. 19C is an illustration of an exemplary probe scanning pattern in which the beam is rapidly scanned in the axial direction and then repositioned in the rotational direction.
FIG. 19D is an illustration of an exemplary probe scanning pattern in which the beam is scanned over concentric circular paths cover a circular tissue area.

Various scanning priorities that may be used in the imaging catheter in accordance with an exemplary embodiment of the present invention are shown in FIG. 19. For example, an exemplary scanning technique in which rotational scanning is performed as a first priority and axial (pullback) scanning is performed as a second priority is shown in FIG. 19A. This technique can provide a set of data having a helical geometry.

In a further scanning technique, the axial scanning can be performed in small increments, with each axial increment following a full revolution, as shown in FIG. 19B. Alternatively, axial (pullback) scanning can be performed as a first priority and rotational scanning can be performed as a second priority, which may generate the scanning pattern shown in FIG. 19C. A greater imaging quality can be achieved along a direction of the first scan priority. Thus, a choice of scan priority may depend on whether transverse (rotational) images or axial images are preferred. Imaging of other organs or tissues that may have different symmetries can be performed in several ways. For example, a circular scanning pattern that may be used to image certain organs is shown in FIG. 19D.

Figure 20:
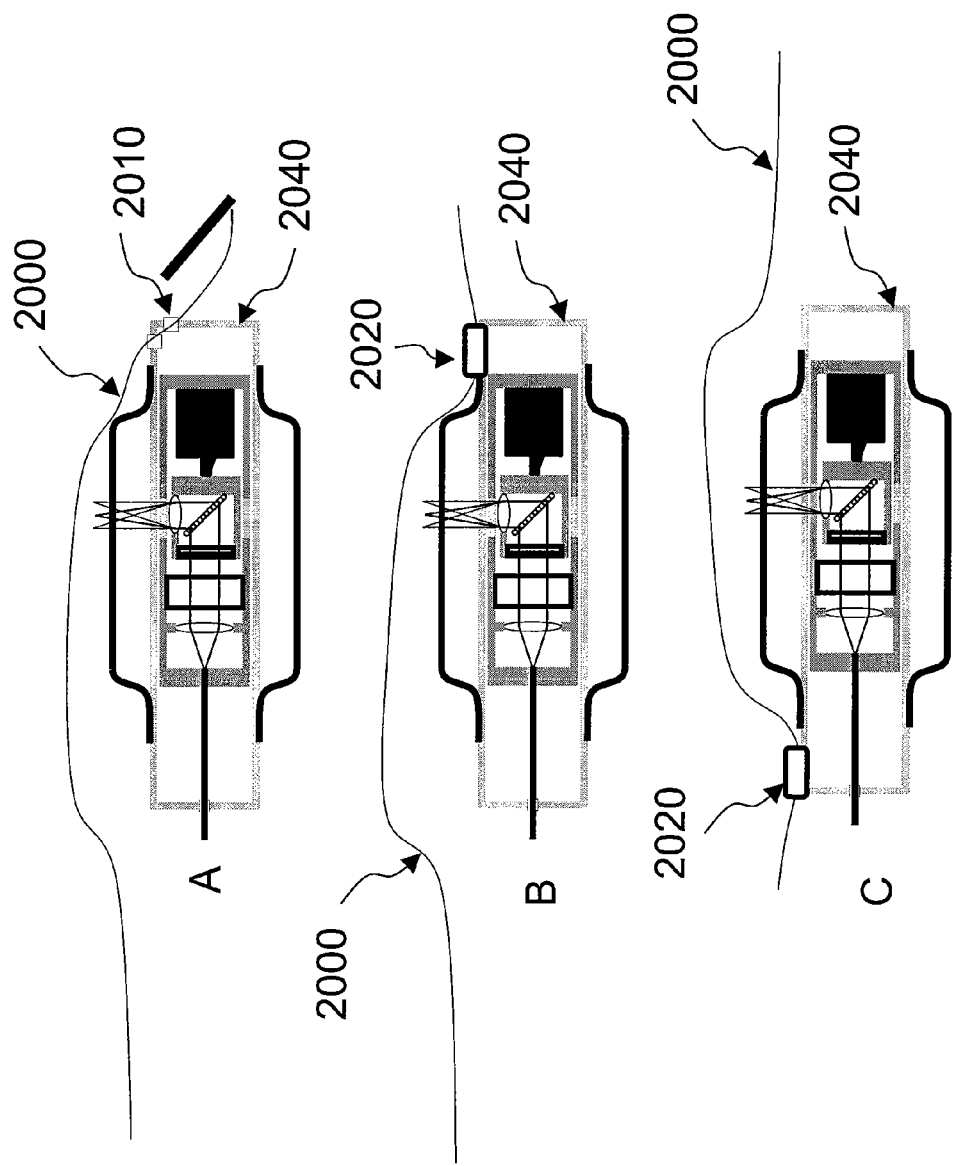
FIG. 20A is a schematic illustration of a rapid exchange balloon catheter design which includes a guidewire arrangement located at a distal tip of a housing.
FIG. 20B is a schematic illustration of a rapid exchange balloon catheter design which includes the guidewire arrangement located at the distal tip of the housing and having a form of a secondary channel.
FIG. 20C is a schematic illustration of a rapid exchange balloon catheter design which includes the guidewire arrangement located at a proximal tip of a housing and having a form of a secondary channel.

In a further exemplary embodiment of the present invention, a balloon catheter such as, e.g., the one shown in FIG. 10, can be configured to allow for a rapid-exchange placement procedure using a guidewire. In a rapid-exchange placement procedure, a guidewire can first be placed in an organ to be imaged, and the catheter can then be threaded down the guidewire. This procedure can allow easier and more precise placement of the catheter in many applications. Various configurations may be used to guide a catheter using a rapid-exchange procedure. For example, FIG. 20A shows an exemplary guidewire 2000 that passes through a hole 2010 in a distal end of the outer housing 2040. In a second exemplary configuration shown in FIG. 20B, a guidewire 2000 passes through a tube 2020 that is attached to the distal end of the outer housing 2040. Alternatively, the guidewire 2000 can be configured to pass through the tube 2020 which may be attached to a proximal end of the outer housing 2040, as shown in FIG. 20C.

Figure 21:
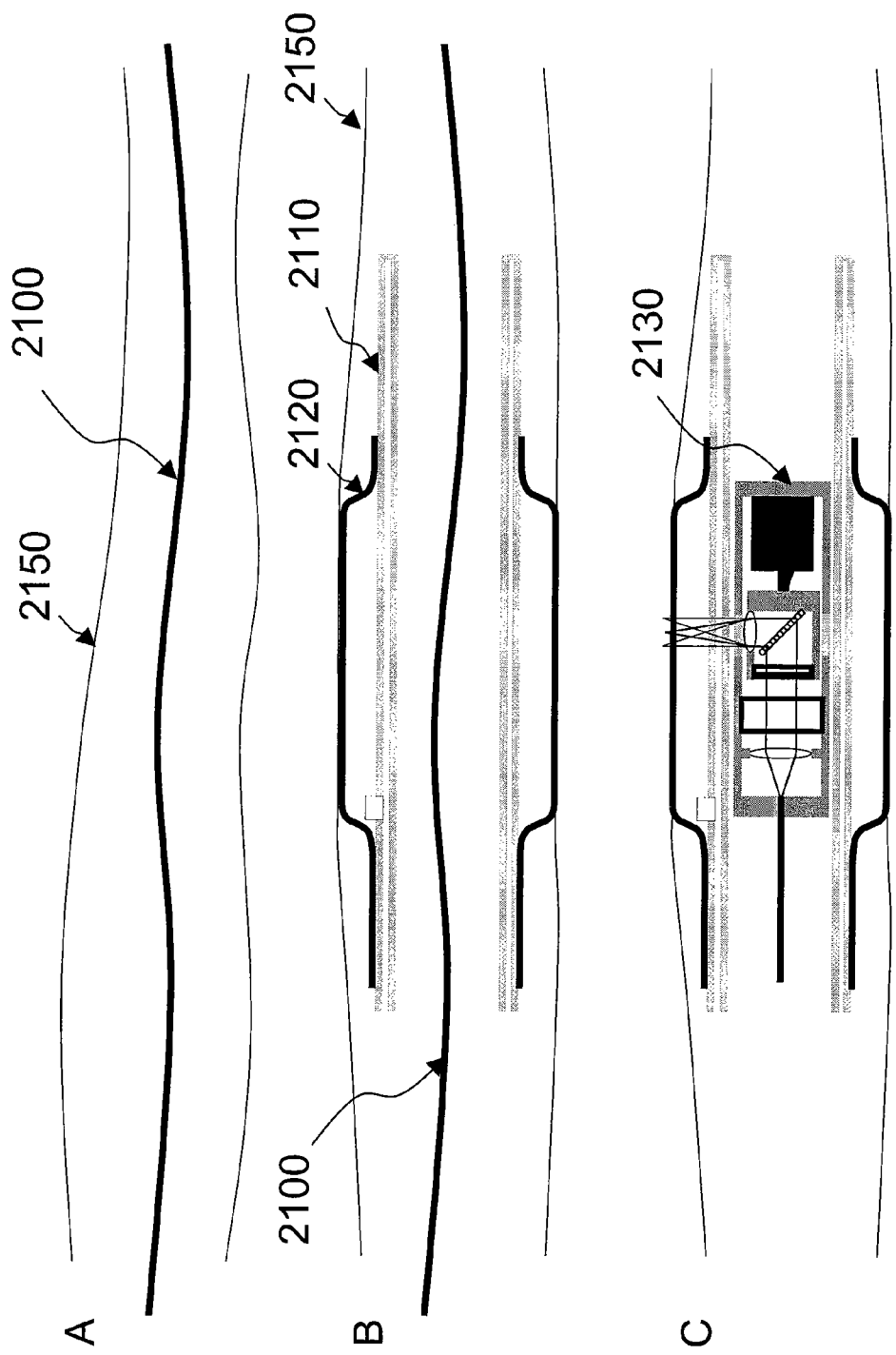
FIG. 21A is a schematic illustration of a first step in an exemplary technique for positioning a wire balloon catheter that includes insertion of a guidewire.
FIG. 21B is a schematic illustration of a second step in an exemplary technique for positioning a wire balloon catheter that includes placing a balloon catheter over the guidewire.
FIG. 21C is a schematic illustration of a third step in an exemplary technique for positioning a wire balloon catheter that includes placing an optical arrangement in the balloon catheter.

An exemplary procedure that may be used to position a catheter that employs a guidewire in a center lumen of the catheter is illustrated in FIGS. 21A-C. First, the guidewire 2100 can be placed within the organ 2150, as shown in FIG. 21A. Next, an outer housing 2110 of the catheter, together with a balloon 2120, can be threaded over the guidewire 2100, as shown in FIG. 21B. Finally, the inner housing 2130, which may contain an optical arrangement, can be threaded down the catheter center lumen as shown in FIG. 21C, and an imaging procedure using the optical arrangement can be performed.

Figure 22:
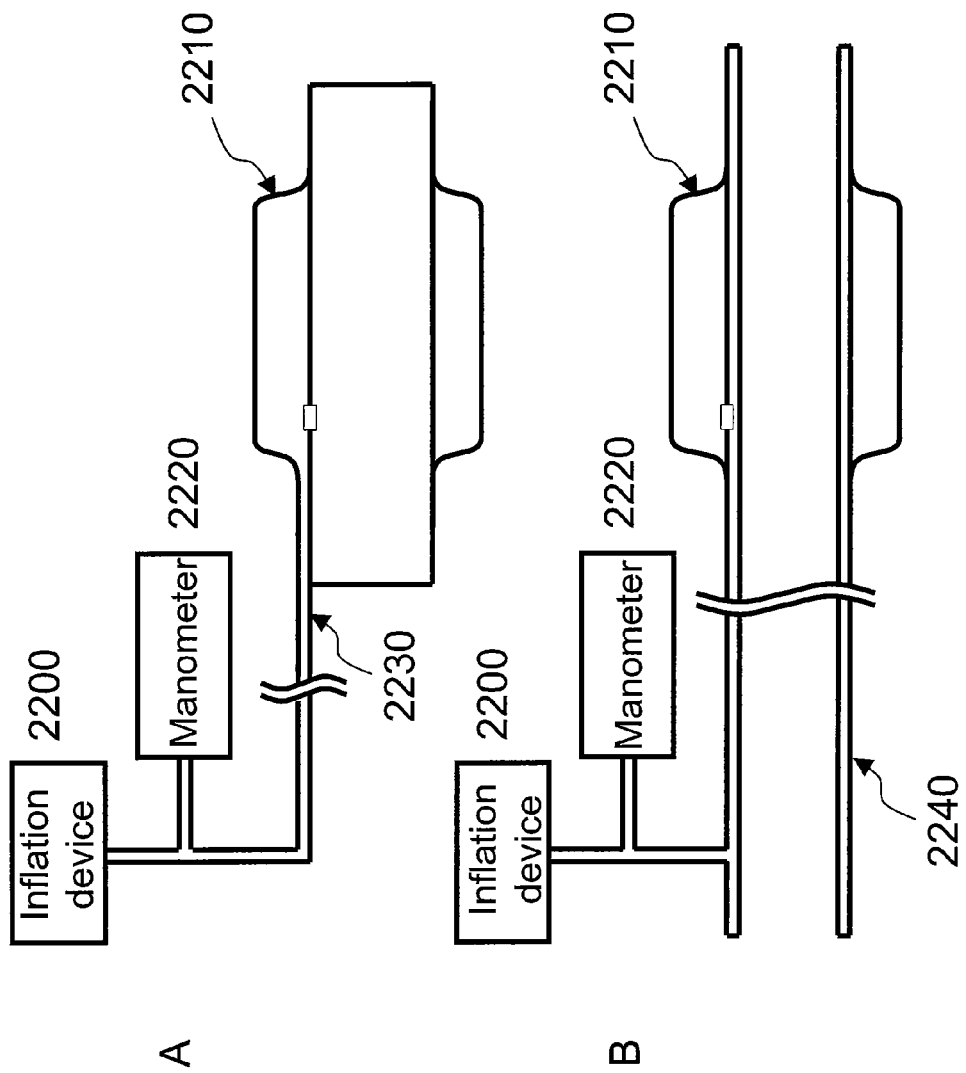
FIG. 22A is a schematic illustration of an exemplary balloon catheter which includes a single channel configured to deliver an inflation material from a remote location to the balloon.
FIG. 22B is a schematic illustration of an exemplary balloon catheter which includes two sheaths, where the inflation material can be provided between the sheaths.

Two exemplary configurations of a balloon catheter are shown in FIG. 22. In FIG. 22A, a device 2200 that may include a source of pressurized air or gas can be used to inflate a balloon 2210. A tube or other small passageway 2230 can be provided that is connected to the balloon 2210 surrounding the catheter and which allows transfer of the pressurized air or gas to the balloon 2210. Pressure within the balloon 2210 being inflated can be monitored using a manometer 2220. This pressure can be used to optimize the balloon inflation as well as to assess placement of the catheter by monitoring pressure within a surrounding organ which may be contacted by the inflated balloon 2210. Alternatively, a passageway 2240 can be provided along an outer sheath of the catheter, which can allow transfer of the pressurized air or gas to the balloon 2210, as shown in FIG. 22B. A balloon that is capable of changing its diameter in response to pressure changes may be used, where focus depth can be controlled by varying the balloon diameter and thus moving the surrounding tissue to be allows transfer of the pressurized air or gas to the balloon 2210. with respect to the imaging lens.

Figure 23:
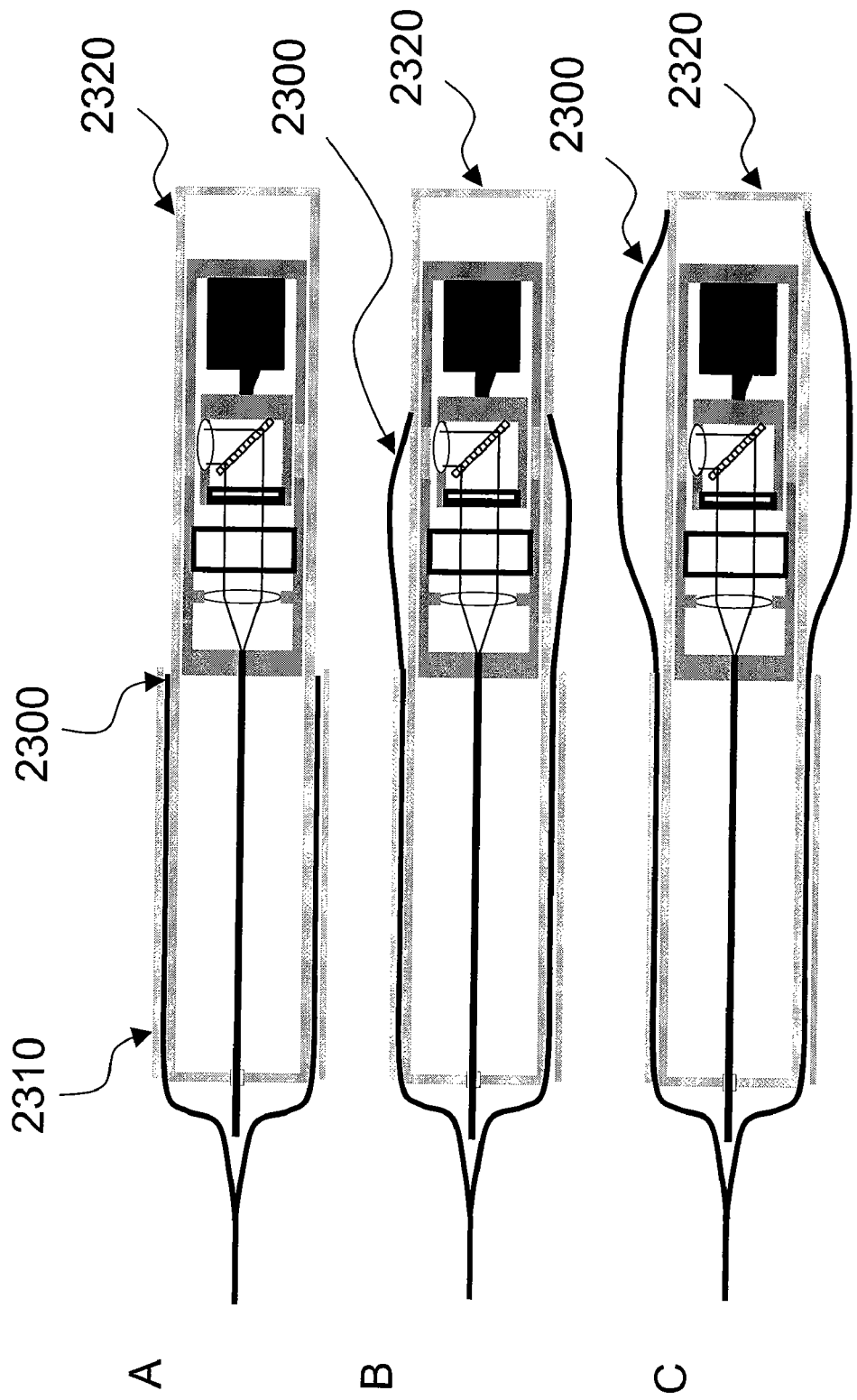
FIG. 23A is a schematic illustration of a centering arrangement having a form of a wire cage, where the arrangement is contained within an outer sheath.
FIG. 23B is a schematic illustration of the centering arrangement having the form of a wire cage, where the arrangement is partially protruding from the outer sheath.
FIG. 23C is a schematic illustration of the centering arrangement having the form of a wire cage, where the arrangement is fully extended from outer sheath.

An exemplary catheter design that may be used in accordance with another exemplary embodiment of the present invention is shown in FIGS. 23A-23C. This catheter design can be configured to use one or more expandable wire strands 2300 to center an inner optical core of an imaging device within a luminal organ. The catheter may include an additional sheath 2310 and a set of expandable wire strands 2300 located within the sheath 2310 that may be provided around the outer housing 2320, as shown in FIG. 23A. After placement of the catheter, the wire strands 2300 can be pushed through the sheath 2310 to protrude from the end thereof as shown in FIG. 23B Alternatively, the sheath 2310 can be retracted from the outer housing 2320. A sufficient length of the wire strands 2300 can be exposed around the outer housing 2320 to allow the wire strands 2300 to expand the surrounding organ or tissue as shown in FIG. 23C, and to center the housing 2320. After the imaging procedure is performed, the wire strands 2300 may be pulled back into the sheath 2310 and the catheter can be removed.

Exemplary OCT and RCM techniques can reject or ignore multiply scattered light received from a tissue sample being imaged, and thereby detect singly backscattered photons that may contain structural information. Each of these techniques, however, can reject multiply scattered light in a different way.

For example, the RCM techniques may employ confocal selection of light reflected by tissue being imaged from a tightly focused incident beam. RCM techniques can be implemented by rapidly scanning the focused beam in a plane parallel to the tissue surface, which may provide transverse or en face images of the tissue. A large numerical aperture (NA), which can be used with conventional RCM techniques, may yield a very high spatial resolution (e.g., approximately 1-2 µm that can allow visualization of subcellular structure. Imaging procedures using a high NA, however, can be particularly sensitive to aberrations that can arise as light propagates through inhomogeneous tissue. Therefore, high-resolution imaging using RCM techniques may be limited to a depth of about 100-400 µm.

The OCT techniques can utilize coherence gating principles for optical sectioning and may not rely on the use of a high NA lens. OCT techniques may thus be performed using an imaging lens having a relatively large confocal parameter. This can provide a greater penetration depth into the tissue being imaged (e.g., approximately 1-3 mm) and a cross-sectional image format. These advantages may come at the expense of a reduced transverse resolution, which can be typically on the order of about 10-30 µm.

Thus, in view of the distinctions described above, the exemplary OCT and RCM techniques can offer different imaging information which may be complementary. For example, RCM techniques can provide subcellular detail, whereas OCT techniques can provide, e.g., architectural morphology. Imaging information from these two size regimes can be critical for histopathologic diagnosis, and in many cases, it may be difficult if not impossible to make an accurate diagnosis without using both. Although a combination of these disparate imaging techniques may conventionally utilize extensive engineering efforts which can compromise performance, SECM and SD-OCT techniques can share certain components. Therefore, a high-performance multi-modality system employing both of these imaging techniques can be provided that does not include a substantial increase in complexity or cost relative to a system that may use either technique alone.

Figure 24:
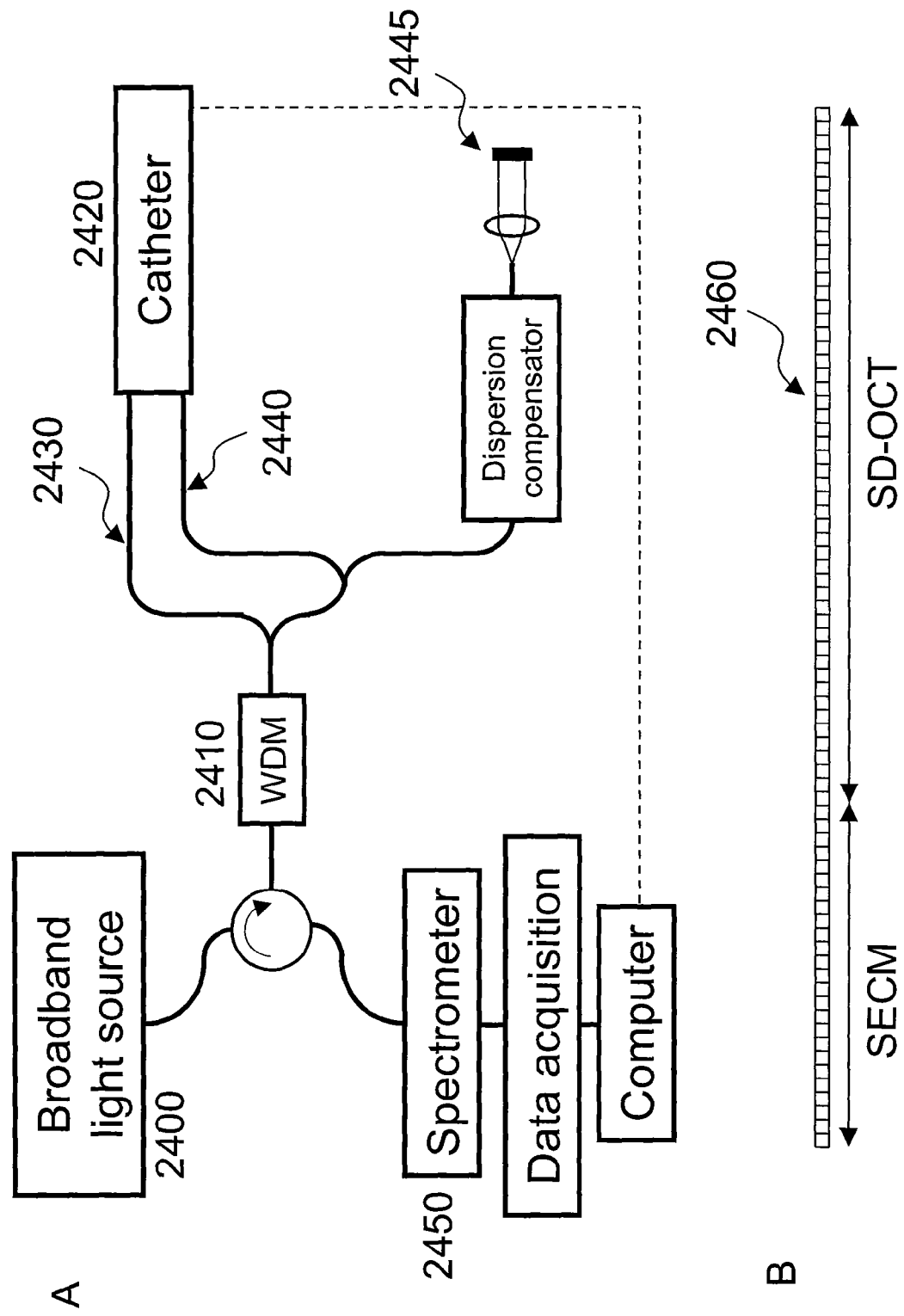
FIG. 24A is a schematic illustration of an exemplary SECM/SD-OCT system which includes a wavelength division multiplexer and a dispersion compensator.
FIG. 24B is a schematic illustration of an exemplary spectrum which may be provided by an SECM/SD-OCT system using a linear CCD array.

An overview of an exemplary system that is capable of performing both SECM techniques and SD-OCT techniques in accordance with an exemplary embodiment of the present invention is shown in FIG. 24A. In this exemplary system, a portion of a broadband light source bandwidth can be used for obtaining SECM image data, and a further portion of the bandwidth data can be used, e.g., to obtain SD-OCT data. For example, a light source 2400 can be used to provide electromagnetic energy having a bandwidth greater than, e.g., about 100 nm. Devices that may be used as a light source 2400 can include, e.g., a diode-pumped ultrafast laser (such as that available from, e.g., IntegralOCT, Femtolasers Produktions GmbH, Vienna, Germany), or an array of super luminescent diodes (which may be obtained, e.g., from Superlum, Russia).

A portion of the light source spectrum that may be used for SD-OCT data (e.g., light having a wavelength between about 810-900 nm) can be separated from a portion of the spectrum that may be used for SECM data using a wavelength division multiplexer (WDM) 2410 and transmitted to a catheter 2420 and to a reference arm 2445. Light returning from the catheter 2420 through an SECM optical fiber 2430 and an SD-OCT optical fiber 2440 can be provided to a spectrometer 2450. The spectrometer 2450 may be configured so that approximately half of the elements of the exemplary CCD array 2460 shown in FIG. 24B can detect a signal associated with the SECM data, and approximately half of the CCD elements can detect a signal associated with the SD-OCT data. The SD-OCT data can be converted into axial structural data, e.g., by performing a Fourier transformation following interpolation of the SD-OCT data from wavelength space to k-space. For example, if the spectrometer 2450 has a resolution of approximately 0.1 nm, a total SD-OCT ranging depth may be greater than about 2.0 mm. Axial image resolution using the SD-OCT technique may be approximately 5 µm.

Figure 25:
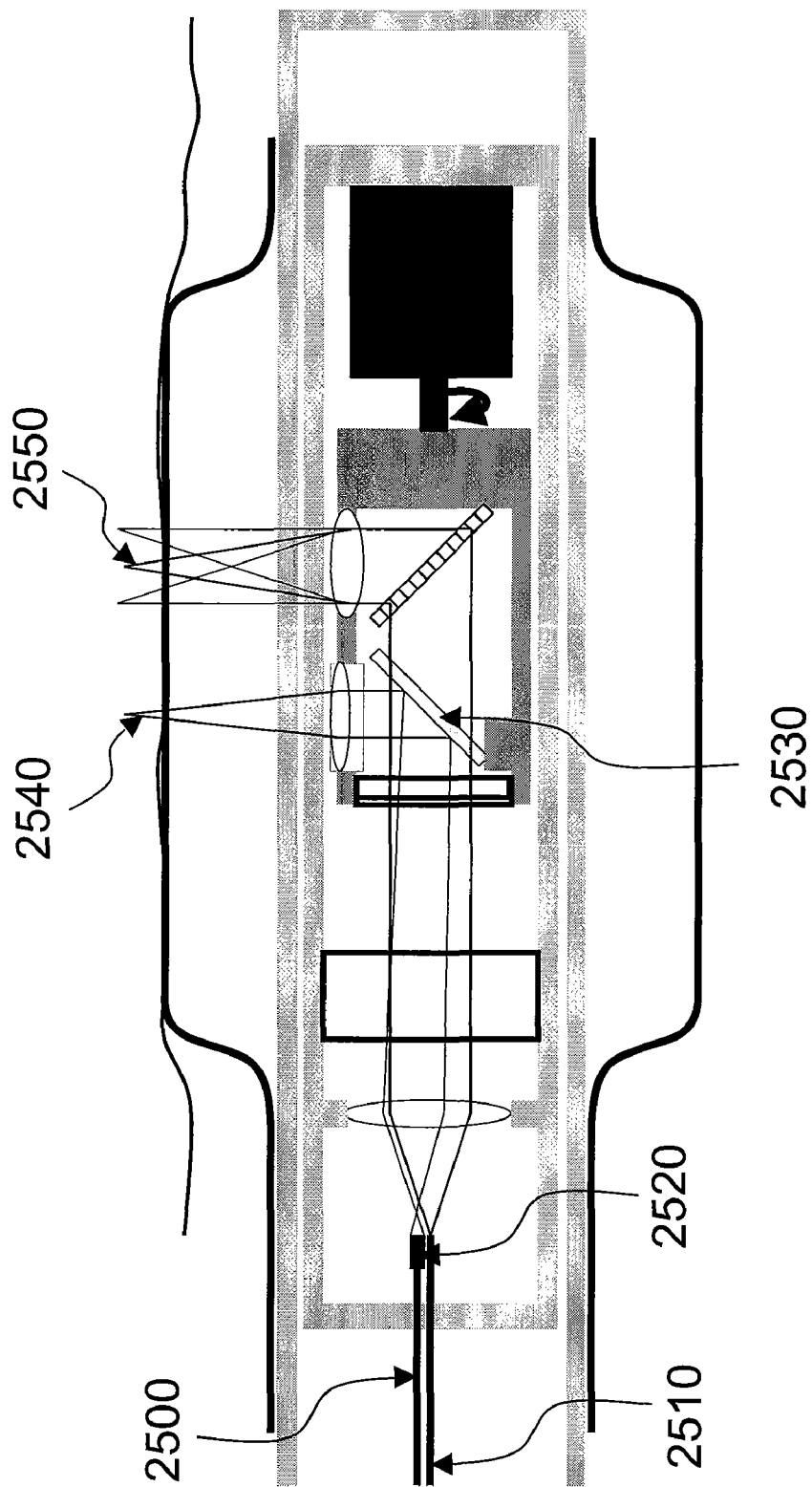
FIG. 25 is a schematic illustration of an exemplary SECM/SD-OCT probe.

A schematic overview of an exemplary SECM/SD-OCT probe is shown in FIG. 25. This probe is similar to the probe shown, e.g., in FIG. 15, and it further includes an arrangement configured to provide an SD-OCT beam path. In order to obtain an SD-OCT beam, an OCT optical fiber 2500 can be inserted into the inner housing, together with an SECM optical fiber 2510. The OCT optical fiber 2500 can be configured to illuminate a small lens 2520. A confocal parameter and a spot size for the SD-OCT beam can be selected to achieve cross-sectional imaging over a range of depths. Exemplary values of the confocal parameter spot size can be, e.g., be approximately 1.1 mm and 25 µm, respectively. The NA of the SD-OCT lens 2520 can be selected to be, e.g., approximately 0.02, and a collimated beam diameter of the SD-OCT beam can be selected to be, e.g., approximately 200 µm. A dichroic mirror 2530 can be placed before the SECM grating to reflect the SD-OCT light beam 2540 and transmit the SECM light beam 2550. The dichroic mirror 2530 shown in FIG. 25 is arranged at an angle of approximately 45 degrees with respect to the SD-OCT light beam 2540. This angle can be increased by using an appropriate coating on the mirror 2530, which can allow the SD-OCT beam 2540 to overlap the SECM beam 2550 for a more precise spatial registration of the two images. Optical aberrations of the SD-OCT beam 2540 which may be produced, e.g., by a curved window or balloon can be corrected by using a cylindrical element to pre-compensate for astigmatism as shown in FIG. 12B.

Figure 26:
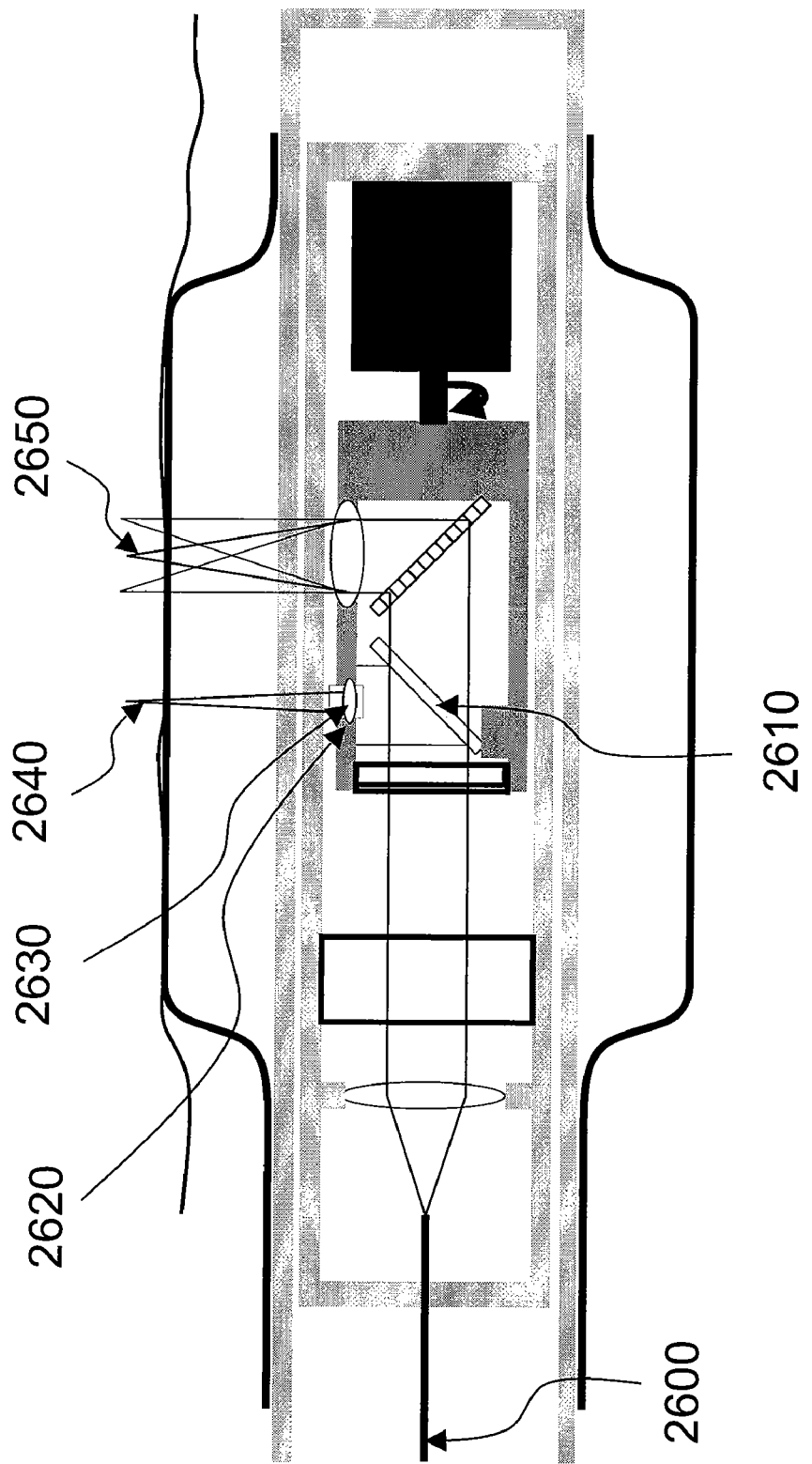
FIG. 26 is a schematic illustration of an exemplary SECM/SD-OCT probe which includes a single optical fiber for both the SECM and the SD-OCT arrangements.

A further exemplary embodiment of a catheter probe which may be used for both SECM imaging and SD-OCT imaging is shown in FIG. 26. Broadband light may be provided through a single optical fiber 2600, instead of through two separate fibers 2500, 2510 as shown in FIG. 25. A portion of the light which may be used to form an SD-OCT beam 2640 may be reflected out of the optical path of the SECM beam 2650 using a dichroic mirror 2610. The diameter of the SD-OCT beam 2640 may be reduced by an aperture 2620 and/or by focusing the SD-OCT beam 2640 using a lens 2630. The SD-OCT arrangement may also be used to locate a surface of a tissue being imaged using an SECM technique, even with SD-OCT depth resolutions between about 20-100 µm. This can be performed even if the bandwidth of the SD-OCT beam 2640 is not sufficient to obtain a high quality SD-OCT image.

Figure 27:
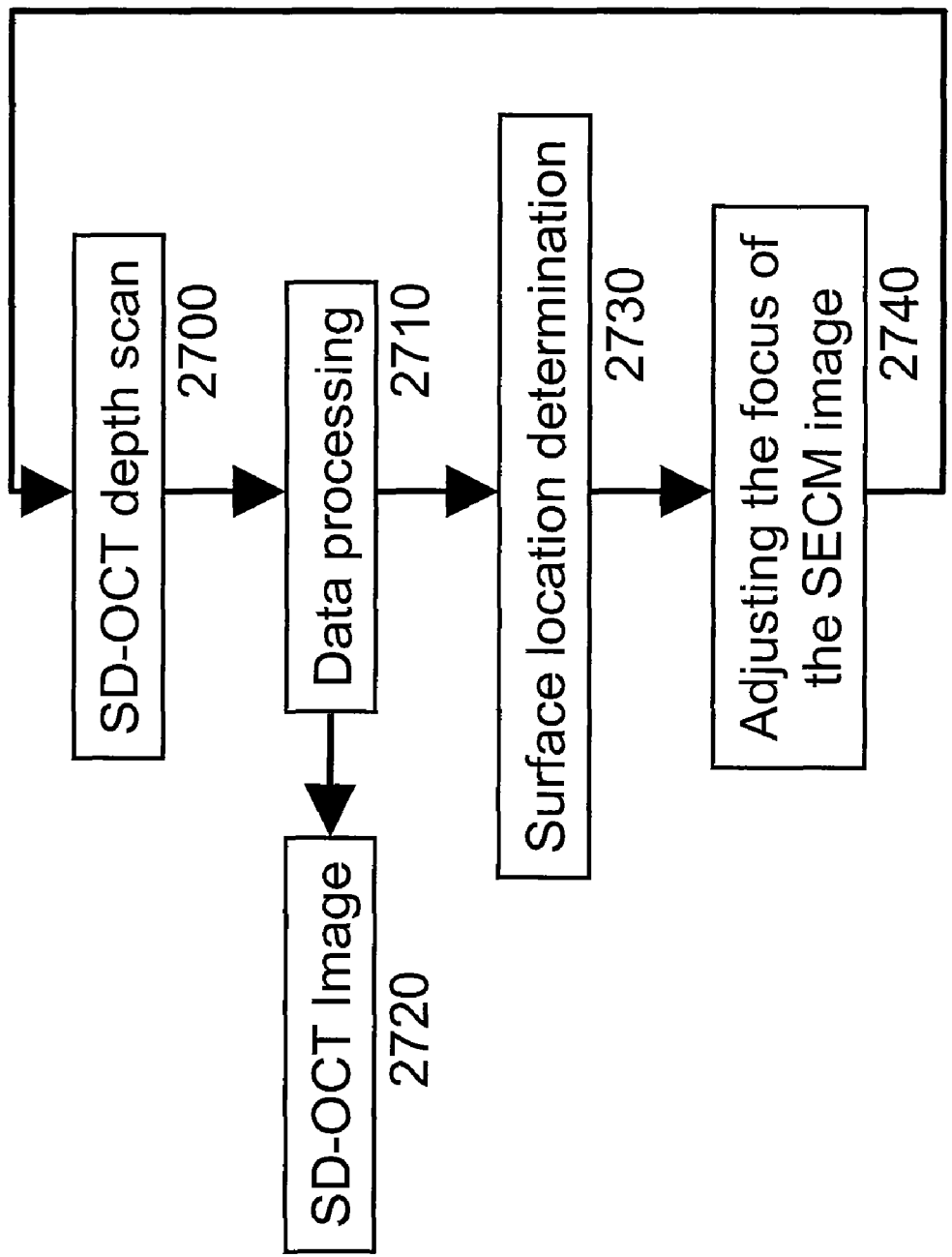
FIG. 27 is an exemplary flow diagram of a technique which may be used to adjust a focus for an SECM image using SD-OCT data.

Data obtained from an exemplary SD-OCT image can be used to adjust a focal plane of an SECM beam. An exemplary flow diagram illustrating this technique is shown in FIG. 27. For example, SD-OCT image data may be obtained from a depth scan (step 2700) and subsequently processed (step 2710). The image data may be analyzed and displayed as an SD-OCT image (step 2720). This image data may also be used to determine the location of a tissue surface (step 2730) using, for example, edge detection algorithms. Once the surface location of the tissue has been determined, a variable focus mechanism can be used to adjust a location of a focal plane of the SECM arrangement (step 2740). This focus control technique can be performed rapidly (e.g., in less than about 100 ms), which may allow for real-time tracking and focusing of a tissue surface. A location of a tissue edge can be calibrated using an angle that is formed with respect to the SECM beam.

Figure 28:
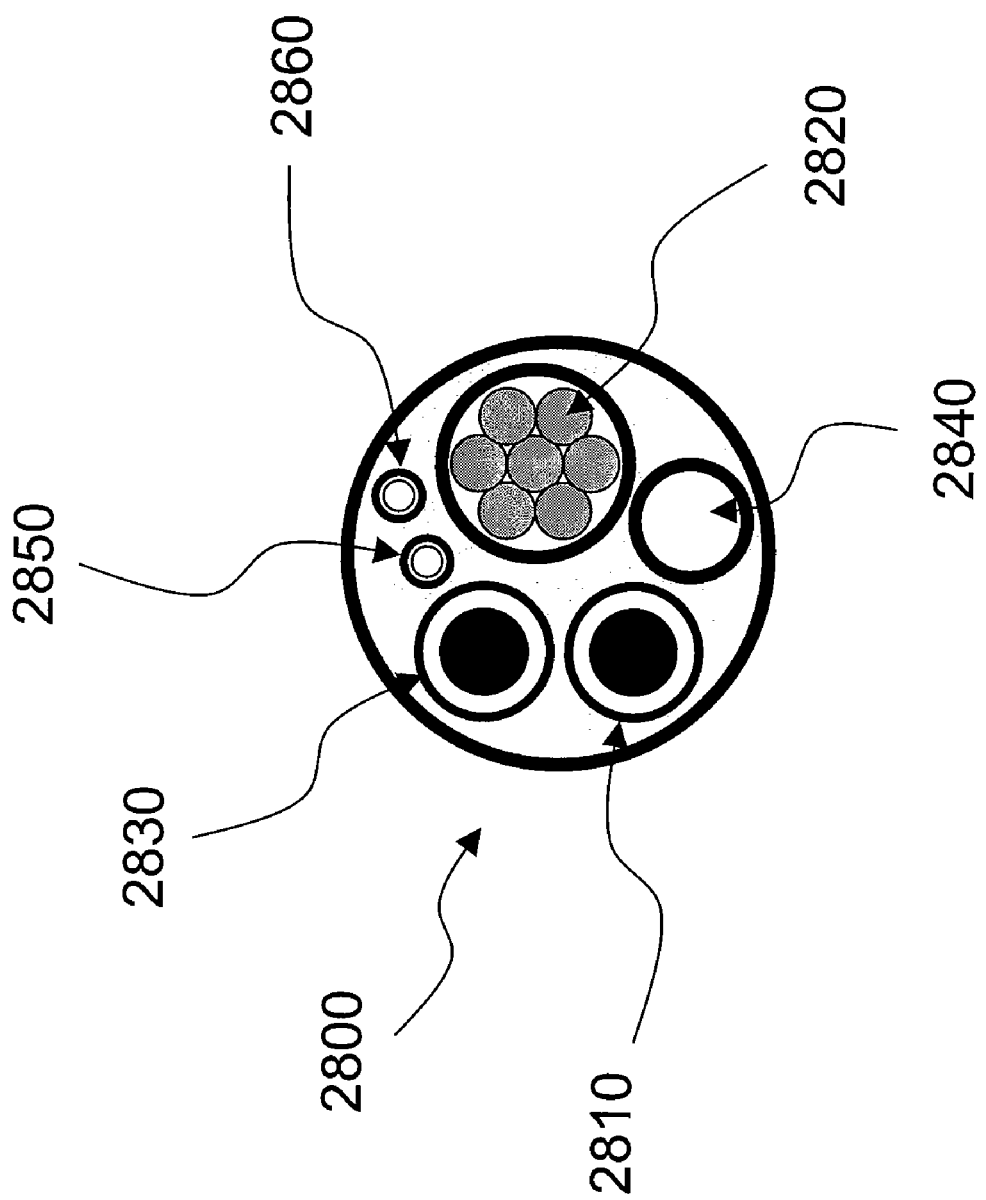
FIG. 28 is a schematic illustration of a cross section of an exemplary catheter cable.

A cross section of an exemplary catheter cable 2800 which may be used with certain exemplary embodiments of the present invention is shown in FIG. 28. The cable 2800 may include, e.g., a pullback cable 2810, a plurality of wires 2820 configured to supply electric power to a motor, a focus control cable 2830, a channel 2840 configured to provide a gas or other fluid to an inflatable balloon or membrane, an SECM optical fiber 2850, and/or an SD-OCT optical fiber 2860.

Figure 29:
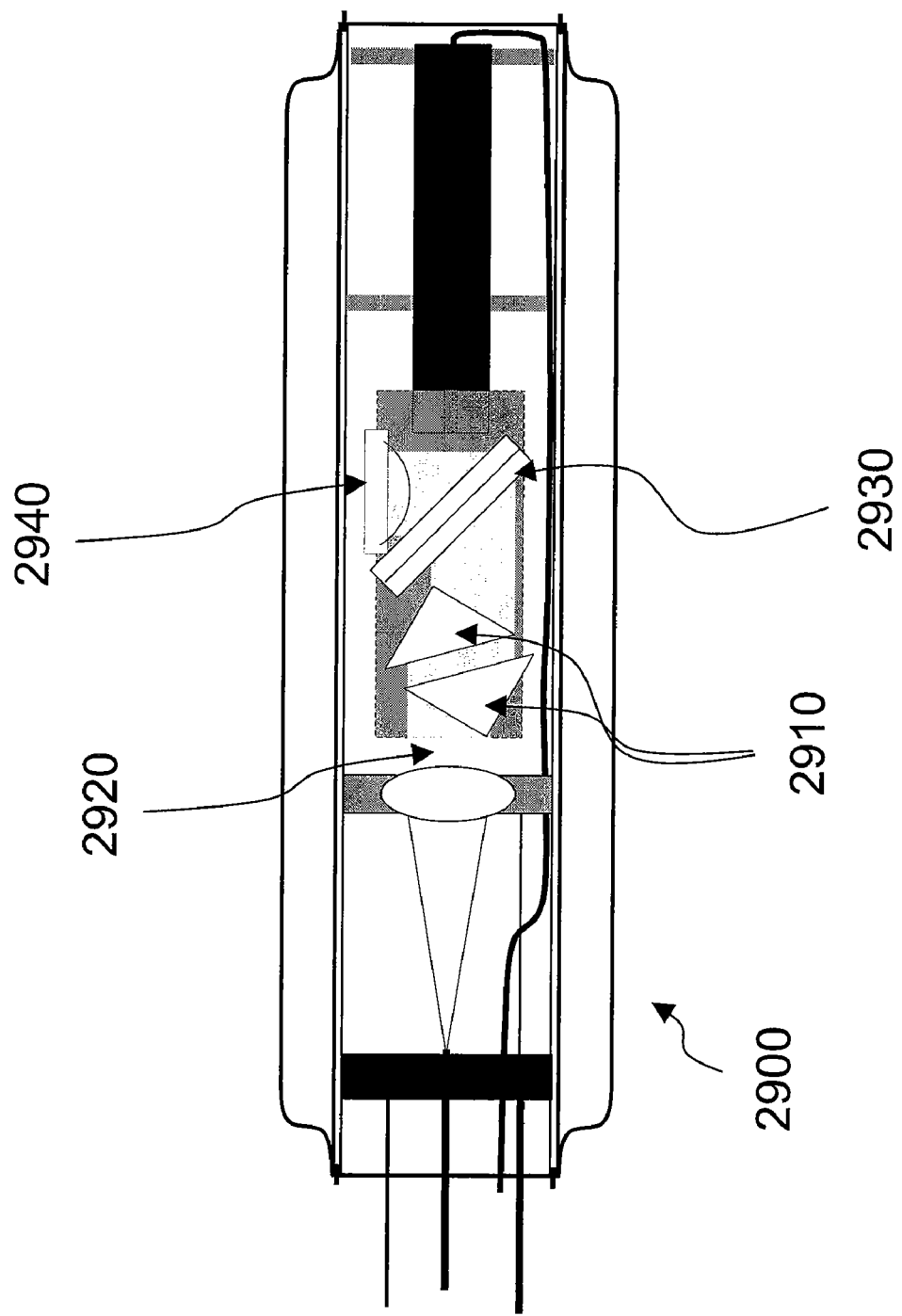
FIG. 29 is a schematic illustration of an exemplary probe which includes a beam deflection optical arrangement that may provide a more compact probe configuration.

A schematic illustration of an exemplary SECM probe 2900 is shown in FIG. 29. The probe 2900 includes two prisms 2910 which may be configured to deflect a beam 2920 before it passes through a grating 2930 and an imaging lens 2940. This exemplary configuration can provide more space within the probe 2900 for the objective lens 2940, which can result in a higher NA and/or a size reduction of the probe 2900.

Figure 30:
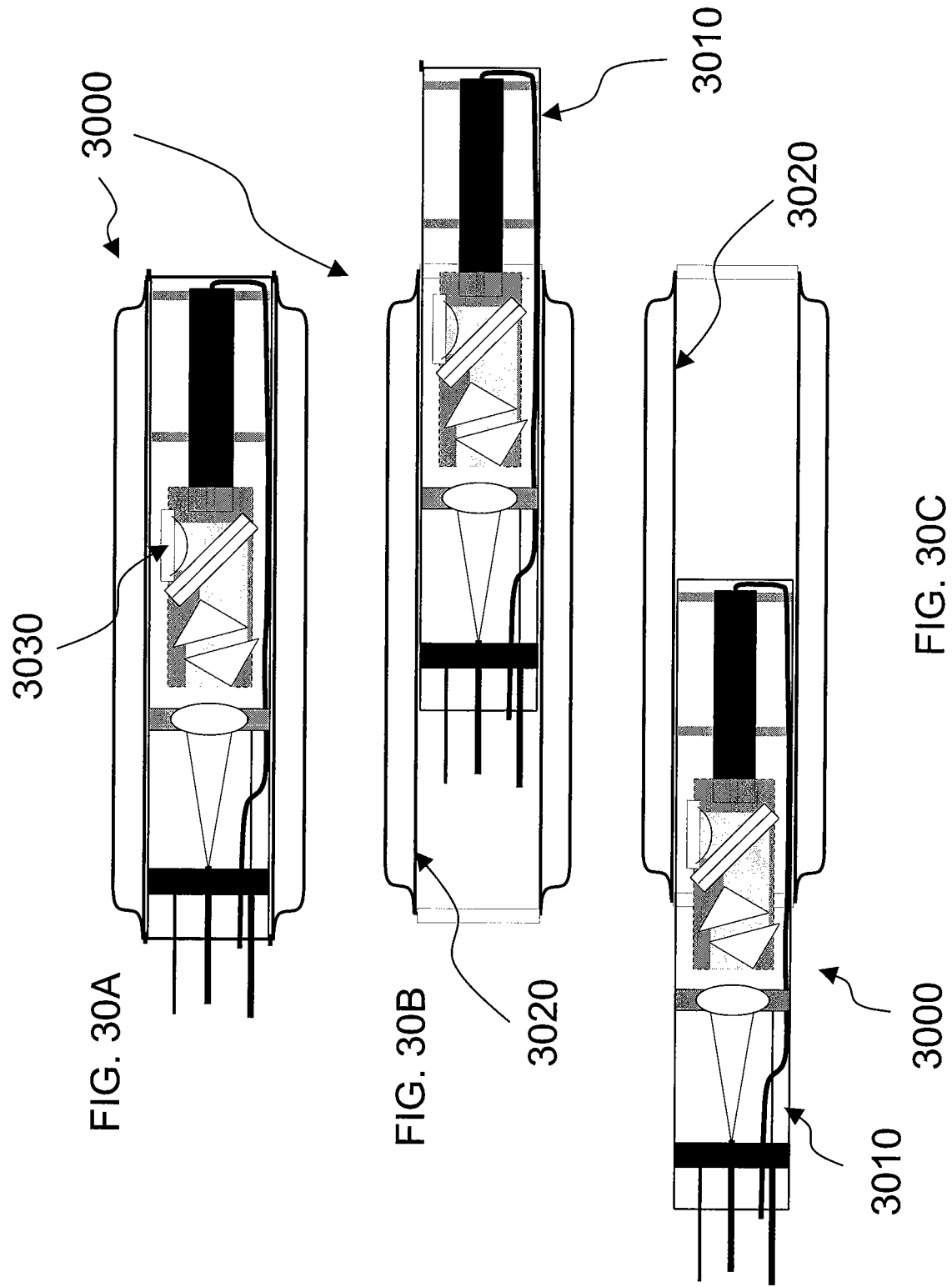
FIG. 30A is a schematic illustration of a translational scanning technique showing a compact configuration of a probe during delivery of the probe to the site to be imaged.
FIG. 30B is a schematic illustration of the translational scanning technique showing an inner housing of the probe positioned at a distal limit of a translational range.
FIG. 30C is a schematic illustration of the translational scanning technique showing the inner housing of the probe positioned at a proximal limit of the translational range.

A further reduction in probe length can be achieved using the exemplary probe configuration 3000 shown in FIGS. 30A-30C. The probe 3000 can include an inner housing 3010 which may be provided within an outer housing 3020 while the probe 3000 is delivered to the imaging location, as shown in FIG. 3A. After the probe 3000 is placed and centered within the tissue or organ to be imaged, the inner housing 3010 can slide through the outer housing 3020 to provide an extended pullback range, as shown in FIGS. 30B and 30C. For example, providing an imaging lens 3020 near a center of the inner housing 3010 can provide increased positional stability at the extreme scanning locations shown in FIGS. 30B and 30C.

Figure 31:
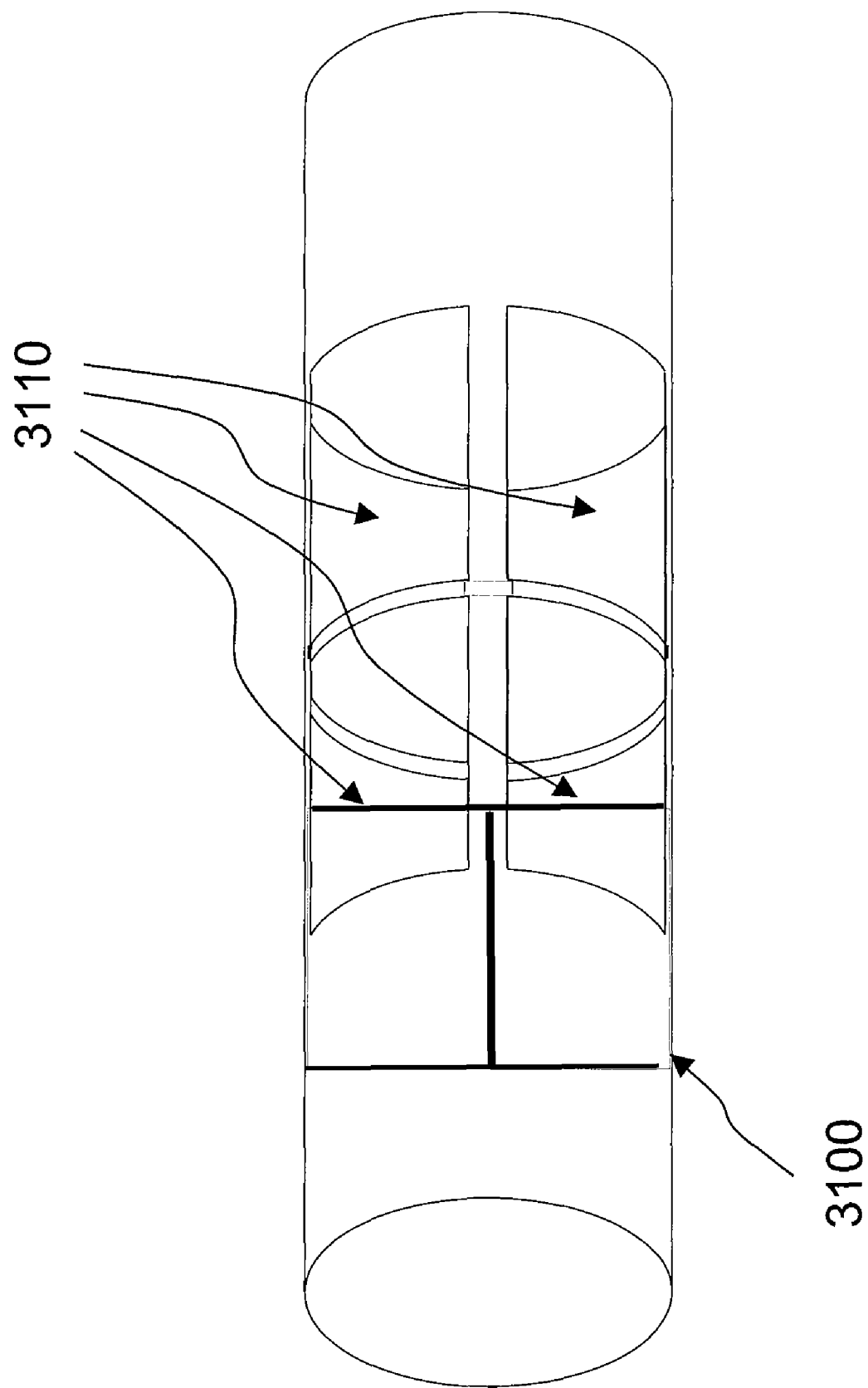
FIG. 31 is a schematic illustration of an outer housing which includes transparent openings.

An exemplary outer housing 3100 is shown in FIG. 31. The outer housing 3100 can be made of rigid materials such as, e.g., stainless steel or plastic. It may include one or more gaps 3110 which can allow light to pass therethrough to generate image data without introducing optical aberrations. Optionally, the gaps 3110 may include transparent windows.

Figure 32:
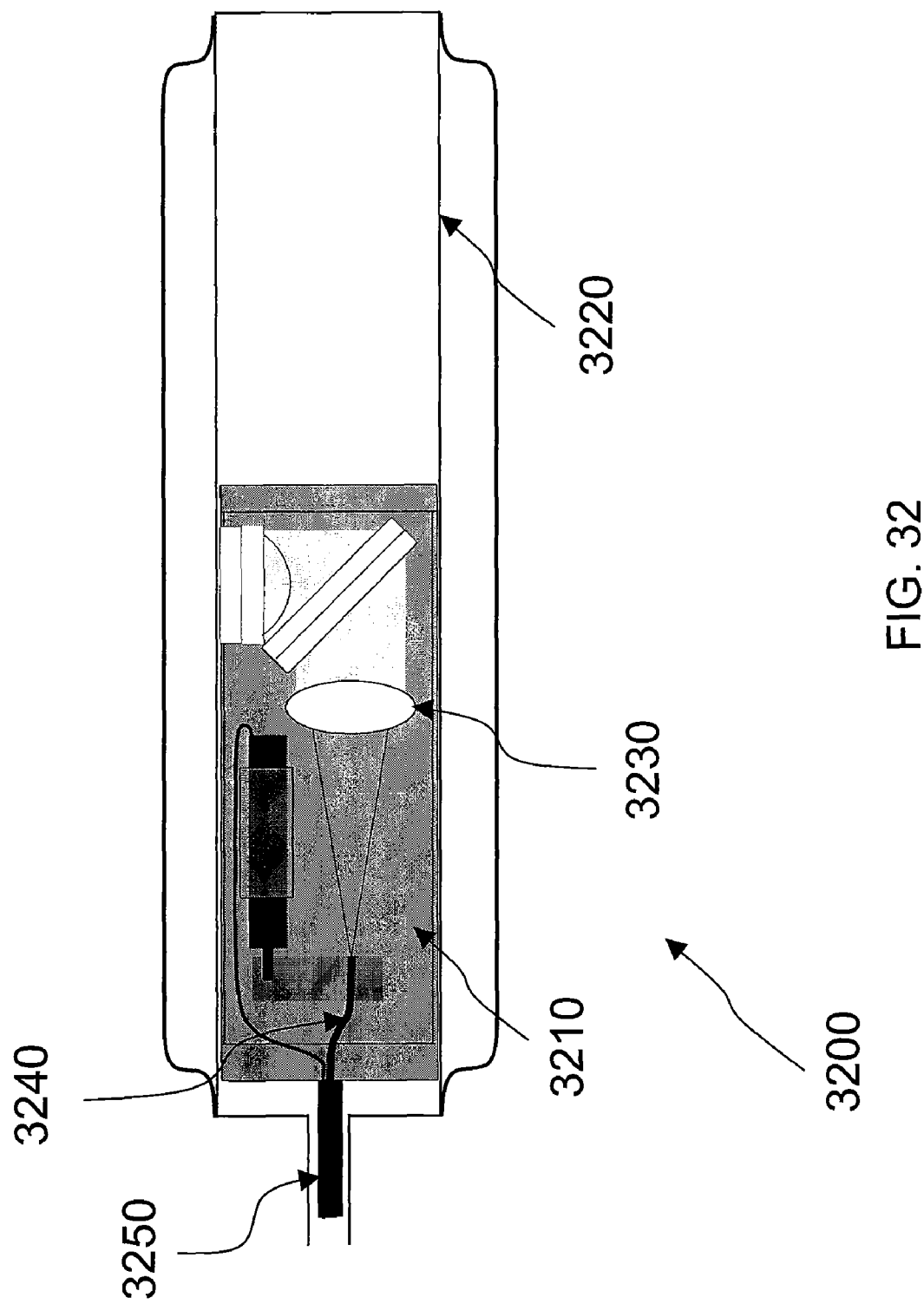
FIG. 32 is a schematic illustration of an exemplary compact probe which includes an off-center collimation optical arrangement and which is configured to provide external rotational scanning.

FIG. 32 shows an exemplary probe in accordance with certain exemplary embodiments of the present invention. The probe 3200 can provide a compact configuration of components and a small overall probe size. For example, a cylindrical inner housing 3210 can be configured to rotate and move freely within a cylindrical outer housing 3220, allowing a collimating lens 3230 and an optical fiber 3240 to be placed away from a center axis of the inner housing 3210. Scanning of a region of tissue to be imaged can be performed externally, where motion of the inner housing 3210 can be controlled using a pullback cable 3250.

In certain exemplary embodiments of the present invention, a liquid such as, e.g., water or an index-matching oil can be provided in a space between an imaging lens and a surface of the tissue to be imaged. Providing such a liquid can, e.g., improve optical parameters such as a NA and/or reduce back reflections of a light beam used to obtain image data.

An exemplary probe configuration 3300 which can provide a high NA for obtaining image data is shown in FIGS. 33A and 33B. For example, an inner housing 3310 can be provided in an outer housing 3320, which may also include an uninflated balloon 3330. The uninflated balloon 3330 may be inflated such that it can expand forward of the outer housing 3320. The inner housing 3310 may then be deployed outside of the outer housing 3310 and within the inflated balloon 3340. An elastic arrangement 3350 can be provided in a compressed configuration between the inner housing 3310 and the outer housing 3320, as shown in FIG. 33A. The elastic arrangement 3350 can be configured to position the inner housing 3310 against an inside wall of the inflated balloon 3340 when the inner housing 3310 is deployed, as shown in FIG. 33B. The inner housing 3310 can be configured to scan a region of tissue outside of the inflated balloon 3340 the balloon area using a pullback cable 3360. The cable 3360 can be capable of controlling both rotation and longitudinal translation (e.g., pullback) of the inner housing 3310 within the inflated balloon 3340. Spacers 3370 may be used to improve contact between the imaging optical arrangement and the wall of the inflated balloon 3340 or the adjacent tissue surface.

A further exemplary probe configuration 3400 is shown in FIGS. 34A and 34B, which can be capable of maintaining an inner probe housing 3410 against an inside wall of an outer balloon 3420, in accordance with certain exemplary embodiments of the present invention. For example, an outer balloon 3420 and an inner balloon 3430, shown uninflated in FIG. 34A, can be provided such that they surround the inner housing 3410. Each balloon may be inflated, as shown in FIG. 34B. In this exemplary configuration, the inner housing 3410 may be attached to one face of the inner balloon 3430. Rotational and translational scanning within the outer balloon 3420 may be performed by moving the inner housing 3410 together with the inner balloon 3430 relative to the outer balloon 3420.

A still further exemplary probe configuration 3500 is shown in FIGS. 35A and 35B, which can be capable of maintaining an inner probe housing 3510 against an inside wall of an outer balloon 3520, in accordance with certain exemplary embodiments of the present invention. The outer balloon 3520, shown uninflated in FIG. 35A, may be inflated within an organ or region of tissue to be imaged. An inner balloon 3530, shown uninflated in FIG. 35A, may be provided between the inner housing 3510 and the outer balloon 3520. The inner balloon 3530 may be inflated, as shown in FIG. 35B, and pressure provided by the inner balloon 3530 can be used to maintain contact between the inner housing 3510 and an inner wall of the outer balloon 3520, as shown in FIG. 35B. The exemplary probe configurations 3400 and 3500 shown in FIGS. 34 and 35, respectively, may be used without an outer housing. The uninflated balloons 3420, 3430, 3520, 3530 may be packed inside an external enclosure that can be used to deliver the probe 3400, 3500 to a desired location. Such an external enclosure can optionally be formed, e.g., from a dissolvable material.

An exemplary configuration of an SECM probe 3600 is shown in FIGS. 36A-36D, which is capable of providing a spectrally encoded line 3610 that lies perpendicular to an axis of an organ or a balloon cylinder. A bottom view of this probe configuration is provided in FIG. 36A, and a corresponding side view is shown in FIG. 36B. FIG. 36C shows a further side view in which the probe housing 3640 is deployed within an inflated balloon 3650, similar to that shown in FIG. 33B. In this exemplary configuration, a longitudinal (e.g., pullback) direction can be a primary scanning direction, such that the probe housing 3640 is moved in this longitudinal direction at a relatively fast rate of speed. Scanning in a rotational direction around a longitudinal axis can be performed at a relatively low rate compared to the longitudinal speed. The probe 3600 can be provided with positioning arrangements such as those shown, e.g., in any of FIGS. 33-35. The probe housing 3640 can include a mirror 3620 which may be configured to deflect a light beam towards a suitably positioned grating to provide a spectrally-encoded line 3610 configured as shown in FIGS. 36A and 36D.

Combination of SD-OCT and SECM imaging arrangements within a probe can provide a useful apparatus for obtaining structural information on different scales using different image formats. Data obtained for both imaging techniques can be acquired simultaneously, because the resolutions of the two techniques are different. However, useful scan rates for the two techniques may not be compatible with each other. For example, a typical SECM scan rate can be provided using a rotation rate, e.g., of about 1 Hz and a longitudinal pullback speed, e.g., of approximately 1 mm/s. Typical scan rates for obtaining SD-OCT image data can be, e.g., approximately 50-100 Hz in a rotational direction and, e.g., approximately 0.2-0.5 mm/s in a longitudinal direction.

One technique which may be used to obtain comprehensive image data that is properly sampled for both techniques is to conduct an additional comprehensive SD-OCT scan, sampled appropriately, following acquisition of the SECM data set. This technique may increase the data acquisition time for a tissue region by, e.g., approximately 1-2 minutes. Encoder signals obtained for both the rotating and linearly translating motors can be digitized throughout each scan. The encoder signals can be corrected for shifts in position of a balloon by quantitatively correlating SD-OCT images to determine angular and rotational offsets for each scan. This technique can provide accurate spatial registration of the SD-OCT and SECM data sets within about 500 μm.

In a further exemplary embodiment of the present invention, an imaging arrangement provided, e.g., in a probe may be operated in an abbreviated imaging mode (e.g., 'scout imaging') to determine if a catheter which may be used to deliver the probe is properly positioned within the organ or tissue region to be imaged. A comprehensive set of image data can be obtained after proper catheter placement is confirmed.

In a still further exemplary embodiment of the present invention, a balloon centering catheter may be inflated using a material that is optically transparent other than air such as, e.g., water, heavy water (D2O), oil, etc. A lubricating agent may also be used to aid insertion of the catheter. In certain exemplary embodiments of the present invention, a mucousal removal agent may be applied prior to obtaining image data to reduce the amount of mucous present in the organ to be imaged, where presence of such mucous may reduce image quality.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with any OCT system, OFDI system, SD-OCT system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An apparatus comprising:
   a first arrangement configured to provide first data associated with a first signal received from at least one region of a sample, wherein the region has a linear dimension that is not more than about 10 microns;
   a second arrangement configured to provide second data associated with a second signal received from the sample and a third signal received from a reference, wherein the first and second data are provided substantially simultaneously by the first and second arrangements; and
   a third arrangement configured to generate further data based on the first and second data.

2. The apparatus according to claim 1, wherein the third arrangement is further configured to generate at least one of a two-dimensional image or a three-dimensional image based on the further data.

3. The apparatus according to claim 1, wherein the first and second data are associated with approximately the same location on the one sample.

4. The apparatus according to claim 1, wherein the first and second arrangements are provided in at least one of a probe.

5. The apparatus of claim 4, further comprising a positioning arrangement configured to position at least one of the probe at a particular location relative to the sample based on at least one of the first data or the second data.

6. The apparatus according to claim 1, wherein the first and second arrangements include a common component.

7. The apparatus according to claim 6, wherein the common component is provided in a wavelength swept-source arrangement.

8. The apparatus according to claim 1, wherein the at least one first arrangement is configured to obtain confocal microscopy information.

9. The apparatus according to claim 8, wherein the confocal microscopy information is reflectance confocal microscopy information.

10. The apparatus according to claim 1, wherein the first arrangement is configured to obtain spectral encoding microscopy information.

11. The apparatus according to claim 1, wherein the at least one second arrangement is configured to obtain optical coherence tomography information.

12. The apparatus according to claim 1, wherein the at least one second arrangement is configured to obtain optical coherence tomography information associated with a signal provided by a source arrangement having a plurality of wavelengths, and further comprising a plurality of detectors configured to detect a spectral interference between the second and third signals based on the wavelengths.

13. The apparatus according to claim 1, wherein the at least one second arrangement is configured to obtain optical coherence tomography information associated with a signal provided by a source arrangement whose wavelength varies over time.

14. The apparatus of claim 1, further comprising:
a fourth arrangement configured to control at least one of the first arrangement or the second arrangement based on previously-obtained at least one of the first data or the second data.

15. The apparatus of claim 1, further comprising:
a fifth arrangement configured to generate an image based on the first and second data.

16. The apparatus of claim 1, further comprising:
a sixth arrangement configured to generate at least one first image based on the first data and at least one second image based on the second data, wherein the first and second images are associated with one another based on the first and second data.

17. The apparatus of claim 1, further comprising a focusing arrangement configured to control at least one of a focal length or a focal position associated with at least one of the first arrangement or the second arrangement based on at least one of the first data or the second data.

18. The apparatus of claim 1, wherein the first data is associated with at least one first location within the at least one region, and the second data is associated with at least one second location of the sample.

19. The apparatus of claim 1, wherein the at least one sample is an anatomical structure.

20. The apparatus of claim 1, further comprising a focusing arrangement configured to control at least one of a focal length or a focal position associated with at least one of the first arrangement or the second arrangement when at least one of the first data or the second data are being acquired.

21. A method for obtaining particular data associated with at least one sample, comprising:
obtaining first data associated with a first signal received from at least one region of the at least one sample, wherein the region has a linear dimension that is not more than about 10 microns;
obtaining second data associated with a second signal received from the at least one sample and a third signal received from a reference, wherein the first and second data are provided substantially simultaneously; and
using a configured computing arrangement, generating the particular data based on the first and second data.

22. An apparatus comprising:
a first arrangement configured to provide first data associated with a first signal forwarded to at least one region of a sample, wherein the region has a linear dimension that is not more than about 10 microns;
a second arrangement configured to provide second data associated with a second signal forwarded to the sample and a third signal forwarded to a reference, wherein the first and second data are provided substantially simultaneously by the first and second arrangements; and
a third arrangement configured to generate further data based on third and fourth data received from the at least one region and the reference respectively which correspond to the first and second data, respectively.

23. An apparatus comprising:
a first arrangement configured to provide first data associated with a first signal received from at least one region of a sample, wherein the region has a linear dimension that is not more than about 10 microns;
a second arrangement configured to provide second data associated with a second signal received from the sample and a third signal received from a reference, wherein the first and second arrangements are provided in at least one of a probe;
a third arrangement configured to generate further data based on the first and second data; and
a positioning fourth arrangement configured to position the probe at a particular location relative to the sample based on at least one of the first data or the second data.

* * * * *